United States Patent
Clarke et al.

(10) Patent No.: US 12,290,433 B2
(45) Date of Patent: May 6, 2025

(54) FLUOROSILICONE COPOLYMERS

(71) Applicant: ForSight Vision6, Inc., Brisbane, CA (US)

(72) Inventors: Matthew Clarke, Brisbane, CA (US); Guy Oren, Brisbane, CA (US); Phil Costanzo, Brisbane, CA (US); Eugene de Juan, Jr., Brisbane, CA (US)

(73) Assignee: ForSight Vision6, Inc., Brisbane, CA (US)

( * ) Notice: Subject to any disclaimer, the term of this patent is extended or adjusted under 35 U.S.C. 154(b) by 798 days.

(21) Appl. No.: 17/600,571

(22) PCT Filed: Apr. 3, 2020

(86) PCT No.: PCT/US2020/026706
§ 371 (c)(1),
(2) Date: Sep. 30, 2021

(87) PCT Pub. No.: WO2020/206343
PCT Pub. Date: Oct. 8, 2020

(65) Prior Publication Data
US 2022/0168464 A1  Jun. 2, 2022

Related U.S. Application Data

(60) Provisional application No. 62/830,186, filed on Apr. 5, 2019.

(51) Int. Cl.
| | |
|---|---|
| *A61F 2/16* | (2006.01) |
| *A61L 27/18* | (2006.01) |
| *C08G 77/00* | (2006.01) |
| *C08G 77/24* | (2006.01) |
| *C08G 77/385* | (2006.01) |

(52) U.S. Cl.
CPC ............ *A61F 2/16* (2013.01); *A61F 2/1613* (2013.01); *A61L 27/18* (2013.01); *C08G 77/24* (2013.01); *C08G 77/385* (2013.01); *C08G 77/80* (2013.01); *A61L 2430/16* (2013.01)

(58) Field of Classification Search
CPC ......... C08G 77/24; C08G 77/80; C08L 83/08; C09D 183/08
USPC .................................................... 528/42–43
See application file for complete search history.

(56) References Cited

U.S. PATENT DOCUMENTS

| | | |
|---|---|---|
| 3,006,878 A | 10/1961 | Talcott |
| 3,576,020 A | 4/1971 | Loree et al. |
| 3,702,823 A | 11/1972 | Ki |
| 4,287,353 A | 9/1981 | Bluestein |
| 4,355,121 A | 10/1982 | Evans |
| 5,391,590 A | 2/1995 | Gerace et al. |
| 5,444,106 A | 8/1995 | Zhou et al. |
| 5,610,230 A | 3/1997 | Yoshida et al. |
| 6,045,535 A | 4/2000 | Ben Nun |
| 6,200,581 B1 | 3/2001 | Lin et al. |
| 6,201,091 B1 | 3/2001 | Halloran et al. |
| 6,613,343 B2 | 9/2003 | Dillingham et al. |
| 7,976,520 B2 | 7/2011 | Nun |
| 8,715,345 B2 | 5/2014 | DeBoer et al. |
| 8,900,298 B2 | 12/2014 | Anvar et al. |
| 9,186,244 B2 | 11/2015 | Silvestrini et al. |
| 9,486,311 B2 | 11/2016 | Argento et al. |
| 10,011,801 B2 | 7/2018 | Deklippel et al. |
| 10,098,831 B2 | 10/2018 | Kamei |
| 10,195,018 B2 | 2/2019 | Salahieh et al. |
| 10,526,353 B2 | 1/2020 | Silvestrini |
| 10,647,831 B2 | 5/2020 | Silvestrini et al. |
| 11,337,795 B2 | 5/2022 | Ellis |
| 11,357,618 B2 | 6/2022 | Ellis |
| 2001/0041769 A1 | 11/2001 | Iwasawa et al. |
| 2004/0015140 A1 | 1/2004 | Shields |
| 2004/0181279 A1 | 9/2004 | Nun |
| 2005/0090896 A1 | 4/2005 | Ben Nun |
| 2006/0134173 A1 | 6/2006 | Liu et al. |
| 2006/0135477 A1 | 6/2006 | Haitjema et al. |
| 2007/0244561 A1 | 10/2007 | Ben Nun |
| 2009/0198247 A1 | 8/2009 | Ben Nun |
| 2009/0234449 A1 | 9/2009 | De Juan, Jr. et al. |
| 2009/0292355 A1 | 11/2009 | Boyd et al. |
| 2010/0121444 A1 | 5/2010 | Ben Nun |
| 2011/0112636 A1 | 5/2011 | Ben Nun |
| 2012/0064022 A1 | 3/2012 | Wray et al. |
| 2012/0253459 A1 | 10/2012 | Reich et al. |
| 2013/0040073 A1 | 2/2013 | Pett et al. |
| 2013/0041382 A1 | 2/2013 | Ben Nun |
| 2013/0053954 A1 | 2/2013 | Rao et al. |

(Continued)

FOREIGN PATENT DOCUMENTS

| | | |
|---|---|---|
| CN | 101365737 A | 2/2009 |
| CN | 101402733 A | 4/2009 |

(Continued)

OTHER PUBLICATIONS

U.S. Appl. No. 17/970,131, filed Oct. 20, 2022, US 2023-0129111.

(Continued)

*Primary Examiner* — Marc S Zimmer
(74) *Attorney, Agent, or Firm* — Mintz, Levin, Cohn, Ferris, Glovsky and Popeo, P.C.

(57) ABSTRACT

Described herein, inter alia, are fluorosilicone polymers and copolymers; compositions comprising fluorosilicone polymers and copolymers; lenses, such as intraocular lenses, comprising fluorosilicone polymers and copolymers; and processes for making the fluorosilicone polymers and copolymers.

40 Claims, 16 Drawing Sheets

(56) References Cited

U.S. PATENT DOCUMENTS

| | | | |
|---|---|---|---|
| 2013/0116781 A1 | 5/2013 | Ben Nun | |
| 2013/0337226 A1 | 12/2013 | Curran et al. | |
| 2015/0087743 A1 | 3/2015 | Anvar et al. | |
| 2016/0030161 A1 | 2/2016 | Brady et al. | |
| 2016/0122594 A1* | 5/2016 | Qiu | C09J 7/201 524/588 |
| 2016/0281019 A1* | 9/2016 | Deklippel | C08L 83/04 |
| 2016/0303032 A1 | 10/2016 | Kamei | |
| 2016/0317286 A1 | 11/2016 | Brady et al. | |
| 2016/0317287 A1 | 11/2016 | Silvestrini et al. | |
| 2017/0181850 A1 | 6/2017 | de Juan, Jr. et al. | |
| 2017/0342096 A1 | 11/2017 | Silvestrini | |
| 2019/0000612 A1 | 1/2019 | Rao et al. | |
| 2019/0223998 A1 | 7/2019 | de Juan, Jr. et al. | |
| 2019/0269500 A1 | 9/2019 | de Juan, Jr. et al. | |
| 2021/0259826 A1 | 8/2021 | Ben Nun | |
| 2021/0290372 A1 | 9/2021 | Ben Nun | |
| 2021/0300003 A1* | 9/2021 | Hasegawa | B32B 25/10 |
| 2022/0010169 A1* | 1/2022 | Nietfeld | C08G 77/12 |
| 2022/0218467 A1 | 7/2022 | Oren et al. | |
| 2022/0380552 A1 | 12/2022 | Silvestrini et al. | |

FOREIGN PATENT DOCUMENTS

| | | | |
|---|---|---|---|
| CN | 104755139 A | | 7/2015 |
| EP | 0253515 A2 | | 1/1988 |
| GB | 2145423 A | | 3/1985 |
| JP | S46-008879 B | | 6/1971 |
| JP | 2018-188562 A | | 11/2018 |
| WO | WO-2015/148673 A1 | | 10/2015 |
| WO | WO-2016/049059 A1 | | 3/2016 |
| WO | WO-2018/081595 A1 | | 5/2018 |
| WO | WO 2019/058231 A1 | * | 3/2019 |
| WO | WO-2018/081595 A8 | | 6/2019 |
| WO | WO-2019/112255 A1 | | 6/2019 |
| WO | WO-2019/178873 A1 | | 9/2019 |
| WO | WO-2019/236908 A1 | | 12/2019 |
| WO | WO 2020/022406 | * | 1/2020 |
| WO | WO-2020/206343 A1 | | 10/2020 |
| WO | WO-2021/257518 A1 | | 12/2021 |

OTHER PUBLICATIONS

PCT/US2022/47293, Oct. 20, 2022, WO 2023/069630.
U.S. Appl. No. 17/166,680, filed Feb. 3, 2021, US 2021-0259826.
U.S. Appl. No. 17/221,525, filed Apr. 2, 2021, US 2021-0290372.
U.S. Appl. No. 17/364,202, filed Jun. 30, 2021, US 2022-0160495.
U.S. Appl. No. 17/575,155, filed Jan. 13, 2022, US 2022-0218467.
U.S. Appl. No. 17/722,154, filed Apr. 15, 2022, US 2022-0323205.
PCT/US22/12300, Jan. 13, 2022, WO 2022/155325.

* cited by examiner

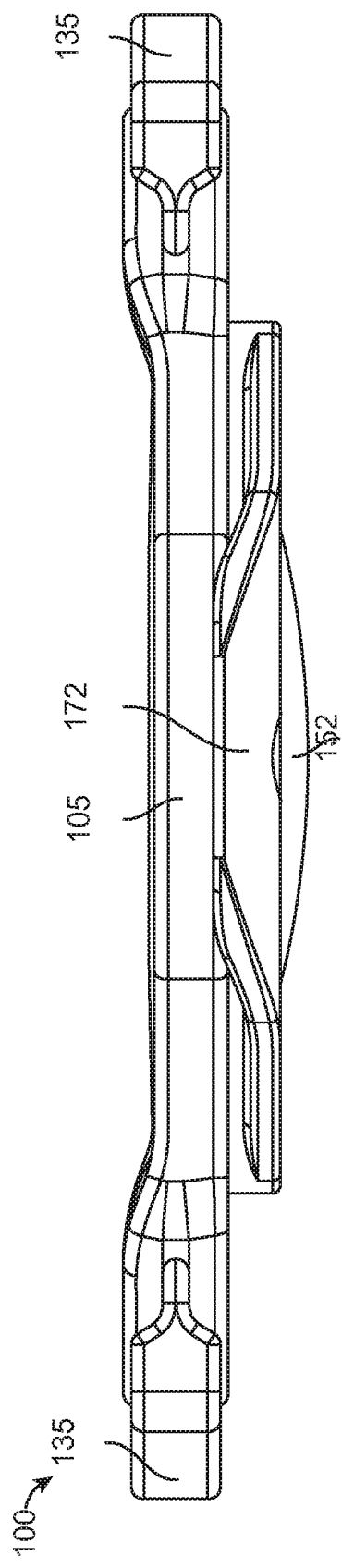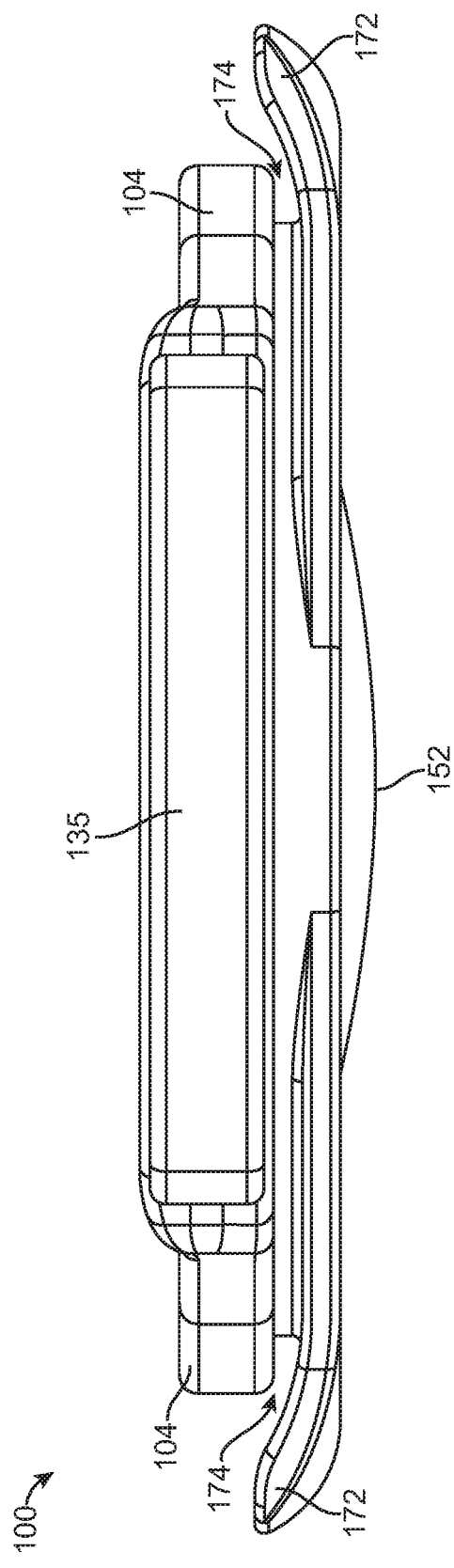

FLUOROSILICONE COPOLYMERS

CROSS-REFERENCES TO RELATED APPLICATIONS

This application is a Section 371 US National Phase of International Application No. PCT/US2020/026706 filed Apr. 3, 2020, which claims priority to U.S. Application No. 62/830,186 filed Apr. 5, 2019, which is incorporated herein by reference in its entirety and for all purposes.

BACKGROUND

A healthy, young human eye can focus an object in far or near distance, as required. The capability of the eye to change back and forth from near vision to far vision is called accommodation. Accommodation occurs when the ciliary muscle contracts to thereby release the resting zonular tension on the equatorial region of the capsular bag. The release of zonular tension allows the inherent elasticity of the lens to alter to a more globular or spherical shape, with increased surface curvatures of both the anterior and posterior lenticular surfaces.

The human eye 10 includes a cornea 12, iris 14, sulcus 16, ciliary muscle 18, zonules 20, a lens 21 contained within a capsular bag 22 (FIGS. 1A and 1C). Accommodation occurs when the ciliary muscle 18 contracts to thereby release the resting zonular tension on the equatorial region of the capsular bag 22. The release of zonular tension allows the inherent elasticity of the lens 21 to alter to a more globular or spherical shape, with increased surface curvatures of both the anterior lenticular surface 23 and posterior lenticular surface 24. In addition, the human lens can be afflicted with one or more disorders that degrade its functioning in the vision system. A common lens disorder is a cataract which consists of the opacification of the normally clear, natural crystalline lens matrix 26. The opacification can result from the aging process but can also be caused by heredity, diabetes, or trauma. FIG. TA shows a lens capsule comprising a capsular bag 22 with an opacified, crystalline lens nucleus 26.

In a cataract procedure, the patient's opaque crystalline lens is replaced with a clear lens implant or intraocular lens (IOL) 30. In conventional extracapsular cataract surgery as depicted in FIG. 1B, the crystalline lens matrix 26 is removed leaving intact the thin walls of the anterior and posterior capsules together with zonular ligament connections to the ciliary body and ciliary muscles 18. The crystalline lens core is removed by phacoemulsification through a curvilinear capsulorhexis as illustrated in FIG. 1B, i.e., the removal of an anterior portion 23 of the capsular sac. FIG. 1B depicts a conventional 3-piece IOL 30 just after implantation in the capsular bag 22.

It is known to implant a combination of lenses to address refraction errors in the existing lens in the case of phakic IOLs or improve the refractive results of standard IOL after cataract surgery in the case of pseudophakic patients. These "piggyback" IOLs can be placed anterior to the previously implanted IOL or natural lens to improve the refractive results of cataract surgery in the case of pseudophakes or to change the refractive status of the eye in the case of phakic eyes, usually to correct high myopia. Generally, these lenses are implanted in the ciliary sulcus and are non-accommodating. As shown in FIG. 1C, the ciliary sulcus 16 is the space between the posterior surface of the base of the iris 14 and the anterior surface of the ciliary body.

Accommodating IOLs are beneficial for patients not suffering from cataracts, but who wish to reduce their dependency on glasses and contacts to correct their myopia, hyperopia and presbyopia. Intraocular lenses used to correct large errors in myopic, hyperopic, and astigmatic eye are called "phakic intraocular lenses" and are implanted without removing the crystalline lens. In some cases, aphakic IOLs (not phakic IOLs) are implanted via lens extraction and replacement surgery even if no cataract exists. During this surgery, the crystalline lens is extracted and an IOL replaces it in a process that is very similar to cataract surgery. Refractive lens exchange, like cataract surgery, involves lens replacement, requires making a small incision in the eye for lens insertion, use of local anesthesia and lasts approximately 30 minutes.

IOLs, particularly accommodating IOLs, may incorporate liquids in fluid chambers such that accommodation is achieved with the help of fluid-actuated mechanisms. A force exerted on a portion of the lens is transmitted via the fluid to deform a flexible layer of the lens resulting in accommodative shape change of the IOL. There is need in the art for improved liquids that can be used in conjunction with IOLs that provide improved properties for patients in need. The disclosure is directed to this, as well as other, important ends.

BRIEF SUMMARY

The disclosure provides a copolymer of Formula (A)

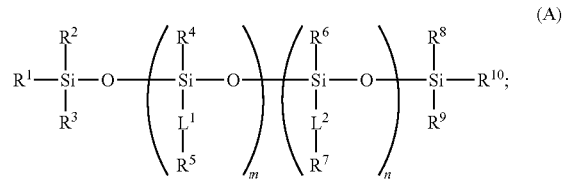

wherein the substituents are as defined herein. The disclosure provides compositions comprising the copolymer of Formula (A), lenses (e.g., intraocular lenses) comprising the copolymer of Formula (A), and processes for preparing the copolymer of Formula (A).

The disclosure provides a copolymer of Formula (B):

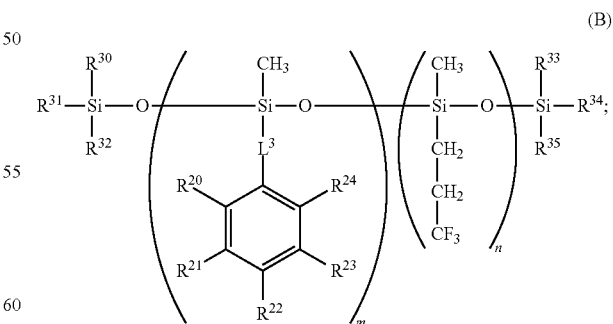

wherein the substituents are as defined herein. The disclosure provides compositions comprising the copolymer of Formula (B), lenses (e.g., intraocular lenses) comprising the copolymer of Formula (B), and processes for preparing the copolymer of Formula (A).

These and other embodiments and aspects of the disclosure are described in detail herein.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements is modified for the purpose of illustrative clarity.

FIG. 1A is a perspective cut-away view of an eye with an opacified lens capsule; FIG. 1B is a perspective cut-away view of the eye of FIG. 1A with a curvilinear capsulorhexis and the crystalline lens matrix removed with the implantation of a traditional 3-piece IOL; and FIG. 1C is a cross-sectional view of an anterior angle of an eye;

FIG. 2A shows that increasing the phenyl content of silicone oil increases its RI; FIG. 2B shows that increasing the fluoro content of silicone oil decreases its RI; and FIG. 2C shows that increasing the fluoro content of benzene-based molecules decreases its RI;

FIG. 3A shows a lens body in schematic illustrating a liquid optical material contained within a fluid chamber of a solid optical component; FIG. 3B shows the lens body of FIG. 3A in which the liquid optical material swelled due to absorption of aqueous increasing the volume of the fluid chamber and the power of the lens body; and FIG. 3C shows the lens body of FIG. 3A in which the liquid optical material has migrated out of the fluid chamber decreasing the volume of the fluid chamber and the power of the lens body;

FIGS. 4A-4F are perspectives of an intraocular lens. 4A illustrates a perspective view of an implementation of an accommodating intraocular lens device; FIG. 4B is a cross-sectional view taken along line B-B of FIG. 4A; FIG. 4C is a cross-sectional view taken along line C-C of FIG. 4A; FIG. 4D is the internal support and stabilization system of the device of FIG. 4A; and FIGS. 4E-4F are side views of the device of FIG. 4A;

FIG. 5A illustrates a perspective view of an implementation of an accommodating intraocular lens device; FIG. 5B is a cross-sectional view taken along line B-B of FIG. 5A; FIG. 5C is a cross-sectional view taken along line C-C of FIG. 5A; FIG. 5D is the internal support of the device of FIG. 5A; and FIGS. 5E-5F are side views of the device of FIG. 5A.

FIG. 6A illustrates a perspective view of an implementation of a lens; FIG. 6B is a side view of the lens of FIG. 6A; and FIG. 6C is a posterior perspective view of the lens of FIG. 6A.

It should be appreciated that the drawings herein are exemplary only and are not meant to be to scale.

DETAILED DESCRIPTION

It is important to have quality optics in lenses, particularly intraocular lenses (IOL), that avoid stray light, glare, or unintended reflections that reach the retina. Generally, lenses allow light that is refracted by the optically designed lens surfaces to reach the retina. Light from the edge of a lens at the non-optical interface between the lens edge and the aqueous humor can cause dysphotapsias common in commercial lenses known in the art known. Dysphotopsias can be an annoyance to patients. Similarly, any interface between two materials of varying refractive index within the lens may cause light to reach a patient's retina in a way that disturbs clear, quality vision. Accommodating IOLs, in particular, may have additional internal structures (as described herein) and therefore benefit from having all index-matched materials. The index-matched materials reduce undesired reflections from optical interfaces within the lens.

Maintaining a predictable shape of the lens throughout its useful life provides the correct optical power to properly focus light onto a patient's retina. Lenses known in the art can incorporate liquids in fluid chambers. For example, some lenses incorporate liquids configured to aid accommodation and deforming a flexible layer of the lens. Hygroscopic liquids can absorb water, for example, from the surrounding aqueous humor that can cause the lens to expand beyond the desired volume and pressure. Inadvertent expansion can increase the curvature of the lens surfaces causing them to be more convex and providing excess optical power to the patient. Alternatively, liquids in the fluid chamber can seep out of the fluid chamber. For example, silicone oil contained within a fluid chamber of a lens that is formed of a chemically similar silicone elastomer like polydimethylsiloxane (PDMS) can suffer from instability due to the miscibility of the silicone oil and silicone elastomer. The oil tends to enter into the silicone elastomer causing an unintended optical power change in the lens. The surface curvatures of the lens body would decrease (less convex or more concave) thereby reducing the power of the lens and providing insufficient optical power to the patient. This also reduces the ability of the lens to undergo sufficient shape change when necessary at the time of accommodation. Even minor changes of the internal pressure can result in substantial undesirable changes to the optical power of the lens.

Figure 3A:
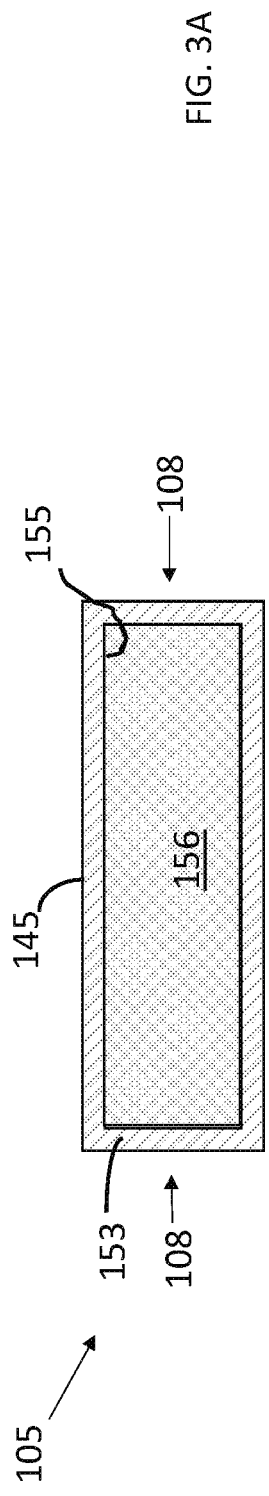
FIGS. 3A-3C show a lens body.
Figure 3B:
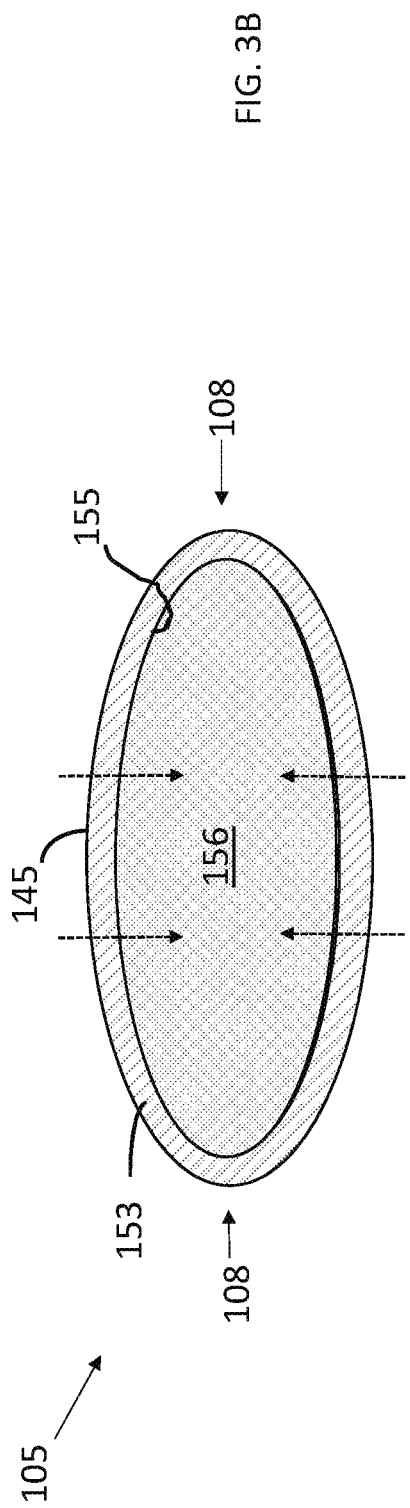
Figure 3C:
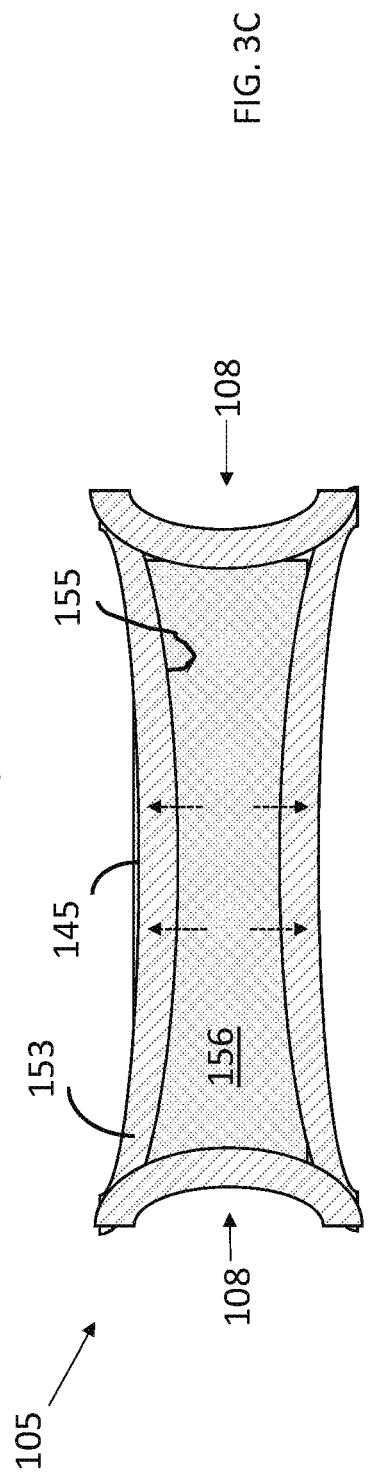

FIGS. 3A-3C show in schematic a lens body 105 having a liquid optical material 156 contained within a sealed, fixed volume fluid chamber 155 defined by a solid optical component 153. In aspects, the lens body 105 can include an anterior optic 145 and at least a portion of the anterior optic 145 is configured to undergo a shape change to alter the power of the lens. For example, compression of an equator region 108 of the lens body 105 can deform the liquid optical material 156 and the fluid chamber 155 to cause the anterior optic 145 to bow outward increasing the curvature and the power of the lens. FIG. 3A shows the lens body 105 where the liquid optical material 156 and the solid optical component 153 are in a resting shape. FIG. 3B shows the absorption of aqueous from the surrounding environment into the liquid optical material 156 thereby increasing the volume of the fluid chamber 155 and changing the resting shape of the lens body 105 to be more curved. FIG. 3C shows the lens body of FIG. 3A in which the liquid optical material 156 has migrated out of the fluid chamber 155 into the surrounding solid optical component 153 thereby decreasing the volume of the fluid chamber and changing the resting shape of the lens body 105 to be less curved or convex. The shape changes of the lens body 105 due to entry or exit of the liquid optical material 156 from the fluid chamber 155 affects the power of the lens body 105. The lens body 105 is provided in schematic to illustrate the liquid optical materials described herein can be used in combination with solid optical components having any of a variety of configurations. Reference to a lens or an intraocular lens (IOL) herein is not intended to be limited to any particular lens configuration.

The liquid optical materials and solid optical components of the lens can have substantially the same refractive index, but are sufficiently chemically dissimilar such that the liquid optical materials and solid optical components of the lens are immiscible. The liquid optical materials described herein can be specially formulated optical oils that in combination with the solid optical components of the lens minimize internal reflections and provide stable optical power over the life of the lens. It should be appreciated that the liquid optical materials described herein can be used with any of a variety of lenses. Thus, configuration of the lens and whether and how accommodation in the lens is achieved can vary. The liquid optical materials described herein can be part of a lens device that is configured to change shape and provide accommodation. The liquid optical materials described herein can be part of a lens device that is not configured to change shape. The liquid optical materials described herein can be used with monofocal or multifocal lenses. The liquid optical materials described herein can be used with lenses that are not configured to be implanted in an eye. For example, the liquid optical materials can be incorporated into an eyeglass lens, contact lens, camera lens, imagining lens, microscope lens, telescope lens, monocular lens, binocular lens, projector lens, spotting scope lens, telescopic gun sight lens, theodolite lens, and medical equipment lens.

The liquid optical material within the lens body and the solid optical component containing the liquid optical material can both be optically clear, biocompatible polymer formulations preferably silicone formulations. Silicone is a generic term used to describe polymer structures with the basic $(Si-O)_n$ backbone. Silicones of varying chemical, optical, rheological, and mechanical properties can be generated by manipulating the R group extending from the silicon atoms along the polymer chain. In aspects, the R group is uniformly one functional group, as is the case with polydimethyl or polydiphenyl silicone. In aspects, the polymer has varying functional groups to provide specific material properties. The functional groups may vary in an orderly fashion such as a block copolymer or an alternating copolymer, alternatively the functional groups is arranged in a random fashion. The functional groups is single molecular entities, such as a methyl or phenyl group. In aspects, the functional group is a polymer unto itself, creating an extended chain that extends from the silicone backbone. In aspects, the functional group forms a bond between multiple silicone chains, i.e., cross-linked, thus creating a bound polymer network. These cross-linked silicones can take the form of silicone rubbers or silicone gels, which behave partially or completely like solids.

The liquid optical material of the lens body that is contained within the fluid chamber can have an index of refraction that is substantially matched to the index of refraction of the solid optical component forming the chamber, but chemically independent. For example, the liquid optical material can have solubility properties that prevent the liquid optical material from migrating out of the fluid chamber into the surrounding material of the lens body components or solid optical component. As described herein, the liquid optical material and the material of the solid optical component can have similar chemical properties, but differing solubilities such that the liquid optical material does not penetrate the solid lens body components. The solid elastomeric component of the lens body forming the fluid chamber can vary, but generally includes any solid optical component that is positioned at least in part within the optic zone of the lens and is configured to contain or come into contact with the liquid optical material.

"Component" as used herein can include a single component or a plurality of components operatively coupled to perform one or more functions. As used herein "optical component" is a component that is clear and transparent in the visible spectrum such that it can be present within the visual axis of the eye without hindering vision. "Index-matching" as used herein refers to minimizing the optical interface between two materials and "substantially the same" refractive index refers to indices of refraction that, even though is slightly different, are intended to be as close as possible to minimize the difference in refractive index.

The optical properties and solubility of both the liquid and solid silicone materials of the lens are significantly determined by the nature of the functional groups attached to the silicone backbone. For example, if the solid optical components are formed of polydiphenyl silicone elastomer and the liquid optical material is polydiphenyl silicone oil, the materials are index-matched and internal reflections are minimized. However, the polydiphenyl silicone oil will over time penetrate the silicone elastomer causing instability in lens power. Alternatively, the solid optical components can be formed of polydiphenyl silicone elastomer and the liquid optical material can be fluorosilicone oil or the solid components can be formed of fluorosilicone elastomer and the liquid optical material can be polydiphenyl silicone oil. The chemically independent materials substantially stabilizes the lens power because the oil is insoluble in the elastomer, however, their refractive indices are different enough to cause internal reflections within the lens and undesirable optical side-effects.

As described herein, the liquid/solid combinations are substantially chemically insoluble with one another providing stable internal volumes and pressure to the lens. The liquid optical material filling the solid elastomeric materials provides a stable internal pressure driving the shape of the lens body that can remain substantially constant throughout the life of the lens.

"Liquid optical material" refers to a material or composition that is clear and transparent in the visible spectrum such that it can be present within the visual axis of the eye without hindering vision. In aspects, a liquid optical material is a composition comprising a silicone oil. In aspects, a liquid optical material is a composition comprising a fluorosilicone oil. In aspects, the liquid optical material comprises a polymer or copolymer as described herein (e.g., a compound of Formula (A), a compound of Formula (B), a compound of Formula (I), or a compound of any one of Formula (VIII), (IX), and (X)). In aspects, the liquid optical material comprises a plurality of polymers or copolymers as described herein (e.g., a plurality of the compound of Formula (A), a plurality of the compound of Formula (B), a compound of Formula (I), or a compound of any one of Formula (VIII), (IX), and (X)). In aspects, In aspects, the liquid optical material comprises a plurality of polymers or copolymers (e.g., a plurality of the compound of Formula (A), a plurality of the compound of Formula (B), a compound of Formula (I), or a compound of any one of Formula (VIII), (IX), and (X), and one or more impurities.

The abbreviations used herein have their conventional meaning within the chemical and biological arts. The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., $-CH_2O-$ is equivalent to $-OCH_2-$.

"Silicone elastomer" refers to a rubber-like material comprising the polysiloxane structure:

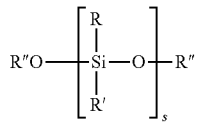

wherein R and R' are alkyl, alkenyl, or aryl; R" is hydrogen, alkyl, or —Si(R)$_3$; and s is an integer from 1 to 5,000. These polysiloxane chains may be cross-linked to form a polymer network, imparting elastic properties on the bulk material. Exemplary silicone elastomers include dimethyl silicone elastomers, diphenyl silicone elastomers, copolymers of polydimethyl and polydiphenyl siloxane, polyfluorosilicone elastomers, or silicone elastomers with alkane and/or aromatic functionality. In aspects, the silicone elastomer contains about 25% or more of dimethylsiloxone. In aspects, the silicone elastomer contains more than 50% dimethylsiloxone. In aspects, the silicone elastomer contains more than 60% dimethylsiloxone. In aspects, the silicone elastomer contains more than 70% dimethylsiloxone. In aspects, the silicone elastomer contains more than 80% dimethylsiloxone. In aspects, the silicone elastomer contains more than 90% dimethylsiloxone. In aspects, the silicone elastomer contains more than 95% dimethylsiloxone. In aspects, the silicone elastomer contains more than 99% dimethylsiloxone. In aspects, the silicone elastomer is polydimethylsiloxane (PDMS). In aspects, the silicone elastomer is a dimethyl methylvinyl siloxane. Other silicone elastomers are known in the art and would be readily apparent to the skilled artisan. For example, the skilled artisan would readily recognize that the backbone length and/or crosslink density and/or functionalization of the silicone elastomer can be modified to create a silicone elatomer having the mechanical and/or optical and/or chemical properties necessary for the intended purpose.

The term "alkyl," by itself or as part of another substituent, means, unless otherwise stated, a straight (i.e., unbranched) or branched carbon chain (or carbon), or combination thereof, which is fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety is an alkenyl moiety. An alkyl moiety is an alkynyl moiety. An alkyl moiety is fully saturated. An alkenyl may include more than one double bond and/or one or more triple bonds in addition to the one or more double bonds. An alkynyl may include more than one triple bond and/or one or more double bonds in addition to the one or more triple bonds. In aspects, the term "alkyl" refers to a straight or branched hydrocarbon chain radical consisting solely of carbon and hydrogen atoms, which may be saturated or unsaturated (i.e., contains one or more double and/or triple bonds), having from one to twenty carbon atoms ($C_1$-$C_{20}$ alkyl), and which may be attached to the rest of the molecule by a single bond. Suitable alkyl groups may include, but are not limited to, methyl, ethyl, n-propyl, i-propyl, n-butyl, t-butyl, n-pentyl, n-hexyl, n-heptyl, n-octyl, etc.

The term "alkylene," by itself or as part of another substituent, means, unless otherwise stated, a divalent radical derived from an alkyl, as exemplified, but not limited by, —CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. In aspects, the term "alkenyl" refers to a linear or branched hydrocarbon radical having from one to twenty carbon atoms, and containing at least one double bond. Suitable alkenyl groups may include, but are not limited to, vinyl, 2-propenyl, crotyl, 2-isopentenyl, etc The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) is placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —S—CH$_2$—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms is consecutive, such as, for example, —CH$_2$—NH—OCH$_3$ and —CH$_2$—O—Si(CH$_3$)$_3$. A heteroalkyl moiety may include one heteroatom. A heteroalkyl moiety may include two optionally different heteroatoms. A heteroalkyl moiety may include three optionally different heteroatoms). A heteroalkyl moiety may include four optionally different heteroatoms. A heteroalkyl moiety may include five optionally different heteroatoms. A heteroalkyl moiety may include up to 8 optionally different heteroatoms. The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Terms such as "haloalkyl" are meant to include monohaloalkyl and polyhaloalkyl. For example, "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent is —O— bonded to a ring heteroatom nitrogen. In aspects, the term "aryl" may refer to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene Spirocyclic rings are two or more rings wherein adjacent rings are attached through a single atom. The individual rings within spirocyclic rings is identical or different. Individual rings in spirocyclic rings is substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings is substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group is any of the immediately previous list, including having all rings of one type (e.g., all rings being substituted heterocycloalkylene wherein each ring is the same or different substituted heterocycloalkylene). When referring to a spirocyclic ring system, heterocyclic spirocyclic rings means a spirocyclic rings wherein at least one ring is a heterocyclic ring and wherein each ring is a different ring. When referring to a spirocyclic ring system, substituted spirocyclic rings means that at least one ring is substituted and each substituent may optionally be different.

The symbol "〰" or "—" denotes the point of attachment of a chemical moiety to the remainder of a molecule or chemical formula.

The term "oxo" means an oxygen that is double bonded to a carbon atom.

The term "alkylarylene" as an arylene moiety covalently bonded to an alkylene moiety (also referred to herein as an alkylene linker). An alkylarylene moiety is substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_8$ alkyl or substituted or unsubstituted 2 to 5 membered heteroalkyl). In aspects, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR''' R"", —CN, —NO$_2$, —NR'SO$_2$R", —NR'C(O)R", —NR'C(O)—OR", —NR'OR", in a number ranging from zero to (2 m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", —NR'C(O)NR"NR''' R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R"" groups when more than one of these groups is present.

Substituents for rings (e.g., cycloalkyl, heterocycloalkyl, aryl, heteroaryl, cycloalkylene, heterocycloalkylene, arylene, or heteroarylene) is depicted as substituents on the ring rather than on a specific atom of a ring (commonly referred to as a floating substituent). In such a case, the substituent is attached to any of the ring atoms (obeying the rules of chemical valency) and in the case of fused rings or spirocyclic rings, a substituent depicted as associated with one member of the fused rings or spirocyclic rings (a floating substituent on a single ring), is a substituent on any of the fused rings or spirocyclic rings (a floating substituent on multiple rings). When a substituent is attached to a ring, but not a specific atom (a floating substituent), and a subscript for the substituent is an integer greater than one, the multiple substituents is on the same atom, same ring, different atoms, different fused rings, different spirocyclic rings, and each substituent may optionally be different. Where a point of attachment of a ring to the remainder of a molecule is not limited to a single atom (a floating substituent), the attachment point is any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents is bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In aspects, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In aspects, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), selenium (Se), and silicon (Si). In aspects, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In aspects, each substituted group described in the compounds herein is substituted with at least one substituent group. More specifically, in aspects, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In aspects, at least one or all of these groups are substituted with at least one lower substituent group.

In aspects of the compounds herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In aspects of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In aspects, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In aspects, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In aspects, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In aspects, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In aspects, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In aspects, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In aspects, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that is defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The disclosure is meant to include compounds in racemic and optically pure forms. Optically active (R)- and (S)- or (D)- and (L)-isomers is prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "isomers" refers to compounds having the same number and kind of atoms, and hence the same molecular weight, but differing in respect to the structural arrangement or configuration of the atoms. The term "tautomer," as used herein, refers to one of two or more structural isomers which exist in equilibrium and which are readily converted from one isomeric form to another. It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure. The compounds of the present disclosure may also contain unnatural proportions of atomic isotopes at one or more of the atoms that constitute such compounds. For example, the compounds is radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue," or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group is substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group is referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol is used to distinguish each appearance of that particular R group. For example, where multiple $R^{13}$ substituents are present, each $R^{13}$ substituent is distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group is substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The phrase "average molecular weight" and "number average molecular weight" refer to the number average molecular weight of a polymer as determined, e.g., by gel permeation chromatography (also known as GPC or size exclusion chromatography (SEC)).

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

IOLs are preferably formed of materials configured for small incision implantation. The solid optical component of the lens can have elastomeric characteristics and can be made of soft silicone polymers that are optically clear, biocompatible, and in certain circumstances flexible having a sufficiently low Young's modulus to allow for the lens body to change its degree of curvature during accommodation. It should be appreciated that some solid optical components have a different Young's modulus than other solid optical components to provide different function to the lens (e.g. outward bowing of an anterior lens element during accommodation compared to immovable internal support mitigating distortion during accommodation).

Suitable materials for the solid optical component of the lens body can include, but are not limited to silicone (e.g., alkyl siloxanes, phenyl siloxanes, fluorinated siloxanes, combinations/copolymers thereof), acrylic (e.g., alkyl acrylates, fluoroacrylates, phenyl acrylate, combinations/copolymers thereof), urethanes, elastomers, plastics, combinations thereof, etc. In aspects, the solid optical component of the lens body is formed of a silicone elastomer, as described herein.

The solid optical component can be formed of one or a combination of the materials described herein in which the liquid optical material described herein is fully encapsulated by the solid optical component. The solid optical component of a lens body may include one or more regions that are configured to be in contact with and/or contain the liquid optical material. The liquid optical materials described herein are specially formulated relative to the material of the solid optical component to mitigate lens instability and optimize optical quality. The liquid optical materials can include biocompatible, non-compressible materials that are entirely liquid such as liquids and oils as well as materials that are mostly liquid such as gels.

The solid optical component is formed of a silicone elastomer as described herein. A liquid optical material that also has substantial hydrocarbon functionality can chemically interact with a silicone elastomer having hydrocarbon functionality. Thus, where both the solid optical component and the liquid optical material are formed of a dimethyl or diphenyl silicone elastomer, the liquid optical material can have at least some non-hydrocarbon functionality, for example, fluorine functionality.

Suitable liquid optical materials include, for example, a silicone polymers and silicone copolymers. The silicone polymer may include functionalized silicone liquids such as fluorinated silicones, aromatic, i.e., phenyl functionalized silicone, etc., hydrocarbon and functionalized hydrocarbons, such as long chain hydrocarbons, halogenated hydrocarbons, such as fluorinated and partially fluorinated hydrocarbons, aqueous systems, whose refractive index (RI) has been increased by the additions of water-soluble or water swellable polymers, bio-polymer swellable additives such as cellulose, as well as organic or inorganic additives that form nanostructures to increase refractive index. In aspects, the silicone polymer is a fluorosilicone polymer, fluoro-methyl, difluoro methyl, perfluoromethyl, fluorophenyl, difluorophenyl, trifluorophenyl, tetrafluorophenyl, perfluorophenyl, or other fluorine-based oil that includes partially or fully fluorinated ethyl, propyl, butyl, or other alkane-based chains, partial or fully fluorinated allyl, alkyl, naphthyl, or other fluorinated conjugated hydrocarbon. In aspects, the silicone polymer is a block copolymer, alternating copolymer, random copolymer of two, three, four, or more unique functional groups oriented along the silicone backbone. In aspects, the silicone polymer is a homopolymer in which the repeat unit itself blends the fluorine and hydrocarbon functionality in the form of a partially or fully fluorinated phenyl or napthyl group. In aspects, the silicone polymer is a homopolymer in which each silicon group has a functional group attached that is itself a copolymer with both fluorinated and hydrocarbon functionality along the chain of the functional group. The silicone backbone can have any combination of the above in which fluorine-based functionality and hydrocarbon functionality is attached as copolymer long chains, single functional groups, or multifunctional molecules, as a random, block, or alternating copolymer. In aspects, the liquid optical material comprises aryl siloxane and an alkyl siloxane. Suitable aryl groups for the aryl siloxane include, but are not limited to, phenyl, naphthyl, toluyl, xylyl, and the like. Suitable alkyl groups include, but are not limited to, methyl, ethyl, n-propyl, i-propyl, n-butyl, t-butyl, n-pentyl, n-hexyl, and the like.

With respect to the copolymers described herein and the copolymers suitable for use an a liquid optical material, the ratio of the phenyl to fluoro content in the copolymers (e.g., the ratio of m:n for the copolymers of Formula (I), (A), (B), etc) can be adjusted or tuned such that the refractive index of the liquid optical material is substantially similar (i.e. "index-matched") to the solid optical component while still chemically dissimilar to thereby preventing lens body swelling or collapse due to migration of the liquid optical material from the chamber of the lens. "Tuning" as used herein can mean adding one or more functional groups (e.g., aryl, phenyl, fluorine) to a material to impact one or more of solubility or refractive index of the material. Chemical dissimilarity between the liquid and solid lens components prevents lens shape alterations due to volume/pressure changes within the lens body. Halo groups such as those containing fluorine can provide chemical dissimilarity relative to a non-halo containing material (e.g. PDMS of solid lens components). Fluorinated functional groups also lower the RI. Aromatic functional groups (e.g. phenyl) typically increase the RI. The aromatic functional groups have a greater effect on the RI than the solubility such that the RI of the halo-modified material can be tuned. Adding aromatic groups to the halo-modified material increase the RI to the RI of the surrounding lens components thereby providing both low solubility (non-miscible materials) and index matching. It should be appreciated that where the liquid optical material is described as having fluorinated functional groups to impact chemical nature relative to the solid lens components that other functional groups are considered herein including any of a variety of halo groups incorporating halogens (e.g., F, Cl, Br, and I). It should also be appreciated that where the liquid optical material is described as having phenyl functional groups to impact the chemical nature relative to the solid lens components that other aryl or aromatic functional groups are considered herein including any of a variety of aromatic functional groups (e.g., phenyl, naphthyl, toluyl, xylyl, and the like).

The liquid optical material can be a fluoro-containing silicone oil modified with one or more functional groups configured to increase refractive index. As described above, functional groups such as phenyl increase refractive index and functional groups such as fluoro decrease the refractive index.

Figure 1A:
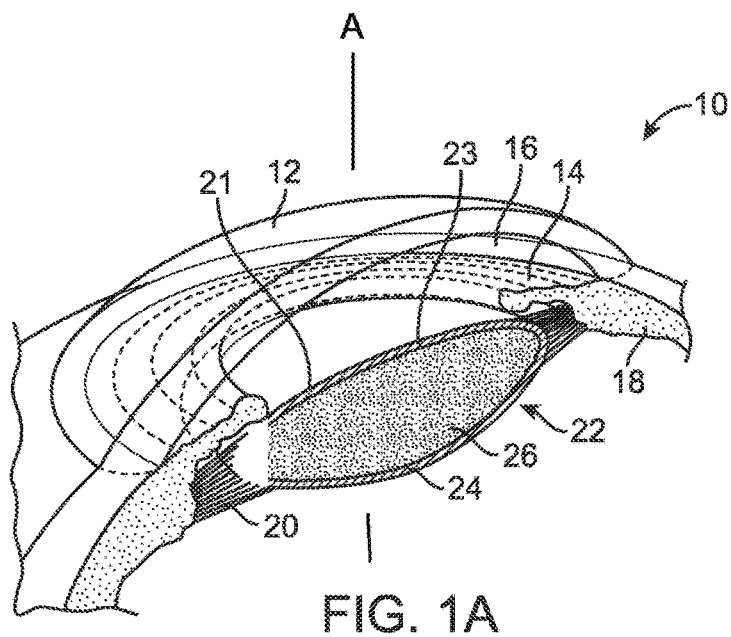
FIGS. 1A-1C are perspectives of an eye.
Figure 1B:
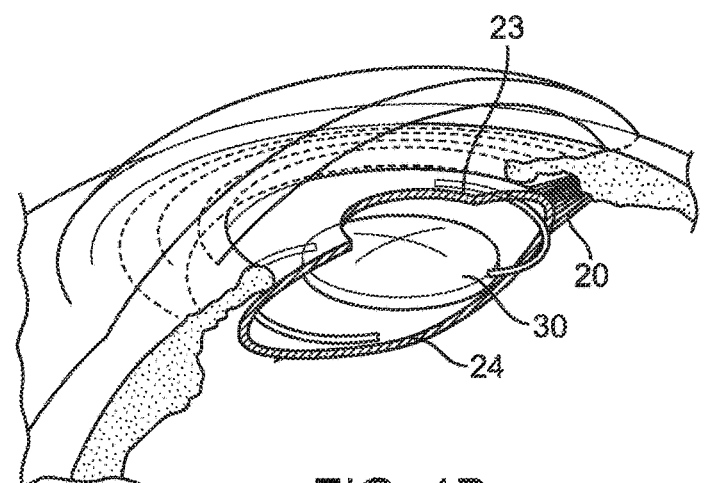
Figure 1C:
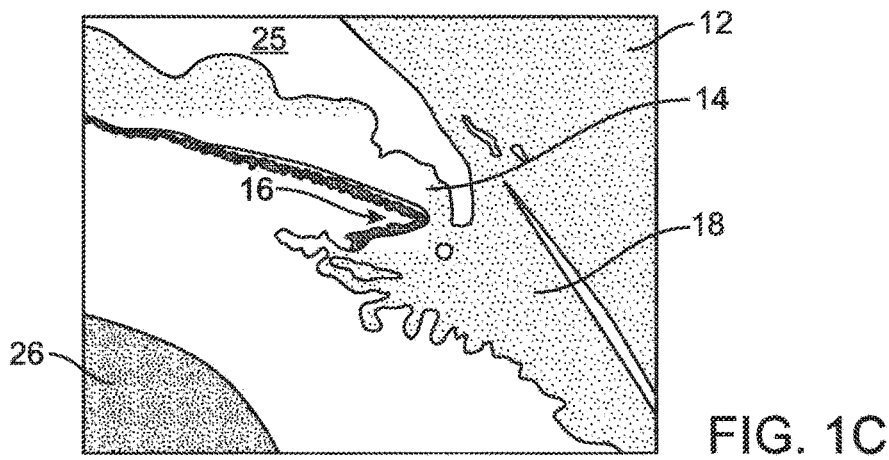
Figure 2A:
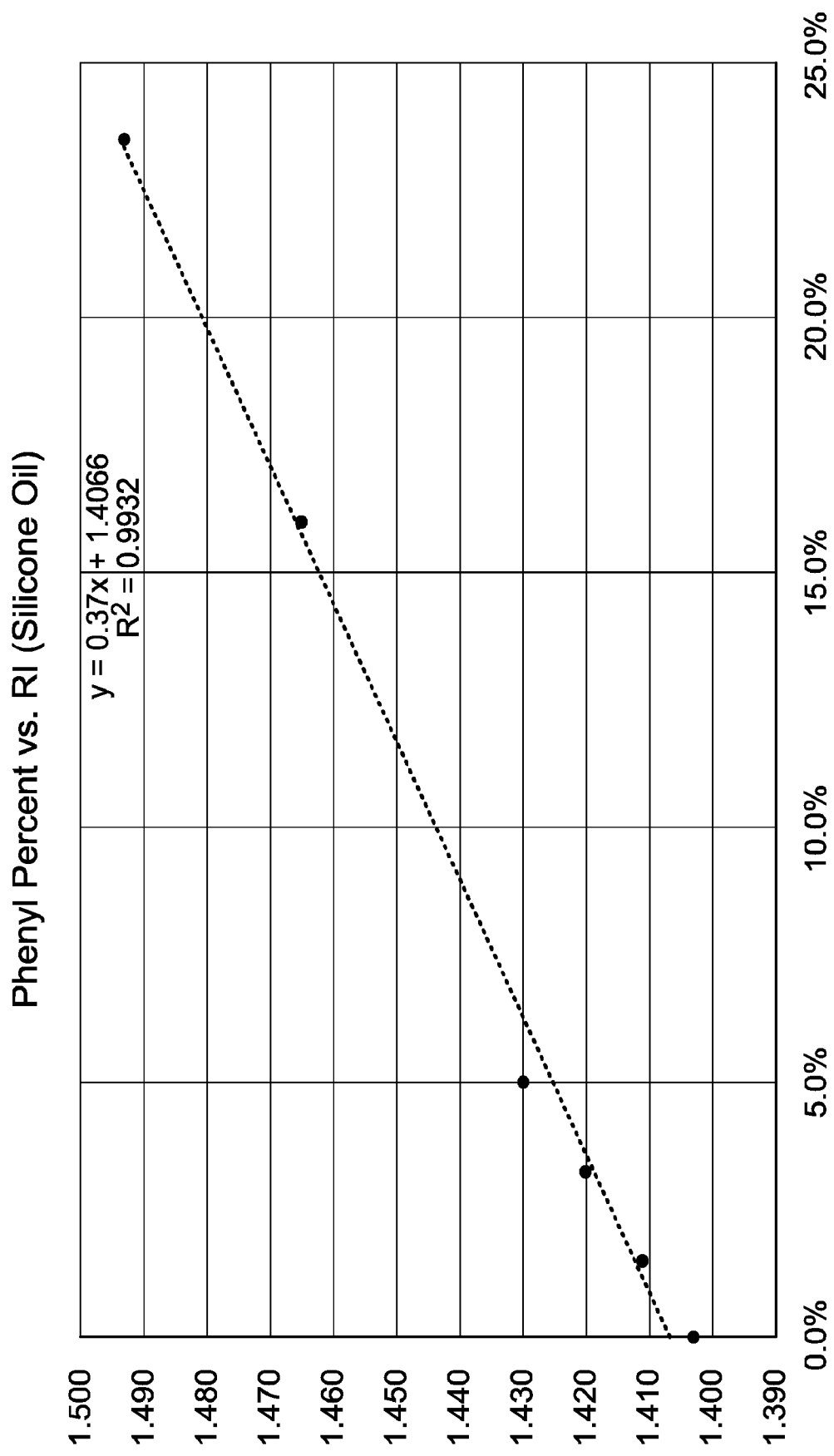
FIGS. 2A-2C are graphs showing the impact of certain compounds on refractive index (RI).
Figure 2B:
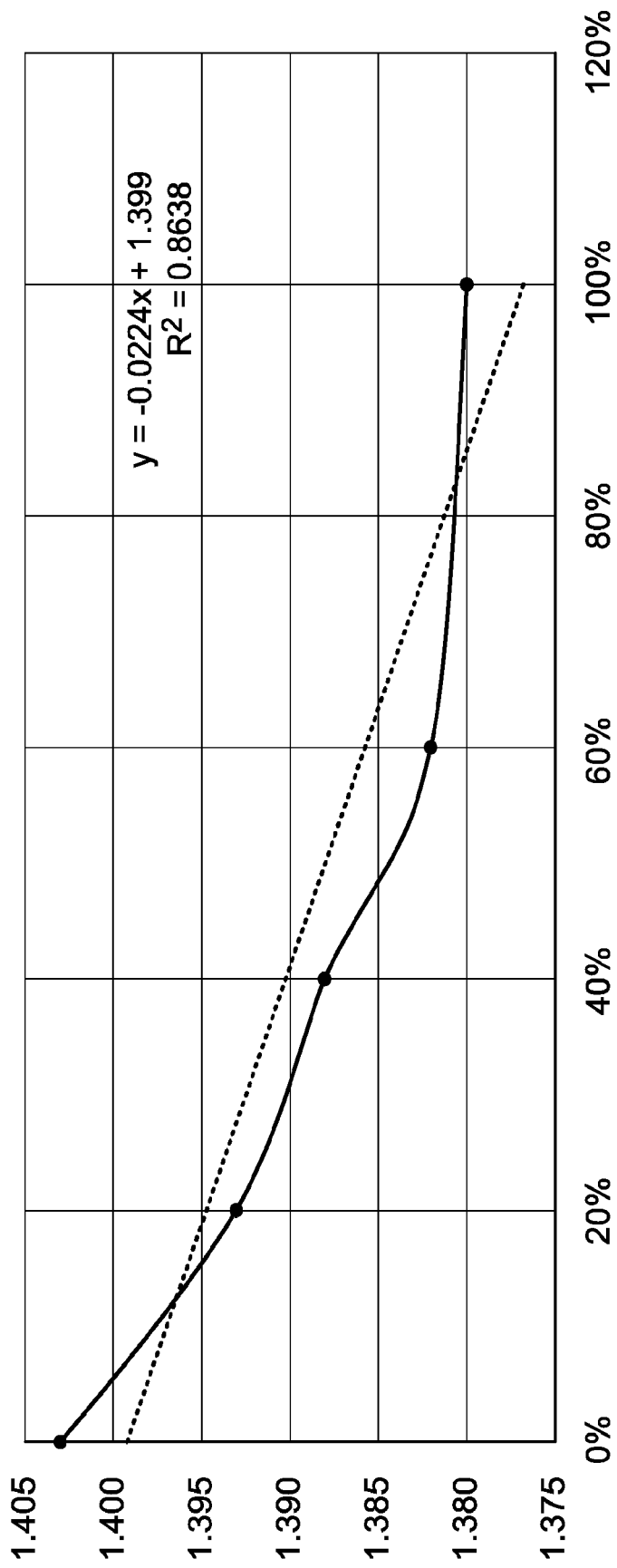
Figure 2C:
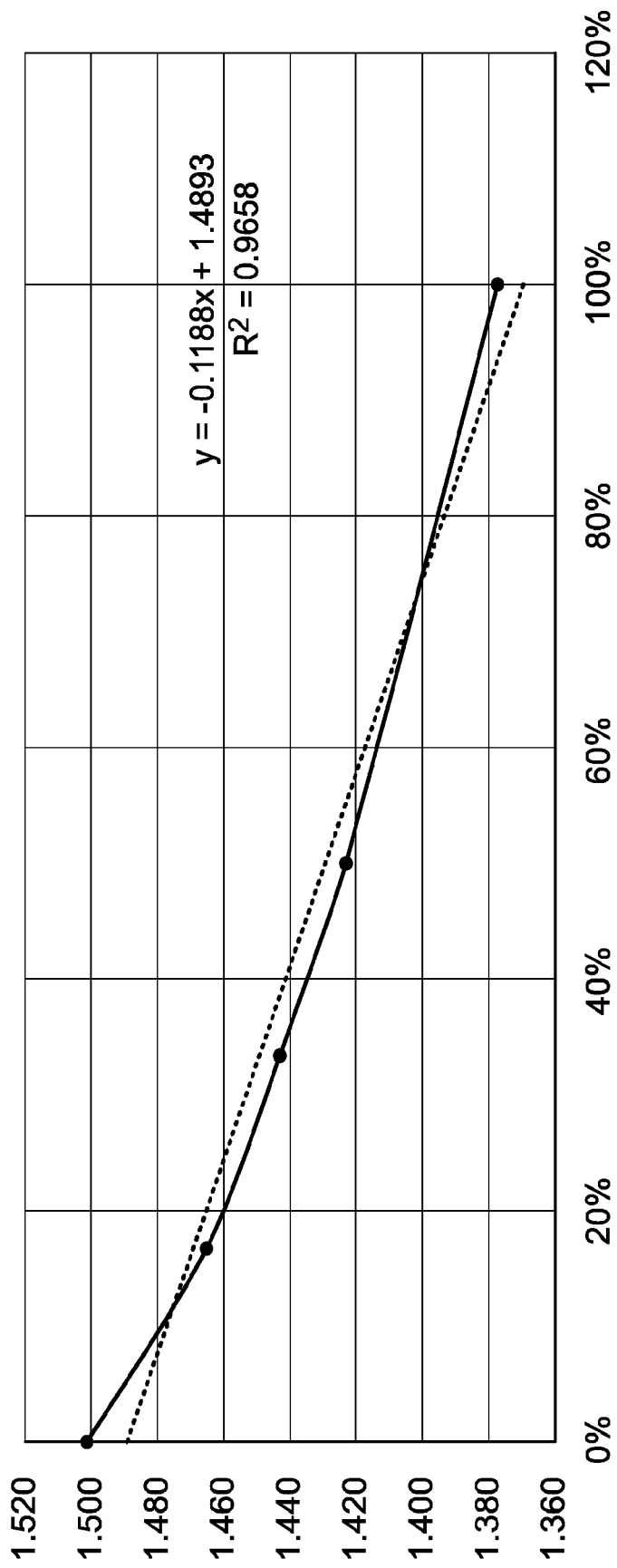

Listed below are various polymer products and their average percentages of phenyl content (Table 1) and fluoro content (Table 2) as well as their respective RIs compared to polydimethylsiloxane (PDMS). Increasing the phenyl content increases the refractive index (RI) (FIG. 2A) and increasing the fluoro content decreases the RI (FIG. 2B). Table 3 and FIG. 2C illustrate the effect fluoro content has on RI in benzene-based products. The fluoro percentage in Table 3 refers to the amount of fluorines bound to each benzene or toluene molecule as a percentage of the total available binding sites for fluorine.

TABLE 1

| Product ID | Phenyl Content | RI |
| --- | --- | --- |
| PDMS | 0.0% | 1.403 |
| PDV-0131 | 1.5% | 1.411 |
| PDV-0325 | 3.3% | 1.420 |
| PDV-0525 | 5.0% | 1.430 |
| PDV-1625 | 16.0% | 1.465 |
| PDV-2331 | 23.5% | 1.493 |

TABLE 2

| Product ID | Fluoro Content | RI |
| --- | --- | --- |
| PDMS | 0.0% | 1.403 |
| MED-420 | 20% | 1.393 |
| FMV-4035 | 40% | 1.388 |
| MED-460 | 60% | 1.382 |
| MED-400, FMS-H31 | 100% | 1.380 |

TABLE 3

| Functional Group | Fluoro Content | RI |
| --- | --- | --- |
| Benzene | 0% | 1.501 |
| Fluorobenzene | 17% | 1.465 |
| Difluorobenzene | 33% | 1.443 |
| Trifluorobenzene | 50% | 1.423 |
| Perfluorobenzene | 100% | 1.377 |

As an example, if the liquid optical material is for use with solid optical components formed of PDMS, the base polymer for the liquid optical material can have at least about 1.5% phenyl content. As shown in Table 1, that percentage of phenyl content drives up the refractive index (RI=1.411) away from the refractive index of PDMS (RI=1.403). In order to tune the liquid optical material back towards the refractive index of PDMS, the fluoro content of the material can be increased by adding functional groups such as shown in Tables 3 and 4. Alternatively, the base polymer for the liquid optical material can have at least about 20% fluoro content. As shown in Table 2 below, that percentage of fluoro content drives down the refractive index (RI=1.393) away from the refractive index of PDMS. The liquid optical material can be tuned back towards the refractive index of PDMS by adding aromatic functional groups (e.g. phenyl, naphthyl, etc.) that increase the refractive index until the liquid optical material is index-matched with the solid lens component material without significantly impacting the optical stability of the lens. The solid lens component material can be PDMS with some phenyl functionality and having a refractive index of 1.41, 1.43, 1.46 or in a range of between 1.41 up to about 1.50. The refractive index of the liquid optical materials can be tuned or titrated to this range of RI by adding the functional groups described herein.

In aspects, the disclosure provides a fluorosilicone copolymer of Formula (I):

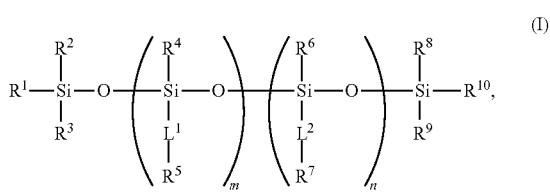

wherein n is an integer from 0 to about 500; m is an integer from 1 to about 500; $R^1$, $R^2$, $R^3$, $R^4$, $R^5$, $R^6$, $R^7$, $R^8$, $R^9$ and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein at least one of $R^1$, $R^2$, $R^3$, $R^4$, $R^5$, $R^6$, $R^7$, $R^8$, $R^9$ and $R^{10}$ are substituted with fluorine. In aspects, $R^1$, $R^2$, $R^3$, $R^4$, $R^5$, $R^6$, $R^7$, $R^8$, $R^9$ and $R^{10}$ are each independently hydrogen, substituted or unsubstituted alkyl, substituted or unsubstituted heteroalkyl, substituted or unsubstituted aryl, or substituted or unsubstituted heteroaryl, wherein at least one of $R^1$, $R^2$, $R^3$, $R^4$, $R^5$, $R^6$, $R^7$, $R^8$, $R^9$ and $R^{10}$ are substituted with fluorine. In aspects, $R^1$, $R^2$, $R^3$, $R^4$, $R^5$, $R^6$, $R^7$, $R^8$, $R^9$ and $R^{10}$ are each independently hydrogen, alkyl, alkenyl, or aryl, optionally substituted analogs thereof, or other suitable saturated or unsaturated functional group. In aspects, at least one of $R^4$, $R^5$, $R^6$, and $R^7$ are substituted with fluorine. n and m are integers designating a repeating siloxane unit, where n and m are independently selected to achieve a desired molecular weight of the resulting copolymer and/or selected to achieve a desired ratio of the particular siloxane polymer units to which n and m correspond. In aspects, m and n are both at least 1. The copolymers described herein can be random, block, or alternating. The copolymers can be linear or branched. In aspects, the copolymers are random and linear.

In embodiments, $R^1$ and/or $R^{10}$ is hydrogen. In aspects, $R^1$ and $R^{10}$ are independently alkyl or an optionally substituted alkyl. In aspects, $R^1$ and $R^{10}$ are independently aryl or an optionally substituted analog thereof. In aspects, $R^1$ and $R^{10}$ are independently alkenyl or an optionally substituted alkenyl. In aspects, $R^1$ and/or $R^{10}$ is a reactive functional group (e.g., an unsaturated alkenyl) configured to couple (e.g., via a crosslinking reaction) to a reactive group of another polymer, which may also comprise a copolymer of Formula (A). In aspects, $R^1$ and/or $R^{10}$ is vinyl, a reactive terminal end group other than vinyl, or a non-reactive group that does not participate in polymerization. In aspects, $R^1$ and/or $R^{10}$ include a methylhydrosiloxane-dimethylsilocane copolymer.

In embodiments, each of $R^2$, $R^3$, $R^8$, and $R^9$ is independently alkyl, aryl, or optionally substituted analogs thereof.

In aspects, each of $R^2$, $R^3$, $R^8$, and $R^9$ is independently alkyl or an optionally substituted alkyl. In aspects, each of $R^2$, $R^3$, $R^8$, and $R^9$ is methyl.

In embodiments, $R^4$ and $R^5$ are independently alky, aryl, or optionally substituted analogs thereof. In aspects, $R^4$ and $R^5$ are independently alkyl or an optionally substituted alkyl. In aspects, $R^4$ and/or $R^5$ is methyl. In aspects, $R^6$ and $R^7$ are independently alky, aryl, or substituted analogs thereof. In aspects, $R^6$ and $R^7$ are independently aryl or an optionally substituted aryl. In aspects, $R^6$ and/or $R^7$ is phenyl. In aspects, $R^6$ is alkyl and $R^7$ is aryl. In aspect, $R^6$ is methyl and $R^7$ is phenyl.

In embodiments, $R^1$ and $R^{10}$ are vinyl; $R^2$, $R^3$, $R^4$, $R^5$, $R^8$, and $R^9$ are methyl; and $R^6$ and $R^7$ are phenyl. In aspects, $R^1$ and $R^{10}$ are vinyl; $R^2$, $R^3$, $R^4$, $R^5$, $R^6$, $R^8$, and $R^9$ are methyl; and $R^7$ is phenyl.

In aspects, $R^1$, $R^2$, $R^3$, $R^8$, $R^9$, and $R^{10}$ are each independently hydrogen, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In aspects, $R^1$ is hydrogen. In aspects, $R^1$ is unsubstituted $C_1$-$C_6$ alkyl. In aspects, $R^1$ is unsubstituted methyl. In aspects, $R^1$ is unsubstituted ethyl. In aspects, $R^1$ is unsubstituted propyl. In aspects, $R^1$ is unsubstituted butyl. In aspects, $R^1$ is $C_1$-$C_6$ alkyl substituted with at least one fluorine. In aspects, $R^1$ is methyl substituted with at least one fluorine. In aspects, $R^1$ is —$CF_3$. In aspects, $R^1$ is —$CHF_2$. In aspects, $R^1$ is —$CH_2F$. In aspects, $R^1$ is ethyl substituted with at least one fluorine. In aspects, $R^1$ is propyl substituted with at least one fluorine. In aspects, $R^1$ is butyl substituted with at least one fluorine. In aspects, $R^1$ is a substituted or unsubstituted alkenyl. In aspects, $R^1$ is a substituted or unsubstituted $C_2$-$C_6$ alkenyl. In aspects, $R^1$ is a substituted or unsubstituted vinyl.

In aspects, $R^2$ is hydrogen. In aspects, $R^2$ is unsubstituted $C_1$-$C_6$ alkyl. In aspects, $R^2$ is unsubstituted methyl. In aspects, $R^2$ is unsubstituted ethyl. In aspects, $R^2$ is unsubstituted propyl. In aspects, $R^2$ is unsubstituted butyl. In aspects, $R^2$ is $C_1$-$C_6$ alkyl substituted with at least one fluorine. In aspects, $R^2$ is methyl substituted with at least one fluorine. In aspects, $R^2$ is —$CF_3$. In aspects, $R^2$ is —$CHF_2$. In aspects, $R^2$ is —$CH_2F$. In aspects, $R^2$ is ethyl substituted with at least one fluorine. In aspects, $R^2$ is propyl substituted with at least one fluorine. In aspects, $R^2$ is butyl substituted with at least one fluorine. In aspects, $R^2$ is a substituted or unsubstituted alkenyl. In aspects, $R^2$ is a substituted or unsubstituted $C_2$-$C_6$ alkenyl. In aspects, $R^2$ is a substituted or unsubstituted vinyl.

In aspects, $R^3$ is hydrogen. In aspects, $R^3$ is unsubstituted $C_1$-$C_6$ alkyl. In aspects, $R^3$ is unsubstituted methyl. In aspects, $R^3$ is unsubstituted ethyl. In aspects, $R^3$ is unsubstituted propyl. In aspects, $R^3$ is unsubstituted butyl. In aspects, $R^3$ is $C_1$-$C_6$ alkyl substituted with at least one fluorine. In aspects, $R^3$ is methyl substituted with at least one fluorine. In aspects, $R^3$ is —$CF_3$. In aspects, $R^3$ is —$CHF_2$. In aspects, $R^3$ is —$CH_2F$. In aspects, $R^3$ is ethyl substituted with at least one fluorine. In aspects, $R^3$ is propyl substituted with at least one fluorine. In aspects, $R^3$ is butyl substituted with at least one fluorine. In aspects, $R^3$ is a substituted or unsubstituted alkenyl. In aspects, $R^3$ is a substituted or unsubstituted $C_2$-$C_6$ alkenyl. In aspects, $R^3$ is a substituted or unsubstituted vinyl.

In aspects, $R^8$ is hydrogen. In aspects, $R^8$ is unsubstituted $C_1$-$C_6$ alkyl. In aspects, $R^8$ is unsubstituted methyl. In aspects, $R^8$ is unsubstituted ethyl. In aspects, $R^8$ is unsubstituted propyl. In aspects, $R^8$ is unsubstituted butyl. In aspects, $R^8$ is $C_1$-$C_6$ alkyl substituted with at least one fluorine. In aspects, $R^8$ is methyl substituted with at least one fluorine. In aspects, $R^8$ is —$CF_3$. In aspects, $R^8$ is —$CHF_2$. In aspects, $R^8$ is —$CH_2F$. In aspects, $R^8$ is ethyl substituted with at least one fluorine. In aspects, $R^8$ is propyl substituted with at least one fluorine. In aspects, $R^8$ is butyl substituted with at least one fluorine. In aspects, $R^8$ is a substituted or unsubstituted alkenyl. In aspects, $R^8$ is a substituted or unsubstituted $C_2$-$C_6$ alkenyl. In aspects, $R^8$ is a substituted or unsubstituted vinyl.

In aspects, $R^9$ is hydrogen. In aspects, $R^9$ is unsubstituted $C_1$-$C_6$ alkyl. In aspects, $R^9$ is unsubstituted methyl. In aspects, $R^9$ is unsubstituted ethyl. In aspects, $R^9$ is unsubstituted propyl. In aspects, $R^9$ is unsubstituted butyl. In aspects, $R^9$ is $C_1$-$C_6$ alkyl substituted with at least one fluorine. In aspects, $R^9$ is methyl substituted with at least one fluorine. In aspects, $R^9$ is —$CF_3$. In aspects, $R^9$ is —$CHF_2$. In aspects, $R^9$ is —$CH_2F$. In aspects, $R^9$ is ethyl substituted with at least one fluorine. In aspects, $R^9$ is propyl substituted with at least one fluorine. In aspects, $R^9$ is butyl substituted with at least one fluorine. In aspects, $R^9$ is a substituted or unsubstituted alkenyl. In aspects, $R^9$ is a substituted or unsubstituted $C_2$-$C_6$ alkenyl. In aspects, $R^9$ is a substituted or unsubstituted vinyl.

In aspects, $R^{10}$ is hydrogen. In aspects, $R^{10}$ is unsubstituted $C_1$-$C_6$ alkyl. In aspects, $R^{10}$ is unsubstituted methyl. In aspects, $R^{10}$ is unsubstituted ethyl. In aspects, $R^{10}$ is unsubstituted propyl. In aspects, $R^{10}$ is unsubstituted butyl. In aspects, $R^{10}$ is $C_1$-$C_6$ alkyl substituted with at least one fluorine. In aspects, $R^{10}$ is methyl substituted with at least one fluorine. In aspects, $R^{10}$ is —$CF_3$. In aspects, $R^{10}$ is —$CHF_2$. In aspects, $R^{10}$ is —$CH_2F$. In aspects, $R^{10}$ is ethyl substituted with at least one fluorine. In aspects, $R^{10}$ is propyl substituted with at least one fluorine. In aspects, $R^{10}$ is butyl substituted with at least one fluorine. In aspects, $R^{10}$ is a substituted or unsubstituted alkenyl. In aspects, $R^{10}$ is a substituted or unsubstituted $C_2$-$C_6$ alkenyl. In aspects, $R^{10}$ is a substituted or unsubstituted vinyl.

In aspects, $R^4$, $R^5$, $R^6$, and $R^7$ are each independently hydrogen, substituted (e.g., substituted with at least one substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with at least one substituent group, size-limited substituent group, or lower substituent group) or unsubstituted heteroalkyl (e.g., 2 to 8 membered, 2 to 6 membered, 4 to 6 membered, 2 to 3 membered, or 4 to 5 membered), substituted (e.g., substituted with at least one substituent group, size-limited substituent group, or lower substituent group) or unsubstituted aryl (e.g., $C_6$-$C_{10}$ or phenyl), or substituted (e.g., substituted with at least one substituent group, size-limited substituent group, or lower substituent group) or unsubstituted heteroaryl (e.g., 5 to 10 membered, 5 to 9 membered, or 5 to 6 membered).

In aspects, $R^4$ is independently hydrogen. In aspects, $R^4$ is independently substituted or unsubstituted $C_1$-$C_6$ alkyl. In aspects, $R^4$ is independently unsubstituted $C_1$-$C_6$ alkyl. In aspects, $R^4$ is independently unsubstituted methyl. In aspects, $R^4$ is independently unsubstituted ethyl. In aspects, $R^4$ is independently unsubstituted propyl. In aspects, $R^4$ is independently unsubstituted propyl. In aspects, $R^4$ is independently unsubstituted butyl. In aspects, $R^4$ is independently unsubstituted butyl. In aspects, $R^4$ is independently a substituted or unsubstituted alkenyl. In aspects, $R^4$ is independently a substituted or unsubstituted $C_2$-$C_6$ alkenyl. In aspects, $R^4$ is independently a substituted or unsubstituted vinyl. In aspects, $R^4$ is independently substituted or unsubstituted aryl. In aspects, $R^4$ is independently substituted or unsubstituted phenyl. In aspects, $R^4$ is independently toluyl. In aspects, $R^4$ is independently xylyl. In aspects, $R^4$ is independently unsubstituted phenyl. In aspects, $R^4$ is independently substituted or unsubstituted naphthyl. In aspects, $R^4$ is independently unsubstituted naphthyl.

In aspects, $R^5$ is independently hydrogen. In aspects, $R^5$ is independently substituted or unsubstituted $C_1$-$C_6$ alkyl. In aspects, $R^5$ is independently substituted or unsubstituted $C_1$-$C_6$ alkyl. In aspects, $R^5$ is independently substituted or unsubstituted methyl. In aspects, $R^5$ is independently substituted or unsubstituted ethyl. In aspects, $R^5$ is independently substituted or unsubstituted propyl. In aspects, $R^5$ is independently substituted or unsubstituted butyl. In aspects, $R^5$ is independently a substituted or unsubstituted alkenyl. In aspects, $R^5$ is independently a substituted or unsubstituted $C_2$-$C_6$ alkenyl. In aspects, $R^5$ is independently a substituted or unsubstituted vinyl. In aspects, $R^5$ is independently substituted or unsubstituted aryl. In aspects, $R^5$ is independently substituted or unsubstituted phenyl. In aspects, $R^5$ is independently toluyl substituted with at least one fluorine. In aspects, $R^5$ is independently xylyl substituted with at least one fluorine. In aspects, $R^5$ is independently phenyl substituted with at least one fluorine. In aspects, $R^5$ is independently naphthyl substituted with at least one fluorine.

In aspects, $R^6$ is independently hydrogen. In aspects, $R^6$ is independently substituted or unsubstituted $C_1$-$C_6$ alkyl. In aspects, $R^6$ is independently substituted or unsubstituted $C_1$-$C_6$ alkyl. In aspects, $R^6$ is independently unsubstituted methyl. In aspects, $R^6$ is independently unsubstituted ethyl. In aspects, $R^6$ is independently unsubstituted propyl. In aspects, $R^6$ is independently unsubstituted butyl. In aspects, $R^6$ is independently a substituted or unsubstituted alkenyl. In aspects, $R^6$ is independently a substituted or unsubstituted $C_2$-$C_6$ alkenyl. In aspects, $R^6$ is independently a substituted or unsubstituted vinyl. In aspects, $R^6$ is independently substituted or unsubstituted aryl. In aspects, $R^6$ is independently substituted or unsubstituted phenyl. In aspects, $R^6$ is independently toluyl. In aspects, $R^6$ is independently xylyl. In aspects, $R^6$ is independently unsubstituted phenyl. In aspects, $R^6$ is independently substituted or unsubstituted naphthyl. In aspects, $R^6$ is independently unsubstituted naphthyl.

In aspects, $R^7$ is independently hydrogen. In aspects, $R^7$ is independently substituted or unsubstituted $C_1$-$C_6$ alkyl. In aspects, $R^7$ is independently substituted or unsubstituted $C_1$-$C_6$ alkyl. In aspects, $R^7$ is independently unsubstituted methyl. In aspects, $R^7$ is independently unsubstituted ethyl. In aspects, $R^7$ is independently unsubstituted propyl. In aspects, $R^7$ is independently unsubstituted butyl. In aspects, $R^7$ is independently a substituted or unsubstituted alkenyl. In aspects, $R^7$ is independently a substituted or unsubstituted $C_2$-$C_6$ alkenyl. In aspects, $R^7$ is independently a substituted or unsubstituted vinyl. In aspects, $R^7$ is independently substituted or unsubstituted aryl. In aspects, $R^7$ is independently substituted or unsubstituted phenyl. In aspects, $R^7$ is independently toluyl. In aspects, $R^7$ is independently xylyl. In aspects, $R^7$ is independently unsubstituted phenyl. In aspects, $R^7$ is independently substituted or unsubstituted naphthyl. In aspects, $R^7$ is independently unsubstituted naphthyl.

m and n are an integer from 1 to about 1,000. In aspects, m and n are an integer from 1 to about 500. In aspects, m and n are an integer from 1 to about 400. In aspects, m and n are an integer from 1 to about 300. In aspects, m and n are an integer from 1 to about 200. In aspects, m and n are an integer from 1 to about 100. In aspects, m and n are an integer from 1 to about 90. In aspects, m and n are an integer from 1 to about 80. In aspects, m and n are an integer from 1 to about 70. In aspects, m and n are an integer from 1 to about 60. In aspects, m and n are an integer from 1 to about 50. In aspects, m and n are an integer from 1 to about 40. In aspects, m and n are an integer from 1 to about 30. In aspects, m and n are an integer from 1 to about 25. In aspects, m and n are an integer from 1 to about 20. In aspects, m and n are an integer from 1 to about 15. In aspects, m and n are an integer from 1 to about 10. In aspects, m and n are an integer from 5 to about 20. In aspects, m and n are an integer from 5 to about 15.

In embodiments, the ratio of m:n is from about 10:90 to about 90:10. In aspects, the ratio of m:n is from about 20:80 to about 80:20. In aspects, the ratio of m:n is from about 25:75 to about 75:25. In aspects, the ratio of m:n is from about 30:70 to about 70:30. In aspects, the ratio of m:n is from about 40:60 to about 60:40. In aspects, the ratio of m:n is from about 40:60 to about 50:50. In aspects, the ratio of m:n is from about 45:55 to about 55:45. In aspects, the ratio of m:n is about 45:55. In aspects, the ratio of m:n is about 40:60. In aspects, the ratio of m:n is about 50:50. In aspects, the ratio of m:n is about 55:45.

In embodiments, the copolymer has a number average molecular weight of about 100 to about 25,000. In aspects, the copolymer has a number average molecular weight of about 100 to about 20,000. In aspects, the copolymer has a number average molecular weight of about 100 to about 15,000. In aspects, the copolymer has a number average molecular weight of about 500 to about 10,000. In aspects, the copolymer has a number average molecular weight of about 1,000 to about 6,000. In aspects, the copolymer has a number average molecular weight of about 2,000 to about 5,000. In aspects, the copolymer has a number average molecular weight of about 3,000 to about 4,000. In aspects, the copolymer has a number average molecular weight of about 3,500.

In an aspect, the disclosure provides a fluorosilicone copolymer of Formula (A):

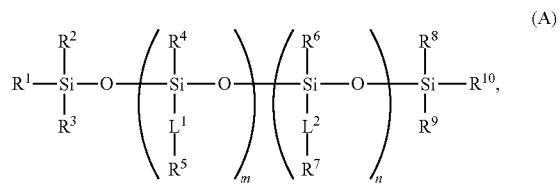

where the substituents are as defined herein. The copolymers described herein can be random, block, or alternating. The copolymers can be linear or branched. In aspects, the copolymers are random and linear.

$R^1$, $R^2$, $R^3$, $R^8$, $R^9$, and $R^{10}$ are the same definitions described above for the compound of Formula (I).

In aspects, $R^1$, $R^2$, $R^3$, $R^8$, $R^9$, and $R^{10}$ are each independently hydrogen, substituted or unsubstituted alkyl, substituted or unsubstituted heteroalkyl, substituted or unsubstituted aryl, or substituted or unsubstituted heteroaryl. In aspects, $R^1$, $R^2$, $R^3$, $R^8$, $R^9$, and $R^{10}$ are each independently hydrogen or substituted or unsubstituted alkyl. In aspects, $R^1$, $R^2$, $R^3$, $R^8$, $R^9$, and $R^{10}$ are each independently hydrogen or unsubstituted alkyl. In aspects, $R^1$, $R^2$, $R^3$, $R^8$, $R^9$, and $R^{10}$ are each independently hydrogen or unsubstituted $C_{1-6}$ alkyl. In aspects, $R^1$, $R^2$, $R^3$, $R^8$, $R^9$, and $R^{10}$ are each independently hydrogen or unsubstituted $C_{1-4}$ alkyl. In aspects, $R^1$, $R^2$, $R^3$, $R^8$, $R^9$, and $R^{10}$ are each independently hydrogen or unsubstituted $C_{1-3}$ alkyl. In aspects, $R^1$, $R^2$, $R^3$, $R^8$, $R^9$, and $R^{10}$ are each independently hydrogen, methyl, or ethyl. In aspects, $R^1$, $R^2$, $R^3$, $R^8$, $R^9$, and $R^{10}$ are each independently hydrogen or methyl.

In aspects, $R^1$, $R^2$, $R^3$, $R^8$, $R^9$, and $R^{10}$ are each independently $C_{1-6}$ alkyl substituted with at least one fluorine. In aspects, $R^1$, $R^2$, $R^3$, $R^8$, $R^9$, and $R^{10}$ are each independently $C_{1-4}$ alkyl substituted with at least one fluorine. In aspects, $R^1$, $R^2$, $R^3$, $R^8$, $R^9$, and $R^{10}$ are each independently $C_{1-3}$ alkyl substituted with at least one fluorine. In aspects, $R^1$, $R^2$, $R^3$, $R^8$, $R^9$, and $R^{10}$ are each independently $C_{1-2}$ alkyl substituted with at least one fluorine. In aspects, $R^1$, $R^2$, $R^3$, $R^8$, $R^9$, and $R^{10}$ are each independently propyl substituted with at least one fluorine. In aspects, $R^1$, $R^2$, $R^3$, $R^8$, $R^9$, and $R^{10}$ are each independently ethyl substituted with at least one fluorine. In aspects, $R^1$, $R^2$, $R^3$, $R^8$, $R^9$, and $R^{10}$ are each independently methyl substituted with at least one fluorine. In aspects, $R^1$, $R^2$, $R^3$, $R^8$, $R^9$, and $R^{10}$ are each —$CF_3$. In aspects, $R^1$, $R^2$, $R^3$, $R^8$, $R^9$, and $R^{10}$ are each —$CHF_2$. In aspects, $R^1$, $R^2$, $R^3$, $R^8$, $R^9$, and $R^{10}$ are each —$CH_2F$. In aspects, "at least one fluorine" is one fluorine. In aspects, "at least one fluorine" is two fluorine. In aspects, "at least one fluorine" is three fluorine. In aspects, "at least one fluorine" is four fluorine. In aspects, "at least one fluorine" is five fluorine.

In aspects, $R^1$, $R^2$, $R^3$, $R^8$, $R^9$, and $R^{10}$ are each independently $C_{1-6}$ alkyl substituted with 6 membered aryl that is substituted with 1 to 5 fluorine. In aspects, $R^1$, $R^2$, $R^3$, $R^8$, $R^9$, and $R^{10}$ are each independently $C_{1-4}$ alkyl substituted with 6 membered aryl that is substituted with 1 to 5 fluorine. In aspects, $R^1$, $R^2$, $R^3$, $R^8$, $R^9$, and $R^{10}$ are each independently $C_{1-3}$ alkyl substituted with 6 membered aryl that is substituted with 1 to 5 fluorine. In aspects, $R^1$, $R^2$, $R^3$, $R^8$, $R^9$, and $R^{10}$ are each independently $C_{1-2}$ alkyl substituted with 6 membered aryl that is substituted with 1 to 5 fluorine. In aspects, $R^1$, $R^2$, $R^3$, $R^8$, $R^9$, and $R^{10}$ are each independently propyl substituted with 6 membered aryl that is substituted with 1 to 5 fluorine. In aspects, $R^1$, $R^2$, $R^3$, $R^8$, $R^9$, and $R^{10}$ are each independently ethyl substituted with 6 membered aryl that is substituted with 1 to 5 fluorine. In aspects, $R^1$, $R^2$, $R^3$, $R^8$, $R^9$, and $R^{10}$ are each independently methyl substituted with 6 membered aryl that is substituted with 1 to 5 fluorine. In aspects, the 6 membered aryl is substituted with 1 fluorine. In aspects, the 6 membered aryl is substituted with 2 fluorine. In aspects, the 6 membered aryl is substituted with 3 fluorine. In aspects, the 6 membered aryl is substituted with 4 fluorine. In aspects, the 6 membered aryl is substituted with 5 fluorine. In aspects, the 6 membered aryl is phenyl.

In aspects, $R^1$, $R^2$, $R^3$, $R^8$, $R^9$, and $R^{10}$ are each independently 6 membered aryl substituted with 1 to 5 fluorine. In aspects, $R^1$, $R^2$, $R^3$, $R^8$, $R^9$, and $R^{10}$ are each independently 6 membered aryl substituted with 1 to 5 fluorine. In aspects, $R^1$, $R^2$, $R^3$, $R^8$, $R^9$, and $R^{10}$ are each independently 6 membered aryl substituted with 1 to 5 fluorine. In aspects, $R^1$, $R^2$, $R^3$, $R^8$, $R^9$, and $R^{10}$ are each independently 6 membered aryl substituted with 1 to 5 fluorine. In aspects, $R^1$, $R^2$, $R^3$, $R^8$, $R^9$, and $R^{10}$ are each independently 6 membered aryl that is substituted with 1 to 5 fluorine. In aspects, the 6 membered aryl is substituted with 1 fluorine. In aspects, the 6 membered aryl is substituted with 2 fluorine. In aspects, the 6 membered aryl is substituted with 3 fluorine. In aspects, the 6 membered aryl is substituted with 4 fluorine. In aspects, the 6 membered aryl is substituted with 5 fluorine. In aspects, the 6 membered aryl is phenyl.

In aspects, $R^1$, $R^2$, $R^3$, $R^8$, $R^9$, and $R^{10}$ are each independently -$M^1$-$N^1$, wherein $M^1$ is $C_{1-6}$ alkylene; and $N^1$ is fluorine or phenyl substituted with 1 to 5 fluorine, 1 to 5 $C_{1-4}$ alkyl substituted with at least one fluorine, or a combination thereof, with the proviso that the phenyl contains no more than 5 substitutents. In aspects, $M^1$ is propylene. In aspects, $M^1$ is ethylene. In aspects, $M^1$ is methylene. In aspects, $N^1$ is phenyl substituted with 1 fluorine. In aspects, $N^1$ is phenyl substituted with 2 fluorine. In aspects, $N^1$ is phenyl substituted with 3 fluorine. In aspects, $N^1$ is phenyl substituted with 4 fluorine. In aspects, $N^1$ is phenyl substituted with 5 fluorine. In aspects, $N^1$ is phenyl substituted with —$CF_3$.

$R^4$ and $R^6$ are the same definitions described above for the compound of Formula (I).

In aspects, $R^4$ and $R^6$ are each independently hydrogen, substituted or unsubstituted alkyl, substituted or unsubstituted heteroalkyl, substituted or unsubstituted aryl, or substituted or unsubstituted heteroaryl. In aspects, $R^4$ and $R^6$ are each independently hydrogen or substituted or unsubstituted alkyl. In aspects, $R^4$ and $R^6$ are each independently hydrogen or unsubstituted alkyl. In aspects, $R^4$ and $R^6$ are each independently hydrogen or unsubstituted $C_{1-6}$ alkyl. In aspects, $R^4$ and $R^6$ are each independently hydrogen or unsubstituted $C_{1-4}$ alkyl. In aspects, $R^4$ and $R^6$ are each independently hydrogen or unsubstituted $C_{1-3}$ alkyl. In aspects, $R^4$ and $R^6$ are each independently hydrogen, methyl, or ethyl. In aspects, $R^4$ and $R^6$ are each independently hydrogen or methyl.

$L^1$ and $L^2$ are each independently a bond, —O—, —NH—, —S—, —S(O)$_2$—, —C(O)—, —NHC(O)—, —C(O)NH—, —OC(O)—, —C(O)O—, substituted (e.g., substituted with at least one substituent group, size-limited substituent group, or lower substituent group) or unsubstituted alkylene (e.g., $C_1$-$C_8$, $C_1$-$C_6$, $C_1$-$C_4$, or $C_1$-$C_2$), or substituted (e.g., substituted with at least one substituent group, size-limited substituent group, or lower substituent group) or unsubstituted heteroalkylene (e.g., 2 to 8 membered, 2 to 6 membered, 4 to 6 membered, 2 to 3 membered, or 4 to 5 membered). In aspects, $L^1$ is independently a substituted or unsubstituted alkenylene. In aspects, $L^1$ is independently a substituted or unsubstituted $C_1$-$C_6$ alkenylene. In aspects, $L^2$ is independently a substituted or unsubstituted alkenylene. In aspects, $L^2$ is independently a substituted or unsubstituted $C_1$-$C_6$ alkenylene.

In aspects, $L^1$ and $L^2$ are each independently a bond, —O—, —NH—, —S—, —S(O)$_2$—, —C(O)—, —NHC(O)—, —C(O)NH—, —OC(O)—, —C(O)O—, substituted or unsubstituted alkylene, or substituted or unsubstituted heteroalkylene. In aspects, $L^1$ and $L^2$ are each independently a bond, substituted or unsubstituted alkylene, or substituted or unsubstituted heteroalkylene. In aspects, $L^1$ and $L^2$ are each independently a bond or substituted or unsubstituted alkylene. In aspects, $L^1$ and $L^2$ are each independently substituted or unsubstituted alkylene. In aspects, $L^1$ and $L^2$ are each independently unsubstituted alkylene. In aspects, $L^1$ and $L^2$ are each independently substituted alkylene. In aspects, $L^1$ and $L^2$ are each independently unsubstituted $C_{1-6}$ alkylene. In aspects, $L^1$ and $L^2$ are each independently unsubstituted $C_{1-4}$ alkylene. In aspects, $L^1$ and $L^2$ are each independently unsubstituted $C_{1-3}$ alkylene. In aspects, $L^1$ and $L^2$ are each independently unsubstituted $C_{1-2}$ alkylene. In aspects, $L^1$ and $L^2$ are each independently unsubstituted $C_1$ alkylene. In aspects, $L^1$ and $L^2$ are each independently unsubstituted $C_2$ alkylene. In aspects, $L^1$ and $L^2$ are each independently unsubstituted $C_3$ alkylene. In aspects, $L^1$ and $L^2$ are each independently unsubstituted $C_4$ alkylene. In aspects, $L^1$ and $L^2$ are each independently $C_{1-6}$ alkylene substituted by a $C_{1-4}$ alkyl. In aspects, $L^1$ and $L^2$ are each independently $C_{1-4}$ alkylene substituted by a $C_{1-3}$ alkyl. In aspects, $L^1$ and $L^2$ are each independently $C_{1-3}$ alkylene substituted by a $C_{1-2}$ alkyl. In aspects, $L^1$ and $L^2$ are each independently $C_{1-2}$ alkylene substituted with methyl. In aspects, $L^1$ and $L^2$ are each independently $C_1$ alkylene substituted with methyl. In aspects, $L^1$ and $L^2$ are each independently $C_2$ alkylene substituted with methyl. In aspects, $L^1$ and $L^2$ are each independently $C_3$ alkylene substituted with methyl. In aspects, $L^1$ and $L^2$ are each independently $C_4$ alkylene substituted with methyl.

$R^5$ is the same definition described above for the compound of Formula (I).

In aspects, $R^5$ is independently $R^{5A}$-substituted aryl (e.g., $C_6$-$C_{10}$ or phenyl), $R^{5A}$-substituted heteroaryl (e.g., 5 to 10 membered, 5 to 9 membered, or 5 to 6 membered), $R^{5A}$-substituted alkyl (e.g., $C_1$-$C_8$, $C_1$-$C_6$, $C_1$-$C_4$, or $C_1$-$C_2$), or $R^{5A}$-substituted heteroalkyl (e.g., 2 to 8 membered, 2 to 6 membered, 4 to 6 membered, 2 to 3 membered, or 4 to 5 membered). In aspects, $R^5$ is independently $R^{5A}$-substituted aryl; wherein $R^{5A}$ is independently fluorine or $C_1$-$C_4$ alkyl substituted with at least one fluorine. In aspects, $R^5$ is independently $R^{5A}$-substituted phenyl. In aspects, $R^5$ is independently $R^{5A}$-substituted naphthyl. In aspects, $R^5$ is independently $R^{5A}$-substituted alkyl; wherein $R^{5A}$ is independently fluorine or $C_1$-$C_4$ alkyl substituted with at least one fluorine.

In aspects, $R^{5A}$ is independently fluorine, $R^{5B}$-substituted alkyl (e.g., $C_1$-$C_8$, $C_1$-$C_6$, $C_1$-$C_4$, or $C_1$-$C_2$), or $R^{5B}$-substituted heteroalkyl (e.g., 2 to 8 membered, 2 to 6 membered, 4 to 6 membered, 2 to 3 membered, or 4 to 5 membered); and $R^{5B}$ is fluorine. In aspects, $R^{5A}$ is independently $R^{5B}$-substituted alkenyl; and $R^{5B}$ is independently fluorine.

In aspects, $R^{5A}$ is independently fluorine. In aspects, $R^{5A}$ is independently methyl substituted with at least one fluorine. In aspects, $R^{5A}$ is independently —$CF_3$. In aspects, $R^{5A}$ is independently —$CHF_2$. In aspects, $R^{5A}$ is independently —$CH_2F$. In aspects, $R^{5A}$ is independently ethyl substituted with at least one fluorine. In aspects, $R^{5A}$ is independently propyl substituted with at least one fluorine. In aspects, $R^{5A}$ is independently butyl substituted with at least one fluorine.

In aspects, $R^5$ is independently $R^{5A}$-substituted aryl, $R^{5A}$-substituted heteroaryl, $R^{5A}$-substituted alkyl, or $R^{5A}$-substituted heteroalkyl; $R^{5A}$ is independently fluorine, $R^{5B}$-substituted alkyl, $R^{5B}$-substituted heteroalkyl; $R^{5B}$ is independently fluorine. In aspects, $R^5$ is independently $R^{5A}$-substituted aryl; wherein $R^{5A}$ is independently fluorine or $C_1$-$C_4$ alkyl substituted with at least one fluorine. In aspects, $R^5$ is independently $R^{5A}$-substituted 5-membered aryl; wherein $R^{5A}$ is independently fluorine or $C_1$-$C_4$ alkyl substituted with at least one fluorine. In aspects, $R^5$ is independently $R^{5A}$-substituted 6-membered aryl; wherein $R^{5A}$ is independently fluorine or $C_1$-$C_4$ alkyl substituted with at least one fluorine. In aspects, $R^5$ is independently $R^{5A}$-substituted aryl; wherein $R^{5A}$ is independently fluorine or $C_1$-$C_4$ alkyl substituted with at least one fluorine. In aspects, $R^5$ is independently $R^{5A}$-substituted alkyl; where $R^{5A}$ is independently fluorine or $C_1$-$C_4$ alkyl substituted with at least one fluorine. In aspects, $R^{5A}$ is independently $R^{5B}$-substituted alkyl.

$R^7$ is the definition described above for the compound of Formula (I).

In aspects, $R^7$ is independently unsubstituted or $R^{7A}$-substituted alkyl (e.g., $C_1$-$C_8$, $C_1$-$C_6$, $C_1$-$C_4$, or $C_1$-$C_2$), unsubstituted or $R^{7A}$-substituted heteroalkyl (e.g., 2 to 8 membered, 2 to 6 membered, 4 to 6 membered, 2 to 3 membered, or 4 to 5 membered), unsubstituted or $R^{7A}$-substituted aryl (e.g., $C_6$-$C_{10}$ or phenyl), or unsubstituted or $R^{7A}$-substituted heteroaryl (e.g., 5 to 10 membered, 5 to 9 membered, or 5 to 6 membered). In aspects, $R^7$ is independently unsubstituted or $R^{7A}$-substituted alkyl. In aspects, $R^7$ is independently $R^{7A}$-substituted aryl; wherein $R^{7A}$ is independently fluorine or $C_1$-$C_4$ alkyl substituted with at least one fluorine. In aspects, $R^7$ is independently $R^{7A}$-substituted phenyl. In aspects, $R^7$ is independently $R^{7A}$-substituted naphthyl.

In aspects, $R^{7A}$ is independently fluorine, $R^{7B}$-substituted alkyl (e.g., $C_1$-$C_8$, $C_1$-$C_6$, $C_1$-$C_4$, or $C_1$-$C_2$), or $R^{7B}$-substituted heteroalkyl (e.g., 2 to 8 membered, 2 to 6 membered, 4 to 6 membered, 2 to 3 membered, or 4 to 5 membered); and $R^{7B}$ is independently fluorine. In aspects, $R^{7A}$ is independently $R^{7B}$-substituted alkenyl; and $R^{7B}$ is independently fluorine.

In aspects, $R^7$ is independently unsubstituted or $R^{7A}$-substituted alkyl or unsubstituted or $R^{7A}$-substituted aryl; wherein $R^{7A}$ is independently fluorine or $R^{7B}$-substituted alkyl; wherein $R^{7B}$ is independently fluorine. In aspects, $R^{7A}$ is independently fluorine. In aspects, $R^{7A}$ is independently $R^{7B}$-substituted alkyl; and $R^{7B}$ is independently fluorine.

In aspects, $R^{7A}$ is independently $C_{1-4}$ alkyl substituted with at least one fluorine. In aspects, $R^{7A}$ is independently methyl substituted with at least one fluorine. In aspects, $R^{7A}$ is independently —$CF_3$. In aspects, $R^{7A}$ is independently —$CHF_2$. In aspects, $R^{7A}$ is independently —$CH_2F$. In aspects, $R^{7A}$ is independently ethyl substituted with at least one fluorine. In aspects, $R^{7A}$ is independently propyl substituted with at least one fluorine. In aspects, $R^{7A}$ is independently butyl substituted with at least one fluorine.

In aspects, $R^7$ is independently unsubstituted or $R^{7A}$-substituted alkyl, unsubstituted or $R^{7A}$-substituted heteroalkyl, unsubstituted or $R^{7A}$-substituted aryl, or unsubstituted or $R^{7A}$-substituted heteroaryl; $R^{7A}$ is independently fluorine, $R^{7B}$-substituted alkyl, or $R^{7B}$-substituted heteroalkyl; $R^{7B}$ is independently fluorine. In aspects, $R^7$ is independently unsubstituted or $R^{7A}$-substituted alkyl or unsubstituted or $R^{7A}$-substituted aryl; $R^{7A}$ is independently fluorine, $R^{7B}$-substituted alkyl, or $R^{7B}$-substituted heteroalkyl; $R^{7B}$ is independently fluorine. In aspects, $R^7$ is independently phenyl, unsubstituted $C_1$-$C_6$ alkyl, or $C_1$-$C_6$ alkyl substituted with at least one fluorine. In aspects, $R^7$ is independently unsubstituted or $R^{7A}$-substituted alkyl or unsubstituted or $R^{7A}$-substituted aryl; wherein $R^{7A}$ is independently fluorine or $R^{7B}$-substituted alkyl; wherein $R^{7B}$ is independently fluorine. In aspects, $R^7$ is independently unsubstituted or $R^{7A}$-substituted alkyl. In aspects, $R^{7A}$ is independently $R^{7B}$-substituted $C_1$-$C_6$ alkyl. In aspects, $R^{7A}$ is independently $R^{7B}$-substituted $C_1$-$C_3$ alkyl.

m and n are same the definition described above for the compound of Formula (I).

In aspects, m and n are an integer from 1 to about 100. In aspects, m and n are an integer from 1 to about 90. In aspects, m and n are an integer from 1 to about 80. In aspects, m and n are an integer from 1 to about 70. In aspects, m and n are an integer from 1 to about 60. In aspects, m and n are an integer from 1 to about 50. In aspects, m and n are an integer from 1 to about 40. In aspects, m and n are an integer from 1 to about 30. In aspects, m and n are an integer from 1 to about 25. In aspects, m and n are an integer from 1 to about 20. In aspects, m and n are an integer from 1 to about 15. In aspects, m and n are an integer from 1 to about 10. In aspects, m and n are an integer from 5 to about 20. In aspects, m and n are an integer from 5 to about 15.

In embodiments, the ratio of m:n is from about 10:90 to about 90:10. In aspects, the ratio of m:n is from about 20:80 to about 80:20. In aspects, the ratio of m:n is from about 25:75 to about 75:25. In aspects, the ratio of m:n is from about 30:70 to about 70:30. In aspects, the ratio of m:n is from about 40:60 to about 60:40. In aspects, the ratio of m:n is from about 40:60 to about 50:50. In aspects, the ratio of m:n is from about 45:55 to about 55:45. In aspects, the ratio of m:n is about 45:55. In aspects, the ratio of m:n is about 40:60. In aspects, the ratio of m:n is about 50:50. In aspects, the ratio of m:n is about 55:45.

In embodiments, the copolymer has a number average molecular weight as described above for the compound of Formula (I). In aspects, the copolymer has a number average molecular weight of about 500 to about 10,000. In aspects, the copolymer has a number average molecular weight of about 1,000 to about 6,000. In aspects, the copolymer has a number average molecular weight of about 2,000 to about 5,000. In aspects, the copolymer has a number average molecular weight of about 3,000 to about 4,000. In aspects, the copolymer has a number average molecular weight of about 3,500.

In aspects, $R^1$, $R^2$, $R^3$, $R^1$, $R^9$, and $R^{10}$ are each independently hydrogen, unsubstituted $C_1$-$C_6$ alkyl, or $C_1$-$C_6$ alkyl substituted with at least one fluorine; $R^4$ and $R^6$ are each independently hydrogen, substituted or unsubstituted $C_1$-$C_6$ alkyl, or substituted or unsubstituted phenyl; $L^1$ and $L^2$ are each independently a bond or a substituted or unsubstituted $C_1$-$C_6$ alkylene; $R^5$ is 5 or 6 membered $R^{5A}$-substituted aryl wherein $R^{5A}$ is fluorine or $C_1$-$C_4$ alkyl substituted with at least one fluorine; $R^7$ is unsubstituted phenyl, phenyl substituted with at least one fluorine, unsubstituted $C_1$-$C_6$ alkyl, or $C_1$-$C_6$ alkyl substituted with at least one fluorine; and m and n are each independently an integer from 1 to about 50.

In aspects, $R^1$, $R^2$, $R^3$, $R^8$, $R^9$, and $R^{10}$ are each independently hydrogen, —$CH_3$, or —$CF_3$; $R^4$ is independently hydrogen or —$CH_3$; $R^6$ is independently hydrogen, —$CH_3$, or unsubstituted phenyl; $L^1$ is independently unsubstituted methylene, methylene substituted with a $C_{1-2}$ alkyl, unsubstituted ethylene, ethylene substituted with a $C_{1-2}$ alkyl, unsubstituted propylene, or methylene substituted with a $C_{1-2}$ alkyl; $L^2$ is independently a bond, unsubstituted methylene, unsubstituted ethylene, or unsubstituted propylene; $R^5$ is independently phenyl substituted with 1 to 5 fluorine; $R^7$ is independently phenyl substituted with 1 to 5 fluorine or methyl substituted with 1 to 3 fluorine; and m and n are each independently an integer from 1 to about 25.

In embodiments, the disclosure provides a fluorosilicone copolymer of Formula (B):

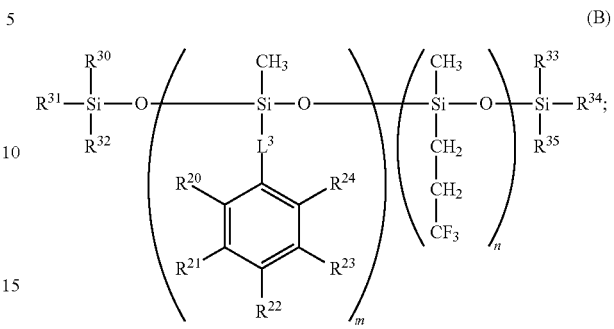

wherein $R^{20}$, $R^{21}$, $R^{22}$, $R^{23}$, and $R^{24}$ are each independently hydrogen, fluorine, or $C_1$-$C_4$ alkyl substituted with at least one fluorine; $L^3$ is independently —$(CH_2)_2$— or —CH($CH_3$)—; $R^{30}$, $R^{31}$, $R^{32}$, $R^{33}$, $R^{34}$, and $R^{35}$ are each independently —$CH_3$ or —$CF_3$; and m and n are each independently an integer from 1 to 20, and the ratio of m:n is from about 25:75 to about 75:25. The copolymers described herein can be random, block, or alternating. The copolymers can be linear or branched. In aspects, the copolymers are random and linear.

In aspects, $L^3$ is —$(CH_2)_2$— in 1% to 99% of the m units, and $L^3$ is —CH($CH_3$)— in 99% to 1% of the m units. In aspects, $L^3$ is —$(CH_2)_2$— in 5% to 95% of the m units, and $L^3$ is —CH($CH_3$)— in 95% to 5% of the m units. In aspects, $L^3$ is —$(CH_2)_2$— in 10% to 90% of the m units, and $L^3$ is —CH($CH_3$)— in 90% to 10% of the m units. In aspects, $L^3$ is —$(CH_2)_2$— in 20% to 80% of the m units, and $L^3$ is —CH($CH_3$)— in 80% to 20% of the m units. In aspects, $L^3$ is —$(CH_2)_2$— in 30% to 80% of the m units, and $L^3$ is —CH($CH_3$)— in 70% to 20% of the m units. In aspects, $L^3$ is —$(CH_2)_2$— in 40% to 80% of the m units, and $L^3$ is —CH($CH_3$)— in 60% to 20% of the m units. In aspects, $L^3$ is —$(CH_2)_2$— in 50% to 80% of the m units, and $L^3$ is —CH($CH_3$)— in 50% to 20% of the m units. In aspects, $L^3$ is —$(CH_2)_2$—. In aspects, $L^3$ is —CH($CH_3$)—.

In aspects, m and n are each independently an integer from 2 to 18. In aspects, m and n are each independently an integer from 4 to 16. In aspects, m and n are each independently an integer from 5 to 15. In aspects, m and n are each independently an integer from 6 to 12. In aspects, the ratio of m:n is from about 40:60 to about 60:40. In aspects, the ratio of m:n is from about 40:60 to about 50:50. In aspects, the ratio of m:n is about 45:55. In aspects, the ratio of m:n is about 40:60. In aspects, the ratio of m:n is about 50:50. In aspects, the ratio of m:n is about 55:45.

In aspects, the copolymer has a number average molecular weight of about 500 to about 8,000. In aspects, the copolymer has a number average molecular weight of about 1,000 to about 6,000. In aspects, the copolymer has a number average molecular weight of about 2,000 to about 5,000. In aspects, the copolymer has a number average molecular weight from about 3,000 to about 4,000. In aspects, the copolymer has a number average molecular weight of about 3,500.

In aspects, $R^{20}$ is independently hydrogen. In aspects, $R^{20}$ is independently fluorine. In aspects, $R^{20}$ is independently $C_1$-$C_4$ alkyl substituted with at least one fluorine. In aspects, $R^{20}$ is independently methyl substituted with at least one fluorine. In aspects, $R^{20}$ is independently —$CF_3$. In aspects, $R^{20}$ is independently —$CHF_2$. In aspects, $R^{20}$ is independently —$CH_2F$. In aspects, $R^{20}$ is independently ethyl substituted with at least one fluorine. In aspects, $R^{20}$ is independently propyl substituted with at least one fluorine. In aspects, $R^{20}$ is independently butyl substituted with at least one fluorine.

In aspects, $R^{21}$ is independently hydrogen. In aspects, $R^{21}$ is independently fluorine. In aspects, $R^{21}$ is independently $C_1$-$C_4$ alkyl substituted with at least one fluorine. In aspects, $R^{21}$ is independently methyl substituted with at least one fluorine. In aspects, $R^{21}$ is independently —$CF_3$. In aspects, $R^{21}$ is independently —$CHF_2$. In aspects, $R^{21}$ is independently —$CH_2F$. In aspects, $R^{21}$ is independently ethyl substituted with at least one fluorine. In aspects, $R^{21}$ is independently propyl substituted with at least one fluorine In aspects, $R^{21}$ is independently butyl substituted with at least one fluorine.

In aspects, $R^{22}$ is independently hydrogen. In aspects, $R^{22}$ is independently fluorine. In aspects, $R^{22}$ is independently $C_1$-$C_4$ alkyl substituted with at least one fluorine. In aspects, $R^{22}$ is independently methyl substituted with at least one fluorine. In aspects, $R^{22}$ is independently —$CF_3$. In aspects, $R^{22}$ is independently —$CHF_2$. In aspects, $R^{22}$ is independently —$CH_2F$. In aspects, $R^{22}$ is independently ethyl substituted with at least one fluorine. In aspects, $R^{22}$ is independently propyl substituted with at least one fluorine. In aspects, $R^{22}$ is independently butyl substituted with at least one fluorine.

In aspects, $R^{23}$ is independently hydrogen. In aspects, $R^{23}$ is independently fluorine. In aspects, $R^{23}$ is independently $C_1$-$C_4$ alkyl substituted with at least one fluorine. In aspects, $R^{23}$ is independently methyl substituted with at least one fluorine. In aspects, $R^{23}$ is independently —$CF_3$. In aspects, $R^{23}$ is independently —$CHF_2$. In aspects, $R^{23}$ is independently —$CH_2F$. In aspects, $R^{23}$ is independently ethyl substituted with at least one fluorine. In aspects, $R^{23}$ is independently propyl substituted with at least one fluorine. In aspects, $R^{23}$ is independently butyl substituted with at least one fluorine.

In aspects, $R^{24}$ is independently hydrogen. In aspects, $R^{24}$ is independently fluorine. In aspects, $R^{24}$ is independently $C_1$-$C_4$ alkyl substituted with at least one fluorine. In aspects, $R^{24}$ is independently methyl substituted with at least one fluorine. In aspects, $R^{24}$ is independently —$CF_3$. In aspects, $R^{24}$ is independently —$CHF_2$. In aspects, $R^{24}$ is independently —$CH_2F$. In aspects, $R^{24}$ is independently ethyl substituted with at least one fluorine. In aspects, $R^{24}$ is independently npropyl substituted with at least one fluorine. In aspects, $R^{24}$ is independently butyl substituted with at least one fluorine.

In aspects, $R^{20}$ and $R^{24}$ are hydrogen; and $R^{21}$, $R^{22}$, and $R^{23}$ are fluorine. In aspects, at least one of $R^{20}$, $R^{21}$, $R^{22}$, $R^{23}$, and $R^{24}$ is fluorine or $C_1$-$C_2$ alkyl substituted with at least one fluorine. In aspects, $R^{20}$, $R^{21}$, $R^{22}$, $R^{23}$, and $R^{24}$ are each independently hydrogen, fluorine, or methyl substituted with at least one fluorine. In aspects, at least one of $R^{20}$, $R^{21}$, $R^{22}$, $R^{23}$, and $R^{24}$ is fluorine. In aspects, at least one of $R^{20}$, $R^{21}$, $R^{22}$, $R^{23}$, and $R^{24}$ is methyl substituted with at least one fluorine. In aspects, at least one of $R^{20}$, $R^{21}$, $R^{22}$, $R^{23}$, and $R^{24}$ is ethyl substituted with at least one fluorine. In aspects, $R^{20}$, $R^{21}$, and $R^{24}$ are hydrogen; and $R^{22}$ and $R^{23}$ are fluorine. In aspects, $R^{20}$, $R^{21}$, $R^{23}$, and $R^{24}$ are hydrogen, and $R^{22}$ is —$CF_3$.

In aspects, $R^{20}$, $R^{21}$, $R^{23}$, and $R^{24}$ are hydrogen and $R^{22}$ is fluorine. In aspects, $R^{20}$, $R^{21}$, $R^{22}$, and $R^{24}$ are hydrogen and $R^{23}$ is fluorine. In aspects, $R^{20}$, $R^{21}$, $R^{22}$, and $R^{23}$ are hydrogen and $R^{24}$ is fluorine. In aspects, $R^{20}$, $R^{21}$, $R^{22}$, and $R^{24}$ are hydrogen and $R^{23}$ is —$CF_3$. In aspects, $R^{20}$, $R^{21}$, $R^{22}$, and $R^{23}$ are hydrogen and $R^{24}$ is —$CF_3$.

In aspects, $R^{20}$, $R^{21}$, and $R^{24}$ are hydrogen and $R^{22}$ and $R^{23}$ are fluorine. In aspects, $R^{20}$, $R^{21}$, and $R^{23}$ are hydrogen and $R^{22}$ and $R^{24}$ are fluorine. In aspects, $R^{20}$, $R^{22}$, and $R^{24}$ are hydrogen and $R^{21}$ and $R^{23}$ are fluorine. In aspects, $R^{20}$, $R^{22}$, and $R^{23}$ are hydrogen and $R^{21}$ and $R^{24}$ are fluorine. In aspects, $R^{20}$, $R^{22}$, and $R^{24}$ are hydrogen and $R^{20}$ and $R^{24}$ are fluorine. In aspects, $R^{22}$, $R^{23}$, and $R^{24}$ are hydrogen and $R^{20}$ and $R^{21}$ are fluorine.

In aspects, $R^{20}$ and $R^{21}$ are hydrogen and $R^{22}$, $R^{23}$, and $R^{24}$ are fluorine. In aspects, $R^{20}$ and $R^{22}$ are hydrogen and $R^{21}$, $R^{23}$, and $R^{24}$ are fluorine. In aspects, $R^{21}$ and $R^{22}$ are hydrogen and $R^{20}$, $R^{23}$, and $R^{24}$ are fluorine.

In aspects, $R^{20}$ is hydrogen and $R^{21}$, $R^{22}$, $R^{23}$, and $R^{24}$ are fluorine. In aspects, $R^{21}$ is hydrogen and $R^{20}$, $R^{22}$, $R^{23}$, and $R^{24}$ are fluorine. In aspects, $R^{22}$ is hydrogen and $R^{20}$, $R^{21}$, $R^{23}$, and $R^{24}$ are fluorine.

$R^{30}$, $R^{31}$, $R^{32}$, $R^{33}$, $R^{34}$, and $R^{35}$ are each independently —$CH_3$ or —$CF_3$. In aspects, $R^{30}$, $R^{31}$, $R^{32}$, $R^{33}$, $R^{34}$, and $R^{35}$ are each —$CH_3$. In aspects, $R^{30}$, $R^{31}$, $R^{32}$, $R^{33}$, $R^{34}$, and $R^{35}$ are each —$CF_3$.

In embodiments, a fluorosilicone polymer is synthesized from a base polymer that is hydride terminated polyphenyl-(dimethylyhdrosiloxy)siloxane of Formula (II):

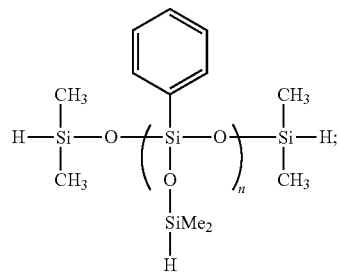

(II)

wherein n is as defined herein for the compound of Formula (I). In aspects, the polymer is synthesized by reacting the compound of Formula (II) with a compound of Formula (III), a compound of Formula (E), a compound of Formula (D), a compound of Formula (D1), a compound of Formula (D2), or a compound of Formula (D3).

In embodiments, a symmetric fluorosilicone copolymer is synthesized from a base polymer that is side-chain terminated with hydride functionality. A hydride chain end-terminated poly(dimethyl siloxane) such as methylhydrosiloxane-dimethylsiloxane copolymer, trimethylsiloxane terminated (HMS-082) according to Formula (IV). Various fluorinated-containing compounds can be used to balance the refractive index and solubility properties.

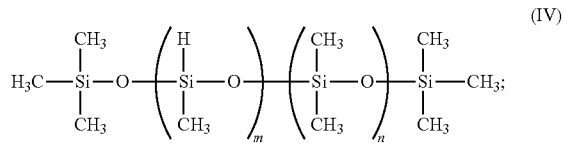

(IV)

wherein n is as defined herein for the compound of Formula (I), Formula (A), and Formula (B). In aspects, the polymer is synthesized by reacting the compound of Formula (IV) with a compound of Formula (III), a compound of Formula (E), a compound of Formula (D), a compound of Formula (D1), a compound of Formula (D2), or a compound of Formula (D3).

In embodiments, a fluorophenyl copolymer is synthesized using a compound of Formula (VII) and modifying by adding fluoro functional groups such as stable, short chain fluoro alkanes to a co-hydride-phenyl base polymer. The solubility and refractive properties may be balanced by the amount of fluoro in one section of the copolymer and the percentage of that section of the overall polymer. As with other approaches, the fluoro content of the functional group may be adjusted if the RI is too high or too low, the hydride concentration of the base polymer may be varied if too soluble, and the molecular weight of the base polymer varied to adjust the viscosity.

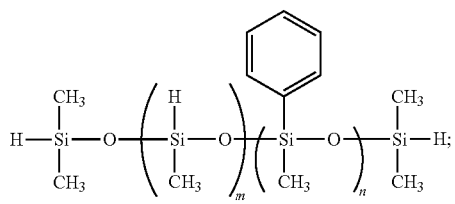

(VII)

wherein n is as defined herein for the compound of Formula (I), Formula (A), and Formula (B). In aspects, the polymer is synthesized by reacting the compound of Formula (VII) with a compound of Formula (III), a compound of Formula (E), a compound of Formula (D), a compound of Formula (D1), a compound of Formula (D2), or a compound of Formula (D3).

In embodiments, the fluorosilicone polymer or copolymer has purely hydrocarbon functionality, but the elastomer has the blend of fluorine groups and hydrocarbon groups that match optical properties while maintaining chemical inertness. It should be appreciated that the liquid optical material does not need to be similar. The liquid optical material can be optically matched and chemically independent of the silicone elastomer, for example propylene glycol.

Any of a variety of stable, short chain fluoroalkanes, such as the compound of Formula (III) or Formula (E), can be added to create a molecule that balances the refractive index and solubility parameters within each repeat unit. The fluoro content of the functional groups can be adjusted to increase or decrease the refractive index of the final product. The molecular weight of the base polymer may also be varied to adjust viscosity. Alternatively, a fluorofunctionalized cyclic aromatic according to Formula (D), (D1), (D2), or D3) may be added to balance the refractive index and solubility parameters.

The compound of Formula (III) is:

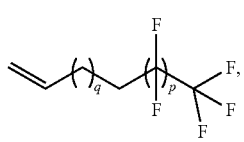

(III)

wherein p and q are each independently an integer from 1 to 5.

The compound of Formula (E) is:

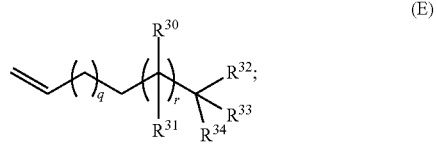

(E)

wherein q and r are each independently an integer from 0 to 6; and $R^{30}$, $R^{31}$, $R^{32}$, $R^{33}$, and $R^{34}$ are each independently hydrogen, fluorine, or $C_1$-$C_4$ alkyl substituted with at least one fluorine; provided that $R^{30}$, $R^{31}$, $R^{32}$, $R^{33}$, and $R^{34}$ are not all hydrogen.

The compound of Formula (D) is:

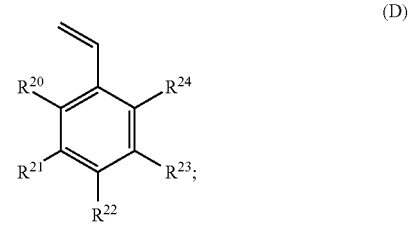

(D)

wherein $R^{20}$, $R^{21}$, $R^{22}$, $R^{23}$, and $R^{24}$ are as defined herein.

The compounds of Formula (D1), (D2), and (D3) are:

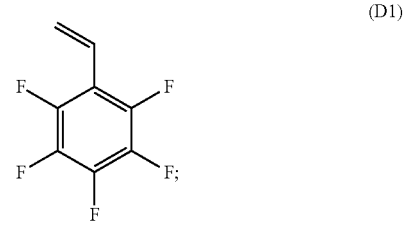

(D1)

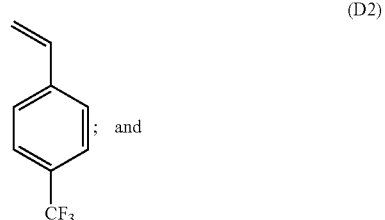

(D2)

; and

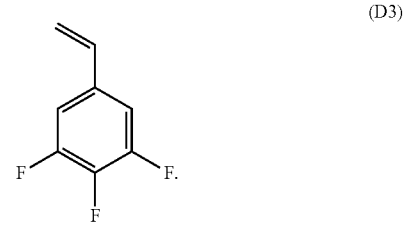

(D3)

In aspects, the compound of Formula (II) is reacted with the compound of Formula (III) or a compound of Formula (D) to produce a fluorosilicone polymer of Formula (VIII):

(VIII)

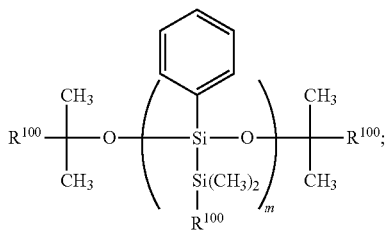

wherein $R^{100}$ is

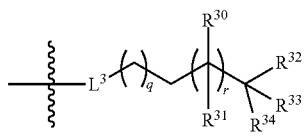

(when the reactant is a compound of Formula (III)) or

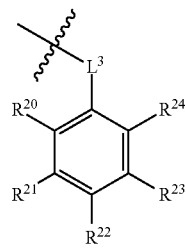

(when the reactant is a compound of Formula (D)); wherein $L^3$ is independently —$(CH_2)_2$— or —$CH(CH_3)$—, $R^{30}$, $R^{31}$, $R^{32}$, $R^{33}$, $R^{34}$, q, r, m, $R^{20}$, $R^{21}$, $R^{22}$, $R^{23}$, $R^{24}$ are are as defined herein.

In aspects, the compound of Formula (IV) is reacted with the compound of Formula (III) or a compound of Formula (D) to produce a fluorosilicone copolymer of Formula (IX):

(IX)

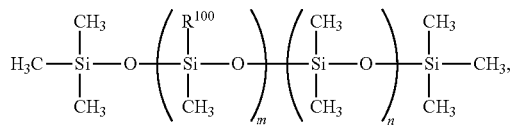

wherein $R^{100}$, m, and n are as defined herein.

In aspects, the compound of Formula (VII) is reacted with the compound of Formula (III) or a compound of Formula (D) to produce a fluorosilicone copolymer of Formula (X):

(X)

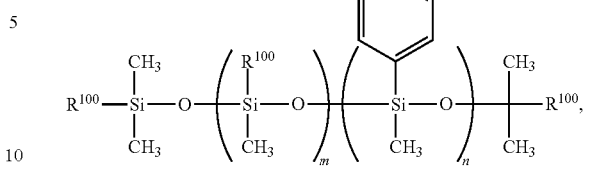

wherein $R^{100}$, m, and n are as defined herein.

In aspects, the liquid optical material is a silicone copolymer of any one of Formula (I), Formula (A), or Formula (B), wherein the m unit of the copolymer is identified as the "phenyl" content and the n unit of the copolymers is identified as the fluoro content. In aspects, the copolymer is a silicone oil having greater than 20% fluoro content up to about 60% fluoro content to drive down the RI. In aspects, the fluoro content of the silicone oil can be between 30% to about 50%. This range in fluoro content of the liquid optical material can provide sufficient chemical dissimilarity relative to the material of the solid lens components (e.g., PDMS). In aspects, the liquid optical material also has greater than about 1.0% up to about 10% phenyl content to provide index-matching with the material of the solid lens components (e.g., PDMS). In aspects, the phenyl content of the silicone oil can be between about 1.5% to about 5%. In aspects, the liquid optical material is a silicone oil having a fluoro content that is greater than 20% and a phenyl content that is greater than 1.5%. In aspects, the liquid optical material is a silicone oil having a fluoro content that is greater than 40% and a phenyl content that is greater than 5%.

In aspects, the liquid optical material is a silicone oil having greater than about 20% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 25% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 30% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 35% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 40% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 45% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 50% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 55% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 60% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 65% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content. In some implementations, the liquid optical material is a silicone oil having greater than about 70% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 75% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 80% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 85% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 90% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having greater than about 95% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

In aspects, the liquid optical material is a silicone oil having about 100% fluoro content and having greater than about 1% phenyl content, or greater than about 1.5% phenyl content, or greater than about 2% phenyl content, or greater than about 2.5% phenyl content, or greater than about 3% phenyl content, or greater than about 3.5% phenyl content, or greater than about 4% phenyl content, or greater than about 4.5% phenyl content, or greater than about 5% phenyl content, or greater than about 5.5% phenyl content, or greater than about 6% phenyl content, or greater than about 6.5% phenyl content, or greater than about 7% phenyl content, or greater than about 7.5% phenyl content, or greater than about 8% phenyl content, or greater than about 8.5% phenyl content, or greater than about 9% phenyl content, or greater than about 9.5% phenyl content, or greater than about 10% phenyl content, or greater than about 20% phenyl content, or greater than about 30% phenyl content, or greater than about 40% phenyl content, or greater than about 50% phenyl content.

Compositions

In an aspect is provided a liquid optical material. The liquid optical material is alternatively referred to herein as a "composition." The liquid optical material comprises the fluorosilicone polymers and/or copolymers described herein. For example, the composition can comprise a plurality of the copolymers of Formula (I), Formula (A), Formula (B), or any one of the polymers or copolymers of Formula (VII)-(XVI). In aspects, the composition comprises a plurality of the copolymer of Formula (I). In aspects, the composition comprises a plurality of the copolymer of Formula (A). In aspects, the composition comprises a plurality of the copolymer of Formula (B).

For purposes of the disclosure, the phrase "a composition comprising a plurality of the copolymer of Formula (I)" is equivalent to the phrase "a composition comprising the copolymer of Formula (I)." Similarly, the phrase "a composition comprising a plurality of the copolymer of Formula (A)" is equivalent to the phrase "a composition comprising the copolymer of Formula (A)." Similarly, the phrase "a composition comprising a plurality of the copolymer of Formula (B)" is equivalent to the phrase "a composition comprising the copolymer of Formula (B)." This language is similarly applicable to the polymers and copolymers of Formula (VII) to (XVI).

In addition to comprising a plurality of the copolymer of Formula (I), Formula (A), Formula (B), or any one of Formula (VII)-(XVI), the composition may further comprise one or more impurities. An "impurity" is any undesirable compound present in the composition that is used in a lens. For example, impurities include catalysts and/or a reactants (e.g., starting materials such as the compounds of Formula (E) and (D)) used to produce the copolymers and/or reaction products (e.g., any polymer or copolymer that falls outside the scope of the copolymer of Formula (I), Formula (A), Formula (B), or any one of Formula (VII)-(XVI) that is intended to be produced). For example, an impurity could be a copolymer (i.e., a reaction product) that has a molecular weight higher than or lower than the desired molecular weight of the copolymer of Formula (I), Formula (A), Formula (B), or any one of Formula (VII)-(XVI). For example, a compound having a molecular weight less than the molecular weight of the desired copolymer is an impurity (i.e., undesirable) because it could swell the silicone elastomer of the lens. A compound having a molecular weight greater than the molecular weight of the desired copolymer is an impurity (i.e., undesirable) because it could increase the viscosity of the composition.

In aspects, the disclosure provides a composition comprising the copolymer of Formula (I) and one or more impurities. In aspects, the disclosure provides a composition comprising the copolymer of Formula (A) and one or more impurities. In aspects, the disclosure provides a composition comprising the copolymer of Formula (B) and one or more impurities. In aspects, the disclosure provides a composition comprising the copolymer of any one of Formula (VII)-(XVI) and one or more impurities.

When an impurity is present in the composition, the impurity is present in an amount of about 25 wt % or less of the total amount of the composition. In aspects, the impurity is present in an amount of about 20 wt % or less. In aspects, the impurity is present in an amount of about 15 wt % or less. In aspects, the impurity is present in an amount of about 10 wt % or less. In aspects, the impurity is present in an amount of about 9 wt % or less. In aspects, the impurity is present in an amount of about 8 wt % or less. In aspects, the impurity is present in an amount of about 7 wt % or less. In aspects, the impurity is present in an amount of about 6 wt % or less. In aspects, the impurity is present in an amount of about 5 wt % or less. In aspects, the impurity is present in an amount of about 4.5 wt % or less. In aspects, the impurity is present in an amount of about 4 wt % or less In aspects, the impurity is present in an amount of about 3.5 wt % or less. In aspects, the impurity is present in an amount of about 3 wt % or less. In aspects, the impurity is present in an amount of about 2.5 wt % or less. In aspects, the impurity is present in an amount of about 2 wt % or less. In aspects, the impurity is present in an amount of about 1.5 wt % or less. In aspects, the impurity is present in an amount of about 1 wt % or less. In aspects, the impurity is present in an amount of about 0.5 wt % or less. In aspects, the impurity is present in an amount of about 0.1 wt % or less.

The liquid optical material is substantially index-matched to the solid optical component. A fully fluorinated silicone polymer such as polydiperfluoromethylsilicone or poly(dimethylsiloxane) (PDMS) has a refractive index that is less than that of silicone chain with full hydrocarbon functionality. PDMS has a refractive index of 1.40 and phenyl functionality increases the refractive index. Where the solid elastomeric components of the lens body are PDMS, the liquid optical material can be a polymer having both a fluorinated functionality for chemical properties and a hydrocarbon functionality for optical properties.

The refractive index of the liquid optical material is preferably a refractive index between the refractive index of the diphenyl silicones and the fluorosilicones. In aspects, the liquid optical material has a refractive index from about 1.40 to about 1.50. In aspects, the liquid optical material has a refractive index from about 1.41 to about 1.49. In aspects, the liquid optical material has a refractive index from about 1.41 to about 1.48. In aspects, the liquid optical material has a refractive index from about 1.41 to about 1.47. In aspects, the liquid optical material has a refractive index from about 1.41 to about 1.46. In aspects, the liquid optical material has a refractive index from about 1.42 to about 1.48. In aspects, the liquid optical material has a refractive index from about 1.43 to about 1.47. In aspects, the liquid optical material has a refractive index from about 1.43 to about 1.46. In aspects, the liquid optical material has a refractive index from about 1.43 to about 1.46. In aspects, the liquid optical material has a refractive index from about 1.43 to about 1.45. In aspects, the liquid optical material has a refractive index from about 1.44 to about 1.46. In aspects, the liquid optical material has a refractive index of between 1.41 and 1.46. The refractive index of the liquid optical material can be tuned to between 1.41 or 1.46, or between 1.43 to about 1.45. The refractive index is measured with a refractometer at 20° C. Tuning as used herein means modifying relevant functional groups onto, for example, vinyl terminated and vinyl functionalized silicone polymers producing a functionalized silicone-based polymer having a desired refractive index and/or solubility.

In aspects, the liquid optical material has a light transmittance of at least 80% in the visible range of 400 nm to 700 nm. In aspects, the liquid optical material has a light transmittance of at least 85% in the visible range of 400 nm to 700 nm. In aspects, the liquid optical material has a light transmittance of at least 90% in the visible range of 400 nm to 700 nm. In aspects, the liquid optical material has a light transmittance of at least 91% in the visible range of 400 nm to 700 nm. In aspects, the liquid optical material has a light transmittance of at least 92% in the visible range of 400 nm to 700 nm. In aspects, the liquid optical material has a light transmittance of at least 93% in the visible range of 400 nm to 700 nm. In aspects, the liquid optical material has a light transmittance of at least 94% in the visible range of 400 nm to 700 nm. In aspects, the liquid optical material has a light transmittance of at least 95% in the visible range of 400 nm to 700 nm. In aspects, the liquid optical material has a light transmittance of at least 96% in the visible range of 400 nm to 700 nm. In aspects, the liquid optical material has a light transmittance of at least 97% in the visible range of 400 nm to 700 nm. In aspects, the liquid optical material has a light transmittance of at least 98% in the visible range of 400 nm to 700 nm. In aspects, the liquid optical material has a light transmittance of at least 99% in the visible range of 400 nm to 700 nm. In aspects, the liquid optical material is substantially free of scattering particulate. In aspects, the liquid optical material has a 95% transmittance within visible 400-700 nm and is substantially free of scattering particulate. The light transmittance is measured with a UV-Vis spectrophotometer.

In embodiments, the liquid optical material has a viscosity between 10 cP and 50,000 cP. In aspects, the liquid optical material has a viscosity from about 100 cP to about 20,000 cP. In aspects, the liquid optical material has a viscosity from about 100 cP to about 10,000 cP. In aspects, the liquid optical material has a viscosity from about 500 cP to about 5,000 cP. In aspects, the liquid optical material has a viscosity from about 500 cP to about 4,000 cP. In aspects, the liquid optical material has a viscosity from about 500 cP to about 3,000 cP. In aspects, the liquid optical material has a viscosity from about 500 cP to about 2,500 cP. In aspects, the liquid optical material has a viscosity from about 1,000 cP to about 2,000 cP. Viscosity is measured, e.g., with a Brookfield Viscometer at room temperature. In aspects, room temperature is from about 18° C. to about 22° C. In aspects, room temperature is 20° C.

The liquid optical material does not swell silicone lenses (e.g., PDMS or poly(di-n-pentylsilylene)) more than about 5%. In aspects, liquid optical material does not swell silicone lenses more than about 4%. In aspects, liquid optical material does not swell silicone lenses more than about 3%. In aspects, liquid optical material does not swell silicone lenses more than about 2%. In aspects, liquid optical material does not swell silicone lenses more than about 1%. In aspects, liquid optical material does not swell silicone lenses more than 0.5%. The liquid optical material is non-hygroscopic and maintains a volume when in aqueous environment.

Lenses

Provided herein is a lens comprising: (i) an anterior portion comprising a refractive optical element; (ii) a posterior portion; and (iii) an enclosed cavity between the anterior portion and the posterior portion, wherein the enclosed cavity comprises a copolymer described herein. In aspects, the copolymer is of Formula (I). In aspects, the copolymer is of Formula (A). In aspects, the copolymer is of Formula (B). In aspects, the lens is a photographic lens (e.g., a camera lens). In aspects, the lens is a magnification lens. Exemplary magnification lenses include eyeglass lenses, contact lenses, camera lenses, imagining lenses, microscope lenses, telescope lenses, monocular lenses, binocular lenses, projector lenses, spotting scope lenses, telescopic gun sight lenses, theodolite lenses, medical equipment lenses, and the like. In aspects, the lens is a contact lens. In aspects, the lens is an intraocular lens. In aspects, the lens is a concave lens. In aspects, the lens is a convex lens. In embodiments, the anterior portion and the posterior portion comprise a silicone elastomer.

In an aspect is provided lens comprising: (i) an anterior portion comprising a refractive optical element; (ii) a posterior portion; and (iii) an enclosed cavity between the anterior portion and the posterior portion, wherein the enclosed cavity comprises a liquid optical material described herein. In aspects, the liquid optical material comprises a plurality of the copolymer of Formula (I). In aspects, the liquid optical material comprises a plurality of the copolymer of Formula (A). In aspects, the liquid optical material comprises a plurality of the copolymer of Formula (B). In aspects, the lens is a photographic lens (e.g., a camera lens). In aspects, the lens is a magnification lens. Exemplary magnification lenses include eyeglass lenses, contact lenses, camera lenses, imagining lenses, microscope lenses, telescope lenses, monocular lenses, binocular lenses, projector lenses, spotting scope lenses, telescopic gun sight lenses, theodolite lenses, medical equipment lenses, and the like. In aspects, the lens is a contact lens. In aspects, the lens is an intraocular lens. In aspects, the lens is a concave lens. In aspects, the lens is a convex lens. In embodiments, the anterior portion and the posterior portion comprise a silicone elastomer.

In embodiments, the intraocular lens has the structure and/or components described in detail in other sections of the disclosure. In each embodiment or aspect, the lens described therein can contain the liquid optical material described herein.

In an aspect is provided a method for treating a cataract in an eye of a patient in need thereof, the method comprising inserting an intraocular lens described herein into the eye of the patient. Methods for inserting an intraocular lens in a patient's eye are well-known in the art.

Methods of Making Copolymers

In an aspect is a process for producing a polymer or copolymer described herein, the process including: (i) contacting an $R^{60}$-substituted alkyl or an $R^{60}$-substituted aryl with a copolymer of Formula (C) to produce a composition including the copolymer of Formula (I), (A) or (B); and (ii) removing impurities from the composition; thereby producing the copolymer of Formula (I), (A), or (B).

$R^{60}$ is independently fluorine, $R^{61}$-substituted alkyl (e.g., $C_1$-$C_8$, $C_1$-$C_6$, $C_1$-$C_4$, or $C_1$-$C_2$), $R^{61}$-substituted heteroalkyl (e.g., 2 to 8 membered, 2 to 6 membered, 4 to 6 membered, 2 to 3 membered, or 4 to 5 membered), $R^{61}$-substituted aryl (e.g., $C_6$-$C_{10}$ or phenyl), or $R^{61}$-substituted heteroaryl (e.g., 5 to 10 membered, 5 to 9 membered, or 5 to 6 membered); and $R^{61}$ is independently fluorine. In aspects, $R^{60}$ is independently fluorine, $R^{61}$-substituted alkyl, $R^{61}$-substituted heteroalkyl, $R^{61}$-substituted aryl, or $R^{61}$-substituted heteroaryl. $R^{61}$ is independently fluorine. In aspects, $R^{60}$ is independently $R^{61}$-substituted alkenyl; and $R^{61}$ is independently fluorine.

In aspects, $R^{60}$ is independently fluorine. In aspects, $R^{60}$ is independently $C_1$-$C_6$ alkyl substituted with at least one fluorine. In aspects, $R^{60}$ is independently methyl substituted with at least one fluorine. In aspects, $R^{60}$ is independently —$CF_3$. In aspects, $R^{60}$ is independently —$CHF_2$. In aspects, $R^{60}$ is independently —$CH_2F$. In aspects, $R^{60}$ is independently ethyl substituted with at least one fluorine. In aspects, $R^{60}$ is independently propyl substituted with at least one fluorine. In aspects, $R^{60}$ is independently butyl substituted with at least one fluorine.

The copolymer of Formula (C) is:

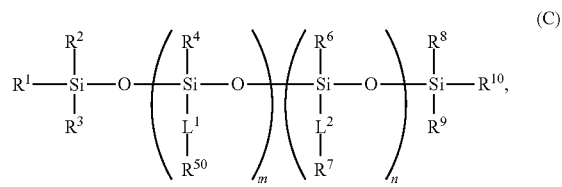

(C)

wherein $R^1$, $R^2$, $R^3$, $R^4$, $R^6$, $R^7$, $R^8$, $R^9$, $R^{10}$, $L^1$, $L^2$, m, and n are as described herein for the compounds of Formula (I) and Formula (A).

$R^{50}$ is hydrogen, substituted or unsubstituted alkyl, or substituted or unsubstituted aryl. In aspects, $R^{50}$ is hydrogen, substituted or unsubstituted alkyl (e.g., $C_1$-$C_8$, $C_1$-$C_6$, $C_1$-$C_4$, or $C_1$-$C_2$), or substituted or unsubstituted aryl (e.g., $C_6$-$C_{10}$ or phenyl). In aspects, $R^{50}$ is independently unsubstituted methyl. In aspects, $R^{50}$ is independently unsubstituted ethyl. In aspects, $R^{50}$ is independently unsubstituted propyl. In aspects, $R^{50}$ is independently unsubstituted propyl. In aspects, $R^{50}$ is independently unsubstituted butyl. In aspects, $R^{50}$ is independently unsubstituted phenyl. In aspects, $R^{50}$ is independently unsubstituted naphthyl.

Impurities are removed from the composition using organic solvents or solvent mixtures to separate unwanted moieties from desired moieties. The removal and separation of impurities can be on the basis of chemical makeup (i.e. functional groups) or molecular weight of the moieties.

In aspects, removing impurities from the composition includes washing the composition with an organic solvent to remove impurities from the composition. In aspects, the organic solvent is dimethylsulfoxide (DMSO), dimethylformamide (DMF), acetonitrile, dimethylacetamide (DMA), acetone, tetrahydrofuran, dioxane, N-methyl-2-pyrrolidone (NMP), diethylether, methanol, ethanol, isopropanol, pyridine, acetic acid, triethylamine (TEA), diisopropylethylamine (DIPEA), carbon tetrachloride, chloroform, dichloromethane, water, $D_2O$, hexane, cyclohexane, pentane, 2-methylpentane, 3-methylpentane, 2,3-dimethylbutane, 2,2-dimethylbutane, heptane, octane, xylene, benzene, toluene, or a combination of two or more thereof. In aspects, the organic solvent is hexane. In aspects, the organic solvent is dichloromethane. In aspects, the organic solvent is a mixture of hexane and dichloromethane. In aspects, the organic solvent is a mixture of hexane and DMSO. In aspects, the organic solvent is a mixture of hexane and DMF. In aspects, the organic solvent is a mixture of hexane and DMA.

In aspects, removing impurities from the composition includes washing the composition with a liquid hydrocarbon to remove impurities from the composition. In aspects, the liquid hydrocarbon is hexane, cyclohexane, pentane, 2-methylpentane, 3-methylpentane, 2,3-dimethylbutane, 2,2-dimethylbutane, heptane, octane, xylene, benzene, or toluene. In aspects, the liquid hydrocarbon is hexane. In aspects, the liquid hydrocarbon is cyclohexane. In aspects, the liquid hydrocarbon is pentane. In aspects, the liquid hydrocarbon is 2-methylpentane. In aspects, the liquid hydrocarbon is 3-methylpentane. In aspects, the liquid hydrocarbon is 2,3-dimethylbutane. In aspects, the liquid hydrocarbon is 2,2-dimethylbutane. In aspects, the liquid hydrocarbon is heptane. In aspects, the liquid hydrocarbon is octane. In aspects, the liquid hydrocarbon is xylene. In aspects, the liquid hydrocarbon is benzene. In aspects, the liquid hydrocarbon is toluene.

In aspects, removing impurities from the composition includes extracting impurities from the composition with supercritical $CO_2$.

In aspects, the process includes washing the composition at least once. In aspects, the process includes washing the composition at least 2 times. In aspects, the process includes washing the composition at least 3 times. In aspects, the process includes washing the composition at least 4 times. In aspects, the process includes washing the composition at least 5 times. In aspects, the process includes washing the composition at least 6 times. In aspects, the process includes washing the composition at least 7 times. In aspects, the process includes washing the composition at least 8 times. In aspects, the process includes washing the composition at least 9 times. In aspects, the process includes washing the composition at least 10 times. In aspects, the process includes washing the composition at least 11 times. In aspects, the process includes washing the composition at least 12 times. In aspects, the process includes washing the composition at least 13 times. In aspects, the process includes washing the composition at least 14 times. In aspects, the process includes washing the composition at least 15 times. In aspects, the process includes washing the composition at least 16 times. In aspects, the process includes washing the composition at least 17 times. In aspects, the process includes washing the composition at least 18 times. In aspects, the process includes washing the composition at least 19 times. In aspects, the process includes washing the composition at least 20 times.

In aspects, removing impurities from the composition includes contacting the composition with a silicone elastomer. In aspects, the contacting occurs at a temperature from about 25° C. to about 300° C. In aspects, the contacting occurs at a temperature from about 50° C. to about 250° C. In aspects, the contacting occurs at a temperature from about 60° C. to about 125° C. In aspects, the contacting occurs at a temperature from about 70° C. to about 110° C. In aspects, the contacting occurs at a temperature from about 80° C. to about 100° C. In aspects, the contacting occurs by placing the composition in contact with the silicone elastomer from about 1 minute to about 1 hour. The silicone elastomer can be any known in the art. In aspects, the silicone elatomer is the same silicone elastomer that will be used to form the lens in which the composition will be enclosed. As discussed throughout, the liquid optical material does not interact with the silicone elastomer of the lens. As such, contacting the composition with a silicone elastomer will allow impurities (e.g., low molecular weight copolymers or reactants) to from a covalent or non-covalent bond with the silicone elastomer, so that they can be removed from the final composition before it is used as the liquid optical material in the lens. In aspects, the step of contacting the composition with a silicone elastomer is performed after the step of washing the composition.

In aspects, step (i) includes contacting $R^{60}$-substituted aryl with a copolymer of Formula (C) to produce a composition comprising the copolymer of Formula (I), (A), or (B); wherein $R^{60}$ is fluorine or $C_1$-$C_6$ alkyl substituted with at least one fluorine.

In aspects, $R^{60}$-substituted aryl is a compound of Formula (D):

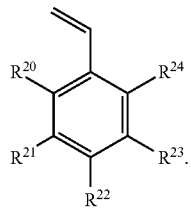

(IV)

$R^{20}$, $R^{21}$, $R^{22}$, $R^{23}$, and $R^{24}$ are as described herein. In aspects, $R^{20}$, $R^{21}$, $R^{22}$, $R^{23}$, and $R^{24}$ are each independently hydrogen, fluorine, or $C_1$-$C_4$ alkyl substituted with at least one fluorine; provided that $R^{20}$, $R^{21}$, $R^{22}$, $R^{23}$, and $R^{24}$ are not all hydrogen.

In aspects, the compound of Formula (D) is a compound of Formula (D1), (D2), or (D3):

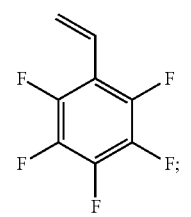

(D1)

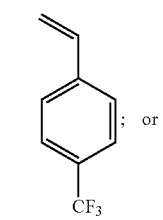

(D2)

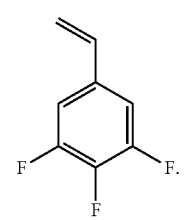

(D3)

In aspects, step (i) includes contacting $R^{60}$-substituted alkyl with a copolymer of Formula (C) to produce a composition comprising the copolymer of Formula (I), (A), or (B); wherein $R^{60}$ is fluorine or $C_1$-$C_6$ alkyl substituted with at least one fluorine.

In aspects, $R^{60}$-substituted alkyl is a compound of Formula (V):

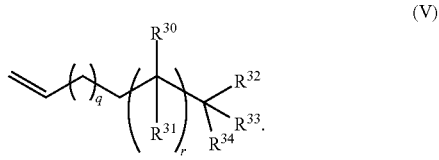

(V)

q and r are each independently an integer from 0 to 6; and $R^{30}$, $R^{31}$, $R^{32}$, $R^{33}$, and $R^{34}$ are each independently hydrogen, fluorine, or $C_1$-$C_4$ alkyl substituted with at least one fluorine; provided that $R^{30}$, $R^{31}$, $R^{32}$, $R^{33}$, and $R^{34}$ are not all hydrogen.

In aspects, $R^{30}$ is independently hydrogen. In aspects, $R^{30}$ is independently fluorine. In aspects, $R^{30}$ is independently $C_1$-$C_4$ alkyl substituted with at least one fluorine. In aspects, $R^{30}$ is independently methyl substituted with at least one fluorine. In aspects, $R^{30}$ is independently —$CF_3$. In aspects, $R^{30}$ is independently —$CHF_2$. In aspects, $R^{30}$ is independently —$CH_2F$. In aspects, $R^{30}$ is independently ethyl substituted with at least one fluorine. In aspects, $R^{30}$ is independently n-propyl substituted with at least one fluorine. In aspects, $R^{30}$ is independently isopropyl substituted with at least one fluorine. In aspects, $R^{30}$ is independently n-butyl substituted with at least one fluorine. In aspects, $R^{30}$ is independently tert-butyl substituted with at least one fluorine.

In aspects, $R^{31}$ is hydrogen. In aspects, $R^{31}$ is fluorine. In aspects, $R^{31}$ is $C_1$-$C_4$ alkyl substituted with at least one fluorine. In aspects, $R^{31}$ is methyl substituted with at least one fluorine. In aspects, $R^{31}$ is —$CF_3$. In aspects, $R^{31}$ is —$CHF_2$. In aspects, $R^{31}$ is —$CH_2F$. In aspects, $R^{31}$ is ethyl substituted with at least one fluorine. In aspects, $R^{31}$ is n-propyl substituted with at least one fluorine. In aspects, $R^{31}$ is isopropyl substituted with at least one fluorine. In aspects, $R^{31}$ is n-butyl substituted with at least one fluorine. In aspects, $R^{31}$ is tert-butyl substituted with at least one fluorine.

In aspects, $R^{32}$ is hydrogen. In aspects, $R^{32}$ is fluorine. In aspects, $R^{32}$ is $C_1$-$C_4$ alkyl substituted with at least one fluorine. In aspects, $R^{32}$ is methyl substituted with at least one fluorine. In aspects, $R^{32}$ is —$CF_3$. In aspects, $R^{32}$ is —$CHF_2$. In aspects, $R^{32}$ is —$CH_2F$. In aspects, $R^{32}$ is ethyl substituted with at least one fluorine. In aspects, $R^{32}$ is n-propyl substituted with at least one fluorine. In aspects, $R^{32}$ is isopropyl substituted with at least one fluorine. In aspects, $R^{32}$ is n-butyl substituted with at least one fluorine. In aspects, $R^{32}$ is tert-butyl substituted with at least one fluorine.

In aspects, $R^{33}$ is hydrogen. In aspects, $R^{33}$ is fluorine. In aspects, $R^{33}$ is $C_1$-$C_4$ alkyl substituted with at least one fluorine. In aspects, $R^{33}$ is methyl substituted with at least one fluorine. In aspects, $R^{33}$ is —$CF_3$. In aspects, $R^{33}$ is —$CHF_2$. In aspects, $R^{33}$ is —$CH_2F$. In aspects, $R^{33}$ is ethyl substituted with at least one fluorine. In aspects, $R^{33}$ is n-propyl substituted with at least one fluorine. In aspects, $R^{33}$ is isopropyl substituted with at least one fluorine. In aspects, $R^{33}$ is n-butyl substituted with at least one fluorine. In aspects, $R^{33}$ is tert-butyl substituted with at least one fluorine.

In aspects, $R^{34}$ is hydrogen. In aspects, $R^{34}$ is fluorine. In aspects, $R^{34}$ is $C_1$-$C_4$ alkyl substituted with at least one fluorine. In aspects, $R^{34}$ is methyl substituted with at least one fluorine. In aspects, $R^{34}$ is —$CF_3$. In aspects, $R^{34}$ is —$CHF_2$. In aspects, $R^{34}$ is —$CH_2F$. In aspects, $R^{34}$ is ethyl substituted with at least one fluorine. In aspects, $R^{34}$ is n-propyl substituted with at least one fluorine. In aspects, $R^{34}$ is isopropyl substituted with at least one fluorine. In aspects, $R^{34}$ is n-butyl substituted with at least one fluorine. In aspects, $R^{34}$ is tert-butyl substituted with at least one fluorine.

Lenses

The fluorosilicone copolymers described herein may be incorporated within a fluid chamber of a lens as the liquid optical material. The combinations of liquid optical materials and solid optical components are useful for designing a stable, optically superior lens regardless the configuration of the lens. The lens incorporating the liquid optical materials can vary in configuration and location of implantation. For example, the lens can be a non-shape changing IOL or the lens can be a shape changing IOL. The IOL can be configured for implantation, fully or in part, within the capsular bag. The IOL can be configured for implantation, fully or in part, outside the capsular bag such as within the ciliary sulcus. Described below are examples of an IOL having a liquid optical material contained within a solid optical component. However, it should be appreciated that any of a variety of IOL system is considered herein. The lenses described herein with respect to FIGS. 4A-4F, 5A-5F, and 6A-6C are examples of lenses incorporating a fluid chamber that can be filled with any of a variety of liquid optical materials, such as those described herein, and configured to accommodate via shape change. Implementations of IOLs are described herein, however, it should be appreciated that the fluorosilicone copolymers can be incorporated into other lens types including non-accommodating intraocular lenses, and magnification lenses (e.g., eyeglass lenses, contact lenses, camera lenses, imagining lenses, microscope lenses, telescope lenses, monocular lenses, binocular lenses, projector lenses, spotting scope lenses, telescopic gun sight lenses, theodolite lenses, medical equipment lenses, and the like).

Turning now to FIGS. 4A-4F, 5A-5F, and 6A-6C, the lens 100 generally include a solid optical component and a liquid optical material. The solid optical component can include a lens body 105 formed by any of a variety of components including an anterior optic 145 and a static element 150. The lens body 105 defines a sealed, fixed volume fluid chamber 155 filled by a fixed volume of the liquid optical material 156, sometimes referred to herein as an optical fluid and includes the fluorosilicone copolymers described in detail herein. The anterior optic 145 of the lens body 105 can include a central, dynamic membrane or wall 143 surrounded by a perimeter region 144. The dynamic membrane 143 of the anterior optic 145 is configured to undergo a shape change whereas the perimeter region 144 can be configured to resist or not to undergo a shape change. The static element 150, which can be a static lens, may not undergo a shape change as well. The static element 150 can be a lens configured to modify the overall optics provided by the lens, for example, where the bulging of the anterior optic 145 is relatively uncontrolled.

The terms "anterior" and "posterior" as used herein are used to denote a relative frame of reference, position, direction or orientation for understanding and clarity. Use of the terms is not intended to be limiting to the structure and/or implantation of the lens. For example, the orientation of the lens body 105 within the eye can vary such that the anterior optic 145 can be positioned anteriorly along the optical axis A of the lens 100 and the static element 150 positioned posteriorly along the optical axis A of the lens 100 relative to the eye anatomy. However, the anterior optic 145 can be positioned posteriorly and the static element 150 positioned anteriorly relative to the eye anatomy.

Figure 4A:
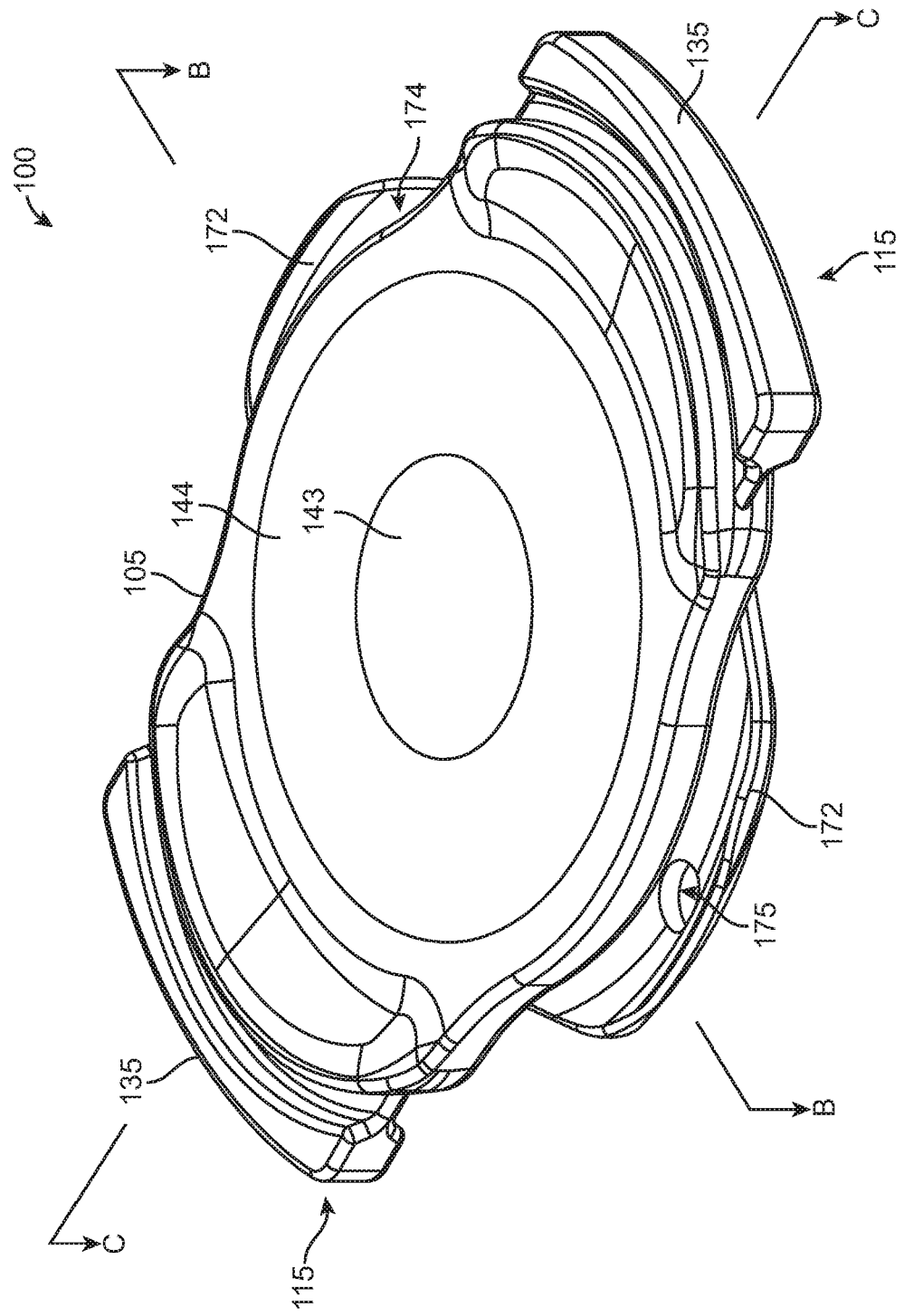
Figure 4B:
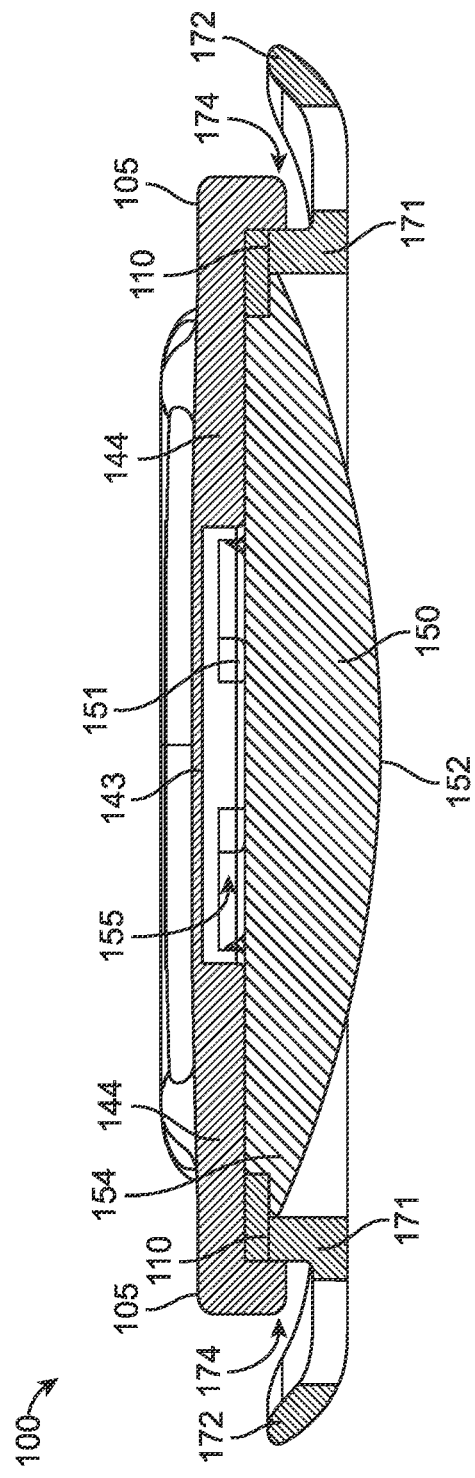
Figure 4C:
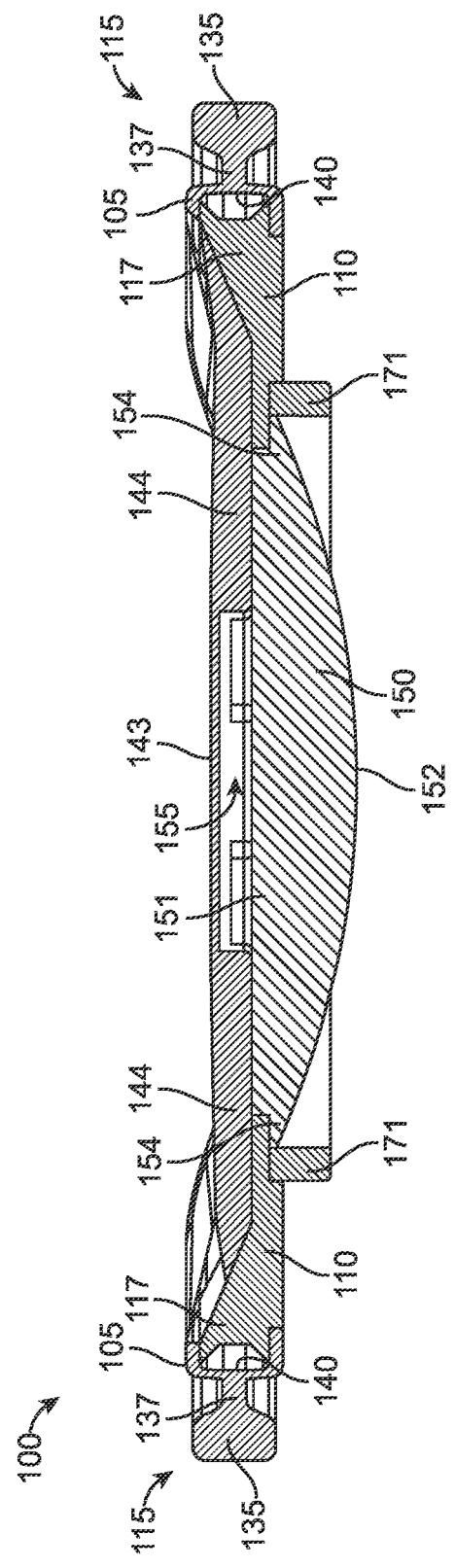
Figure 5A:
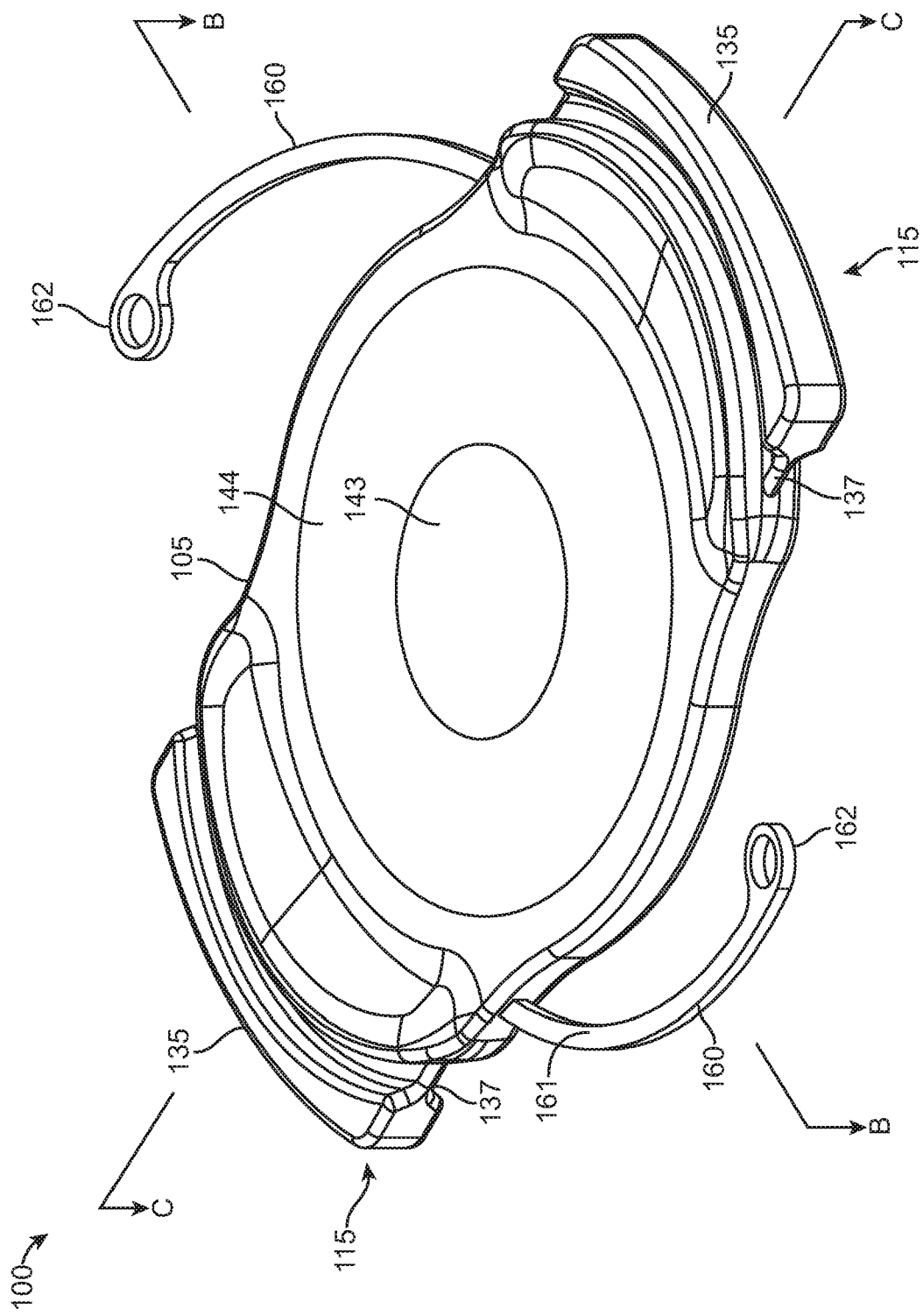
FIGS. 5A-F are perspectives of an intraocular lens.
Figure 5B:
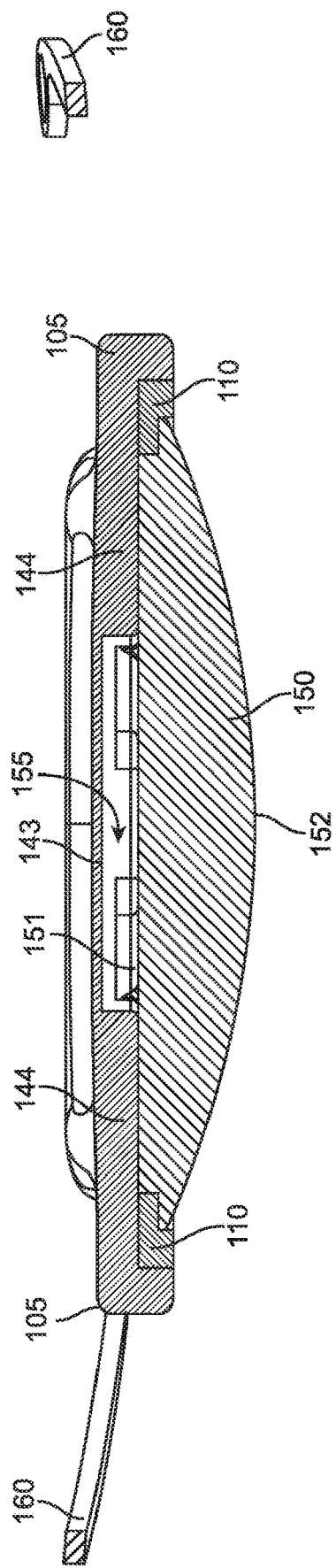
Figure 5C:
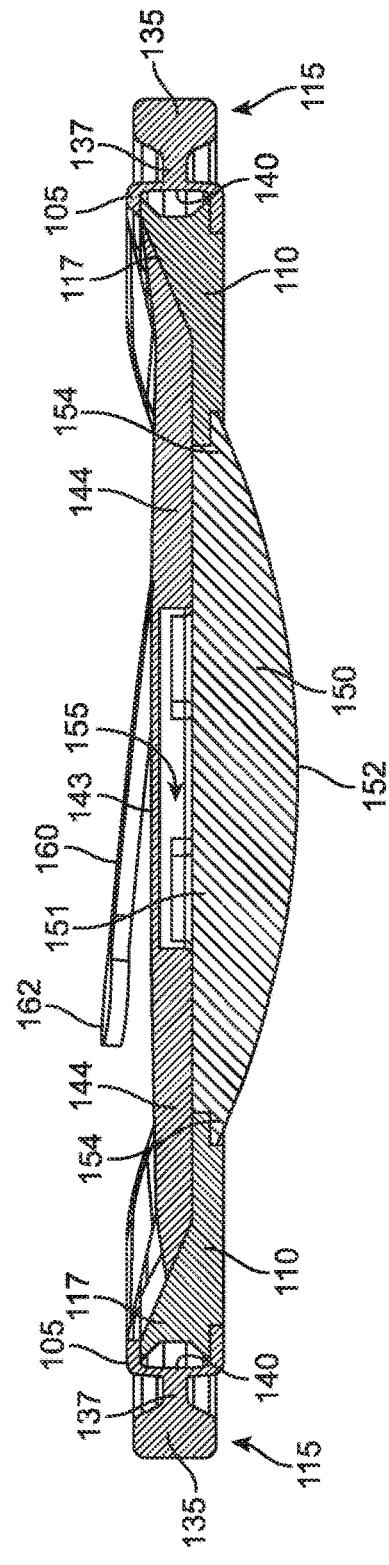

The equator region 108 of the lens body 105 can include at least one shape deformation membrane 140 (best shown in FIGS. 4C and 5C). The inner surfaces of the anterior optic 145, the dynamic membrane 143, the perimeter region 144 of the anterior optic 145, the shape deformation membrane 140 and the static element 150 can collectively form the fixed volume, fluid chamber 155. The components defining the fluid chamber 155 can be the solid optical component whereas the fixed volume of material filling the fluid chamber 155 can be the liquid optical material 156. The shape deformation membrane 140 can be positioned adjacent at least one force translation arm 115. As will be described in more detail below, movements of the force translation arm 115 causes movements of the shape deformation membrane 140 thereby deforming the liquid optical material 156 and the fluid chamber 155 to cause a change in the shape of the dynamic membrane 143 of the lens body 105. The anterior optic 145 can be molded as a unitary piece of polymer material including the dynamic membrane 143, perimeter region 144, shape deformation membrane 140, and force translation arms 115. Thus, the shape deformation membrane 140 and its associated force translation arm 115 can be molded together as a unitary part of the anterior optic 145. Any of a variety of the lens components may be molded together as a unitary piece or may be bonded together such as with glue or other bonding material. The lens can have minimal glued or bonded surfaces. In aspects, one or more of the lens components are coupled together by chemical connections rather than non-chemical bonding with glue.

Again with respect to FIGS. 4A and 5A, the anterior optic 145 can be a flexible optic formed of an optically clear, low modulus polymeric material such as silicone, polyurethane, or flexible acrylic. As mentioned above, the anterior optic 145 can include a perimeter region 144 surrounding a central, dynamic membrane 143 configured to outwardly bow. The dynamic membrane 143 can be positioned relative to the lens body 105 such that the optical axis A of the lens extends through the dynamic membrane 143. The anterior optic 145 can have a constant thickness such that it is a planar element. Alternatively, the anterior optic 145 can have a variable thickness. For example, the dynamic membrane 143 can have a reduced thickness compared to the perimeter region 144. The thinner cross-sectional thickness of the dynamic membrane 143 compared to the cross-sectional thickness of the perimeter region 144 can render it relatively more prone to give way upon application of a force on its inner surface. For example, upon an increased force applied against inner surfaces of the anterior optic 145 during deformation of the fluid chamber 155, the dynamic membrane 143 can bow outward along and coaxial to the optical axis A of the lens 100 while the perimeter region 144 maintains its shape. The dynamic membrane 143 can be configured to give way due to pressure applied by the liquid optical material 156 within the fluid chamber 155 onto the internal surface of the anterior optic 145 causing an outward bowing of the outer face (e.g., anterior face). Outer perimeter region 144 of the anterior optic 145 can have a thickness greater than the inner dynamic membrane 143 of the optic 145 and can be more resistant to reshaping under such internal pressure applied by the liquid optical material 156 in the fluid chamber 155. The outer perimeter region 144 of the anterior optic 145 can provide distance vision correction even when the inner dynamic membrane 143 is reshaped for near vision. The dynamic membrane 143 can have a substantially constant thickness. Alternatively, the dynamic membrane 143 can have a variable thickness. For example, the dynamic membrane 143 can have a linear gradient thickness, curved gradient thickness, 2, 3 or more thicknesses with a step including radiused or right angles. The dynamic membrane 143 can also include multiple materials, for example, materials configured to flex near a center of the dynamic membrane 143 and other materials configured to reinforce the optic zone and limit distortion. Thus, the dynamic membrane 143 of the anterior optic 145 can be formed of a material that is relatively more susceptible to outward bowing than the material of outer perimeter region 144. The various regions of the optic 145 can be injection or compression molded to provide a relatively seamless and uninterrupted outer face. The material of the regions can be generally consistent, though the dynamic membrane 143 can have different stiffness or elasticity that causes it to bow outward farther than the perimeter region 144.

The anterior optic 145 can be configured to have varied multifocal capabilities to provide the wearer of the lenses described herein with enhanced vision over a wider range of distances, for example, as described in U.S. Publication No. 2009/0234449, which is incorporated by reference herein in its entirety. The "optic zone" as used herein generally refers to a region of the lens body 105 that surrounds the optical axis A of the lens and is optically clear for vision. The "accommodating zone" as used herein generally refers to a region of the lens body 105 capable of undergoing shape change for focusing (e.g. the dynamic membrane 143). The optic zone is configured to have a corrective power although the entire optic zone may not have the same corrective power. For example, the dynamic membrane 143 and the perimeter region 144 of the anterior optic may each be positioned within the optic zone. The dynamic membrane 143 may have corrective power whereas the perimeter region 144 may not have corrective power. Or, for example, the diameter defined by the dynamic membrane 143 may have an optical power and the perimeter region 144 may have a power that is greater or lesser than that of the dynamic membrane 143. The dynamic membrane 143 can be equal to or smaller than the overall optical zone can create a multifocal lens. The accommodating zone of the lens body 105 can be equal to or smaller than the overall optic zone.

The shape deformation membrane 140 can extend along an arc length of the equator region 108 of the lens body 105. The arc length can be sufficient, either individually or in combination with other shape deformation membranes 140, to cause a reactive shape change in the dynamic membrane 143 upon inward (or outward) movement of the deformation membrane 140. Movement of the shape deformation membrane 140 in a generally inward direction towards the optical axis A of the lens 100 during accommodation can cause outward flexure or bowing of the dynamic membrane 143 without affecting the overall optic zone diameter in any axis.

The shape deformation membrane 140 can have a flexibility such that it is moveable and can undergo displacement relative to the lens body 105, the static element 150, and the anterior optic 145. For example, the shape deformation membrane 140 can be more flexible than adjacent regions of the lens body 105 such that it is selectively moveable relative to the lens body 105 and the perimeter region 144 of the anterior optic 145. The shape deformation membrane 140 can have a resting position. The resting position of the shape deformation membrane 140 can vary. In aspects, the resting position is when the shape deformation membrane 140 is positioned generally perpendicular to a plane parallel to the anterior optic 145 such that it has a cross-sectional profile that is vertically oriented, parallel to the optical axis A. The resting position of the shape deformation membrane 140 can also be angled relative to the optical axis A of the lens body 105. The shape and relative arrangement of the one or more side deformation membranes 140 provides the lens with a low force, low movement, high accommodative function.

The movement of the shape deformation membrane 140 can be a compression, collapse, indentation, stretch, deformation, deflection, displacement, hinging or other type of movement such that it moves in a first direction (such as generally toward an optical axis A of the lens body 105) upon application of a force on the shape deformation membrane 140.

The shape deformation membrane 140 lies adjacent or is coupled to or molded integral with a respective force translation arm 115. The one or more force translation arms 115 are configured to harness movements of one or more of the ciliary structures such that they are bi-directionally movable relative to the lens body 105 to effect accommodative shape change of the lens body 105. For example, and without limiting this disclosure to any particular theory or mode of operation, the ciliary muscle 18 is a substantially annular structure or sphincter. In natural circumstances, when the eye is viewing an object at a far distance, the ciliary muscle 18 within the ciliary body relaxes and the inside diameter of the ciliary muscle 18 gets larger. The ciliary processes pull on the zonules 20, which in turn pull on the lens capsule 22 around its equator. This causes a natural lens to flatten or to become less convex, which is called disaccommodation. During accommodation, the ciliary muscle 18 contracts and the inside diameter of the ring formed by the (ciliary ring diameter, CRD) ciliary muscle 18 gets smaller. The ciliary processes release the tension on the zonules 20 such that a natural lens will spring back into its natural, more convex shape and the eye can focus at near distances. This inward/anterior movement of the ciliary muscle 18 (or one or more ciliary structures) can be harnessed by the force translation arms 115 to cause a shape change in the lens body 105.

In aspects, as the force translation arm 115 is moved inwardly toward the optical axis A of the lens 100 due to ciliary muscle contraction, the force translation arm 115 abuts an outer surface of the shape deformation membrane 140 and applies a force against the outer surface. Thus, the contact between the shape deformation membrane 140 and the force translation arm 115 can be reversible contact such that upon ciliary muscle contraction the force translation arm 115 is urged against the outer surface abutting the membrane 140 and urging it inwardly. Upon ciliary muscle relaxation, the shape deformation membrane 140 returns to its resting position and the force translation arm 115 returns to its resting position. The elastomeric nature of the movable components (i.e. the dynamic membrane and/or the shape deformation membranes) can cause a return of the force translation arms 115 to their resting position. In aspects and as best shown in FIGS. 4C and 5C, the shape deformation membrane 140 is coupled to or integral with its respective force translation arm 115. As with other aspects, upon ciliary muscle contraction the force translation arm 115 and shape deformation membrane 140 move in concert from a resting position to a generally inwardly-displaced position causing shape change of the dynamic membrane 143. Displacement of the force translation arm 115 and associated shape deformation membrane 140 applies a compressive force on the fluid chamber and in turn deforms the chamber causing the dynamic membrane 143 to bulge outward.

The inward motion of the force translation arm 115 and associated shape deformation membrane 140 can be coaxial to an axis that is substantially orthogonal or perpendicular to the optical axis A. Meaning, the angle between the axis of motion and the optical axis can be 90 degrees plus or minus about 1 degree, 2 degrees, 3 degrees, 4 degreed, up to about 5 degrees. It should be appreciated that a compressive force applied to the force translation arms 115 such as by a ciliary structure may result in radially inward motion that is not perfectly orthogonal to the optical axis A and that some degree greater than or less than 90 degrees is considered herein. The angle between the axis of motion of the deformation membrane 140 and the optical axis A can also be substantially non-orthogonal or non-perpendicular. For example, the deformation membrane 140 can be compressed along an axis that is non-orthogonal to the optical axis A.

The number and arc length of each deformation membrane 140 can vary and can depend on the overall diameter and thickness of the device, the internal volume, refractive index of the material, etc. Generally, the lens body has sufficient rigidity and bulk to the lens such that it can be handled and manipulated during implantation while the deformation membrane(s) 140 are sufficiently flexible to allow the force translation arms to change the shape of the fluid chamber 155. Depending on the overall diameter and thickness of the lens 100, the arc length of the shape deformation membrane 140 can be at least about 2 mm to about 8 mm. In aspects, the lens has a single shape deformation membrane 140 with an arc length of between about 2 mm to about 8 mm. The single shape deformation membrane 140 can be designed to move between about 10 µm and about 100 µm upon application of forces as low as about 0.1 grams of force (gf) to achieve at least a 1D, or 1.5D, or 2D, or 2.5D, or 3D change in the dynamic membrane 143. In aspects, the IOL can have two, opposing shape deformation membranes 140 each having an arc length that is between about 3 mm and about 5 mm. The shape deformation membranes 140 can be designed to move between about 25 µm and about 100 µm each upon application of about 0.25 g force to 1.0 g force achieve at least a 1D change in the dynamic membrane 143.

The shape deformation membranes 140 can move or collapse relative to the rest of the lens body upon application of a degree of compressive force. Generally, the IOL is designed such that very low forces (including the application of compressive force towards the optical axis A as well as the release of the compressive force) are sufficient to cause micron movements to cause sufficient diopter changes and with reliable optics. The compressive force applied to achieve outward movement of the dynamic membrane 143 of the lens body 105 to effect accommodation can be as low as about 0.1 grams of force (gf). In aspects, the compressive force applied can be between about 0.1 gf to about 5.0 gf or between about 0.25 gf to about 1.0 gf or between about 1.0 gf to about 1.5 gf. The movements of the deformable regions of the lens body 105 (e.g. shape deformation membrane 140) relative to the central portion of the lens body 105 (e.g. dynamic membrane 143) in response to the compressive forces applied to achieve accommodation can be as small as about 50 µm. The movements of the shape deformation membrane 140 of the lens body relative to the dynamic membrane 143 in response to the compressive forces applied can be between about 50 µm to about 500 µm, between about 50 µm to about 100 µm, between about 50 µm to about 150 µm, or between about 100 µm to about 150 µm. The ranges of compressive forces applied (e.g. about 0.1 gf to about 1 gf) that result in these ranges of movement in the shape deformation membrane 140 (e.g. 50 µm-100 µm) can provide the devices described herein with an accommodating capability that is within a dynamic range of greater than at least ±1D and preferably about ±3 diopters (D). In aspects, the power is between ±4D and ±6D for about 100-150 µm movement. The devices described herein can have an accommodating range that is at least ±1D for about 100 µm movement of the shape deformation membrane 140 and about a compressive force of at least 0.25 gf applied to the shape deformation membrane 140 in a substantially inward direction towards the optical axis A. In aspects, the devices can have an accommodating range that is at least ±1D for about 50 µm movement and at least about 1.0 gf. In aspects, the devices can have an accommodating range that is at least ±3D for about 100 µm movement and at least about 1.0 gf. In aspects, the devices can have an accommodating range that is at least ±3D for about 50 µm movement and at least about 0.1 gf.

The micron movements described herein can be asymmetrical micron movements (e.g. from one side of the device) or can be symmetrical micron movements from opposing sides of the device or evenly distributed around the device relative to the optical axis. Whether the micron movements are asymmetric or symmetrical, the outward bowing of the dynamic membrane 143 achieved is substantially spherical. The micron movements described herein also can be a total collective movement of the shape deformation membranes 140. As such, if the lens 100 includes a single shape deformation membrane 140, that single membrane is capable of desired micron movement (e.g. 50 µm-100 µm) to achieve desired dioptric change (e.g. at least 1D to about 3D change). If the lens 100 includes two shape deformation membranes 140, the membranes together are capable of the achieving between 50 µm-100 µm movement to achieve the at least 1D dioptric change. The dioptric change achieved by the devices described herein can be at least about 1D up to approximately 5D or 6D change. In aspects, the dioptric change can be between 7D and 10D, for example, for patients having macular degeneration.

As mentioned above and still with respect to FIGS. 4A-4F and 5A-5F, the lens body 105 can include a static element 150. The static element 150 and the anterior optic 145 can be located opposite one another along the optical axis A of the lens 100. The static element 150 can be positioned outside the lens body 105 such that the flat surface 151 forms the inner surface facing the fluid chamber 155 of the lens body 105 and the curved surface 152 is in contact with the fluid of the eye. Alternatively, the static element 150 can be positioned inside the lens body 105 such that the flat surface 151 is in contact with the fluid of the eye and the curved surface 152 forms the inner surface facing the fluid chamber 155 of the lens body 105.

The static element 150 can be optically clear and provide support function without affecting the optics of the lens 100. As such, the static element 150 can have zero power and can form a posterior support to the lens body 105. The static element 150 can be formed of silicone, urethane, acrylic material, a low modulus elastomer, or combinations thereof. The static element 150 can be or include a static optic to correct to emmetropic state, or can be of an appropriate power for an aphakic patient (usually ±10D to ±30D). Thus, the static element 150 can have no optical power up to about ±30D. If the lens 100 is being used in conjunction with a separate capsular lens (e.g. as a "piggyback" lens), the power can be in the range of about −5D to about +5D to correct for residual refractive or other optical aberrations in the optical system of the eye. The static element 150 can be plano-convex, convex-plano, convex-convex, concave-convex or any other combination. The static element 150 (or the lens positioned posteriorly) can be a toric lens, spherical lens, aspheric lens, diffractive lens or any combination of both, for example, in order to reduce or compensate for any aberrations associated to the flexible lens. The relative refractive indices of the static element 150 and the fluid surrounding it (whether that is the fluid of the eye or liquid optical material 156 within the fluid chamber 155) will determine the power of the static element 150 for any given shape.

The lens 100 can include any of a variety of combinations of reinforcements and/or supports to provide mechanical stability to the assembled lens 100. For example, the reinforcements may be in the peripheral regions of the anterior lens 145 and/or the static element 150. The reinforcements can be either optically clear or opaque. The reinforcing structures may be formed of a rigid polymer, including but not limited to silicone, polyurethane, PMMA, PVDF, PDMS, polyamide, polyimide, polypropylene, polycarbonate, etc, or combinations thereof. Other regions of the lens 100 can include one or more reinforcements or supports as well. In aspects, the one or more supports can be positioned external to the fluid chamber 155 such that the supports surround at least an outside portion of the lens body 105. For example, the external support can be a generally annular element extending around a perimeter of the lens body 105 and have a central opening through which at least the dynamic membrane 143 of the anterior optic 145 is aligned such that the dynamic membrane 143 is available for outward deformation.

In aspects, the lens 100 includes one or more internal supports 110 located within the lens 100, such as within or facing the fluid chamber 155 of the lens body 105 and/or embedded in one or more regions of the solid optical components. The one or more internal supports 110 can be thickened portions on an interior side of the outer, perimeter region 144 of the anterior optic 145. The one or more internal supports 110 can also be separate components coupled to or within the lens. The one or more internal supports 110 can be coupled to and/or embedded inside the perimeter region 144 of the anterior optic 145. The internal supports 110 can be immovable feature (meaning a feature not involved in accommodation) configured to mechanically isolate the optical components of the lens body 105 preventing or mitigating optical distortion during movement of the moving parts of the lens 100, such as the force translation arms 115, the shape deformation membrane 140, and/or the dynamic membrane 143. The internal supports 110 can be formed of a material (or materials) that is harder, thicker and/or more rigid than the shape deformation membrane 140 or the dynamic membrane 143 of the anterior optic 145 to prevent inadvertent movements of the moving parts of the device. Alternatively, the internal supports 110 may be made of the same material as the shape deformation membrane 140 or the dynamic membrane 143 of the anterior optic 145 and accomplish the mechanically isolating function due to the geometry of the support structure. The support 110 can be formed of a rigid polymer, including but not limited to silicone, polyurethane, PMMA, PVDF, PDMS, polyamide, polyimide, polypropylene, polycarbonate, etc., or combinations thereof. For example, the internal support 110 can be a combination of multiple silicones or silicone with a rigid or semi-rigid skeletal insert.

The lens body may include a plurality of internal supports 110. The internal supports 110 can be relatively planar elements that lie generally parallel to the central, longitudinal plane of the lens 100. An outer region of each support 110 can be positioned adjacent to the equator region 108 of the lens body 105 and extend inward towards the dynamic membrane 143 of the anterior optic 145. The outer region of the support 110 can be coupled to or integral with the equator region 108 of the lens body 105 or the outer region of the support 110 can be spaced away from the equator region 108. The support 110 can be spaced away from the equator region 108 near where the deformation membrane 140 extends along an arc length of the equator region 108. This spacing away from the deformation membrane 140 provides tolerance such that the deformation membrane 140 does not prematurely abut or contact the support 110 during inward accommodative movements.

The distribution and spacing of the one or more internal supports 110 relative to the shape deformation membrane 140 can minimize their contact with the moving parts of the lens whether near the perimeter region of the lens body 105 or the central region of the lens body 105. The shape of the internal supports 110 can also minimize or limit contact between the internal supports 110 and the shape deformation membrane 140. For example, the outer region of the supports 110 can be beveled near where the supports couple to the equator region 108 such that the bevel allow for inward movement of the shape deformation membrane 140 while avoiding contact between the membrane 140 and the outer perimeter of the supports. The bevel can be a single bevel having an angle that is between about 10-80 degrees. It should be appreciated that the outer region of the one or more supports need not include a bevel. Contact between the shape deformation membrane 140 and the one or more internal supports 110 can be avoided in other ways aside from incorporating a bevel. For example, the one or more supports 110 can be spaced a distance away from the shape deformation membrane 140 (e.g. along the perimeter and/or away from the perimeter) to avoid contact. The internal supports 110 can also have a length between the outer regions to their inner regions such that they extend a distance towards the center of the lens body providing stability and support, but generally stop short of the central, dynamic membrane 143 of the anterior optic 145. As such, the internal supports 110 distributed around the lens body 105 can aid in creating a central step-down in thickness from the outer perimeter region 144 of the anterior optic 145 to the dynamic membrane 143 of the anterior optic 145.

The lens body 105 can include a sealed, fixed volume fluid chamber 155 filled collectively formed by the inner-facing surfaces of the shape deformation membrane 140, the anterior optic 145, and the static element 150 and filled by a fixed volume of an liquid optical material 156. The inner-facing surfaces of the one or more inner supports 110 of the perimeter region 144 and the inner-facing surface of the dynamic membrane 143 of the anterior optic 145 also form part of the fluid chamber 155. Thus, the distribution, size, shape and number of the one or more supports 110 impacts the overall shape of the fluid chamber 155.

The liquid optical material 156 filling the fluid chamber 155 can be a non-compressible liquid optical material and the volume of the fluid chamber 155 can be substantially identical to the volume of liquid optical material 156. As such, the liquid optical material 156 filling the chamber 155 does not cause significant outward bowing of either the dynamic membrane 143 or the deformation membrane 140 in the resting state when no substantial outside forces are applied to the lens 100. In aspects, the fluid chamber 155 can be slightly overfilled with liquid optical material 156 such that the dynamic membrane 143 has some outward bowing at rest. A small degree of resting outward bowing in the dynamic membrane 143 can reduce optical artifacts in the lens. However, no matter how much resting outward bowing is present in the dynamic membrane 143, the membrane 143 can still undergo additional outward bowing upon application of compressive forces on the shape deformation membrane 140 to provide accommodation. The pressure inside the fluid chamber 155 can be substantially equal to the pressure outside the fluid chamber 155. Because the liquid optical material 156 in the fluid chamber 155 is non-compressible its shape deforms along with the shape of the chamber 155. Deformation of the chamber 155 in one location (e.g. micrometer inward movements of the shape deformation membrane 140) causes the non-compressible liquid optical material 156 contained within the fixed-volume fluid chamber 155 to press against the inner-facing surfaces forming the fluid chamber 155. A reactive deformation of the fluid chamber 155 occurs in a second location to create sufficient accommodating change. The dynamic membrane 143 of the anterior optic 145 is configured to bow outward upon application of a force (e.g. due to relative thickness and/or elasticity) compared to other parts of the anterior optic 145 such as the perimeter region 144. Thus, inward movement of shape deformation membrane 140 urges the liquid optical material 156 to deform along with the chamber 155 and press against the inner-facing surface of the anterior optic 145. This results in outward bowing and reshaping of the outer surface of the dynamic membrane 143 to cause the accommodative portion of the optic zone to become more convex increasing the power of the lens 100. The internal supports 110 provide sufficient stability to the lens body 105 so that application of the compressive forces on the shape deformation membrane 140 causes the micrometer movements with minimal distortion of the optics.

The liquid optical material 156 contained within the fluid chamber 155 of the lens body 105 remains substantially within the optic zone during rest in both the unaccommodated, resting state and during accommodation. The liquid optical material 156 remains within the lens body 105 and can contribute to the accommodative shape change of the dynamic membrane 143 by deforming in shape along with the deformation of the shape of the fluid chamber 155. It should be appreciated that this shape change of the dynamic membrane 143 can occur without actual flow of the liquid optical material 156 within the fluid chamber 155, for example, from one part of the chamber to another. Rather, a force being applied on the shape deformation membrane 140 deforms the fluid chamber 155 in a first region that can cause a reactive deformation of the fluid chamber 155 in at least a second region. The fluid chamber 155 has a fixed volume and is deformable. The liquid optical material 156 filling the fluid chamber 155 changes shape along with and depending on the shape of the fluid chamber 155. Inward deformation of one or more portions of the chamber 155, for example, movement of the shape deformation membrane 140 near the perimeter region of the lens body 105, can cause a reactive outward deformation of another portion of the chamber 155, for example, outward bulging of the dynamic membrane 143 of the anterior optic 145, due to the non-compressible liquid optical material 156 inside the fluid chamber 155 pressing against its inner surface. The liquid optical material 156 need not flow between separate chambers of the IOL, but rather the liquid optical material 156 can change shape along with the changing shape of the fluid chamber 155 to cause the accommodative portion of the optic zone of the anterior optic 145 to bow outward and increase the power of the IOL 100. As described elsewhere herein, very small movements of the force translation arms 115 (or single force translation arm 115 in the case of an asymmetric mechanism) result in immediate, small movements in the shape deformation membrane 140 to change the shape of the dynamic membrane 143 and sufficient dioptric change. Whether these very small movements are symmetrical due to at least a pair of opposing force translation arms 115 or asymmetrical due to a single force translation arm 115, the outward bowing of the dynamic membrane 143 that is achieved is spherical and symmetrical. The shape deformation membrane 140 is sensitive to small forces imparted on the lens body 105. This is useful in providing accommodative changes upon ciliary muscle movements. However, this can cause power changes with undesirable optical consequences if the liquid optical material 156 migrates away from the fluid chamber 155, for example, into the surrounding solid optical components 153. As discussed elsewhere herein, it is preferred that the liquid optical material 156 be chemically dissimilar enough to prevent miscibility with the solid optical components 153 it comes into contact with. For example, if the liquid optical material 156 is a silicone oil and the sealed chamber 155 is defined by solid optical components 153 formed of a chemically similar silicone elastomer like polydimethylsiloxane (PDMS), the silicone oil and silicone elastomer are miscible. The oil tends to enter into the silicone elastomer causing an unintended optical power change in the lens. The surface curvatures of the lens body would decrease (less convex or more concave) thereby reducing the power of the lens and providing insufficient optical power to the patient. This also reduces the ability of the lens to undergo sufficient shape change when necessary at the time of accommodation. Even minor changes of the internal pressure can result in substantial undesirable changes to the optical power of the lens.

The liquid optical material 156 described with respect to the fluid chamber 155 can include any of a variety of the fluorosilicone copolymers described herein. The liquid optical materials described herein can be incorporated with any of a variety of lenses having a fluid chamber 155. The lens need not include the specific components and features described with respect to FIGS. 4A-4F or FIGS. 5A-5F or FIGS. 6A-6C. For example, the lens having the fluid chamber 155 filled with liquid optical material 156 can include rigid walls rather than walls capable of deforming upon application of a compressive force. The lens having the fluid chamber 155 can, but need not, incorporate the force translation arm(s) 115, dynamic membrane 143, the shape deformation membrane 140, haptics 160, posterior optic 152, etc.

Again with respect to FIGS. 4A-4F and 5A-5F, the lens 100 can include one or more force translation arms 115 configured to move back and forth relative to the lens body 105 to cause the dioptric changes described elsewhere herein. The lenses described herein are particularly suited to harness the movements of the ciliary body applied directly onto the force translation arms 115 positioned against the ciliary structures into shape change of the lens. The force translation arms 115 are configured to harness and translate forces applied by the ciliary structures into the shape changes of the movable parts of the lens body 105 described above. Each force translation arm 115 can include an outer, contact portion 135 and an inner region 137 operatively coupled to a perimeter or equator region of the lens body 105. Inner regions 137 of each force translation arm 115 can be positioned in contact with or adjacent the shape deformation membrane 140 such that the force translation arm 115 can move relative to the relaxed, shape deformation membrane 140. For example, the force translation arm 115 can be spaced away from the membrane 140 during rest, moved inward during accommodation to abut against the membrane 140 urging the membrane 140 inward, and then upon release of force during disaccommodation move away from the membrane 140 to release the membrane 140 from the inward, deforming force. As such, the inner region 137 of the force translation arm 115 can come into reversible contact with the shape deformation membrane 140 depending on whether an accommodating force is applied by the surrounding eye tissue. Alternatively, the inner region 137 of each force translation arm 115 can be physically coupled to or integral with the shape deformation membrane 140 such that the force translation arm 115 and the membrane 140 move in concert with one another.

In aspects, the inner region 137 of the force translation arm 115 can have a cross-sectional thickness taken along a plane between an anterior surface of the lens body 105 and the posterior surface of the lens body 105 that is narrower than a cross-sectional thickness of the equator region 108 of the lens body 105 taken along the same plane. This can allow for the inner region 137 of the force translation arm 115 to displace the deformation membrane 140 a distance inward without abutting against the regions of the equator 108 not intended to be deformed. The cross-sectional thickness of the inner region 137 of the force translation arm 115 can also allow for inward movement of the arm 115 without making contact with an internal support 110 positioned adjacent the deformable membrane 140. It should be appreciated however, that the cross-sectional thickness of the inner region 137 of the force translation arm 115 need not be narrower. The outer contact portion 135 of the force translation arms 115 can, but need not, have a larger cross-sectional thickness than the inner region 137. It should be appreciated, however, that the outer contact portion 135 of the force translation arms 115 can also have the same cross-sectional thickness as the inner region 137. The outer contact portion 135 can also have rounded or curved contours.

The contact portions 135 of the force translation arms 115 can incorporate features that improve their connection with one or more of the ciliary structures without causing damage. Generally, the contact portions 135 avoid piercing or causing trauma to the ciliary structures. In aspects, the contact portions 135 can interfere with the ciliary structures while providing an atraumatic surface to engage adjacent eye tissues such that movement can be transferred without causing trauma to the tissues themselves. The outer contact portion 135 can also be molded to have one or more concavities, indentations, grooves, teeth, combs, or other surface features to improve, for example, contact and/or interdigitation with eye tissues such as the ciliary process or zonular process.

The lens 100 can be implanted such that the contact portion 135 of the force translation arms 115 is either in resting contact or readily in contact upon contraction of the ciliary muscle 18 with at least one of the ciliary structures (i.e. zonules, ciliary processes, ciliary muscle, and/or ciliary body) to drive shape change of the optics during accommodation and disaccommodation. In a preferred implementation, the lens 100 is implanted such that the contact portion 135 of the force translation arms 115 lies in resting contact or ready contact with the ciliary body apex. In another preferred implementation, the lens 100 is implanted such that the contact portion 135 of the force translation arms 115 lies in resting or ready contact with the ciliary body. In aspects, the lens 100 is sized such that it is generally oversized relative to the ciliary structures. This can ensure contact between the force translation arms 115 and the ciliary structure during accommodation. In aspects, the lens is oversized by at least about 0.80 mm, 0.75 mm, 0.70 mm, 0.65 mm, 0.60 mm, 0.55 mm, or 0.05 mm to guarantee ciliary contact with the force translation arms 115. It should be appreciated that the lens need not be oversized and in some circumstances oversizing of the lens may be avoided. For example, accurate measurements of the ciliary diameter at the plane of the lens may be relied upon to ensure the fit of the lens is suitable and optimized for a particular patient.

The force translation arms 115 described herein can have a fixed length. The fixed length force translation arms 115 can have a size selected that is appropriate for each patient based on pre-operative measurements. Alternatively, the length of the force translation arms 115 can be adjustable. The adjustment of the force translation arms 115 length can be performed prior to, during, or any time after insertion in the eye. Along with the adjustment of the length of the force translation arms 115, the position of the force translation arms 115 relative to the one or more ciliary structures can vary. In aspects, the force translation arms 115 can extend generally parallel to the plane of the lens 100 or can be angled relative to the plane of the lens 100.

Contraction of the ciliary muscle and inward/anterior movement of one or more of the ciliary structures towards the optical axis A of the lens 100 applies a force against the contact portions 135 of the force translation arms 115. The force translation arms 115 are rigid enough relative to the deformation membrane 140 to transfer the forces applied by one or more moving parts of the eye (e.g. one or more ciliary structures) to cause inward movement of the deformation membrane 140. In aspects, the force translation arms 115 can be a rigid polymer such as silicone, polyurethane, PMMA, PVDF, PDMS, polyamide, polyimide, polypropylene, polycarbonate, etc., or combinations thereof. In aspects, the force translation arms 115 can be an element reinforced with a rigid material. For example, the force translation arms 115 can have an inner, rigid element such as silicone elastomer, polyurethane, PMMA, PVDF, PDMS, polyamide, polyimide, polypropylene, polycarbonate, etc. that is covered by a softer material such as silicone elastomer, polyurethane, or flexible acrylic materials that are hydrophobic or hydrophilic. In silicone, polyurethane, PMMA, PVDF, PDMS, polyamide, polyimide, polypropylene, polycarbonate, the force translation arms 115 can include an inner, rigid element that extends between the outer contact portion 135 to the inner contact portion 137. In silicone, polyurethane, PMMA, PVDF, PDMS, polyamide, polyimide, polypropylene, polycarbonate, the inner, rigid element extends only along a partial length of the force translation arms 115 between the outer portion 135 and the inner portion 137. For example, the inner, rigid element need not extend clear to the outer contact portion 135 where the force translation arms 115 make contact with the ciliary structures to provide a softer and atraumatic surface so as not to damage the ciliary structures. The inner, rigid element also need not extend clear to the inner contact portion 137 such that upon inward movement of the shape deformation membrane 140 by the force translation arm 115, the inner, rigid element of the force translation arm 115 remains outside the lens body 105. Generally, the force translation arms 115 are formed of a material and/or sized in a manner that they maintain their shape when forces are applied to them by a ciliary structure and they do not collapse or deform upon transferring that force to move the shape deformation membrane 140. As described above, movement of the shape deformation membrane 140 causes a shape change in the fluid chamber 155, which changes the shape of the liquid optical material filling the fluid chamber 155. When the liquid optical material presses against the inner surfaces of the lens body 105 it causes an outward bowing in the dynamic membrane 143 of the anterior optic 145. This outward bowing results in a more spherical or convex lens body 105 shape thereby increasing the power of the lens suitable for near vision focus.

The number of force translation arms 115 and shape deformation membrane 140 can vary. The lens 100 can include two force translation arms 115 positioned on opposing sides of the device lying adjacent to two shape deformation membrane 140, as shown in FIGS. 4C and 5C. Alternatively, the lens 100 can include a single force translation arm 115 movable in a manner sufficient to change the shape of the dynamic membrane 143 of the anterior optic 145 to achieve a desired dioptric change. The lens 100 can also include more than two arms, such as three, four, or more force translation arms 115 distributed around the lens body 105. The force translation arms 115 can be distributed in a symmetric manner around the perimeter of the lens 100 or in an asymmetric manner. It should be appreciated that the number of force translation arms 115 need not match the number of shape deformation membranes 140. For example, the lens 100 can include a single shape deformation membrane 140 extending along an arc length of the equator region 108 of the lens body 105 and more than one force translation arms 115 configured to make contact with or coupled to different regions of the single shape deformation membrane 140.

The lens 100 can also include a stabilization system 120. The stabilization system 120 can be configured to maintain alignment of the optics of the device and resist movement of the device once the device is implanted and undergoing shape changes. Unlike the force translation arms 115, the stabilization system 120 does not cause accommodation of the lens 100. And because the force translation arms 115 are independent from the stabilization system 120 and are not necessary to fix, center, stabilize, and/or hold the lens 100 in position within the eye, the lenses 100 described herein can incorporate a single, asymmetric force translation arm 115 sufficient to provide the dioptric change of the dynamic membrane.

The stabilization system 120 can be coupled to a perimeter region of the device 100, for example, bonded, coupled, or molded as part of the lens body 105 or to an exterior support, if present. In silicone, polyurethane, PMMA, PVDF, PDMS, polyamide, polyimide, polypropylene, polycarbonate, the stabilization system 120 can be coupled to a posterior region of the device 100 such that it can provide stabilization and engagement with a portion of the capsular bag, such as with the anterior capsule.

The stabilization system 120 can vary. In silicone, polyurethane, PMMA, PVDF, PDMS, polyamide, polyimide, polypropylene, polycarbonate, the stabilization system 120 includes one or more of a stabilization haptic, static haptic, ring-like element, a flange element or wing, or other stabilizing feature. In silicone, polyurethane, PMMA, PVDF, PDMS, polyamide, polyimide, polypropylene, polycarbonate, the stabilization system 120 can include a ring-like structure 171 having a wing 172 extending outward from a region of the ring-like structure 171, such as the posterior end (see, for example, FIGS. 4A-4F). An anterior end of the ring-like structure 171 can be coupled to a peripheral connecting ring of the static element 150 such that the wing 172 on its posterior end extends posterior to the lens body 105. For example, an outer diameter of the ring-like structure 171 can be sized to be received within an inner diameter of a peripheral connecting ring of the static element 150. It should be appreciated, however, that other coupling arrangements between the stabilization system 120 and the lens body 105 are considered herein. The ring-like structure 171 and wing 172 can be coupled to or integral with other portions of the lens body 105 need not be coupled to the static element 150. Generally, the coupling of the stabilization system 120 to the lens body 105 is such that the wing 172 is positioned in a posterior position relative to the lens body 105 and to the force translation arms 115 along the optical axis A of the lens 100. Additionally, the stabilization system 120 and its components such as the wing 172 are coupled to the lens body 105 in a manner that does not interfere with movement of the force translation arms 115 and the shape deformation membrane 140. For example, as shown in FIG. 4A, the stabilization ring 171 can include a pair of wings 172 that extend outward from the periphery of the lens body 105 between the location of the force translation arms 115. In silicone, polyurethane, PMMA, PVDF, PDMS, polyamide, polyimide, polypropylene, polycarbonate, the wings 172 can have an outer elevation, but because they are positioned 90 degrees relative to the force translation arms 115 that can provide stability without interfering with accommodative movements of the arms 115. Forces applied to the wing 172 or the ring-like structure 171 do not get transferred by the stabilization system 120 to the lens 100 in a manner that causes deformation of the fluid chamber 155 or shape change in the dynamic membrane 143. The wing 172 can be positioned in a posterior position relative to the lens body 105 and to the force translation arm 115. An anterior surface of the wing 172 may also be on the same plane as the force translation arm 115. The more anterior the wing 172, the greater the wing 172 can pull the lens body 105 in a posterior direction.

The ring-like structure 171 of the stabilization system 120 can be generally cylindrical in shape and the wing 172 can have a generally oval or elliptical outer dimension such that the wing 172 extends out beyond the outer diameter of the ring-like structure 171 in at least two regions along the perimeter of the lens body 105. The anterior end of the ring-like structure 171 can be coupled to a peripheral connecting ring of the static element 150 and the wing 172 can be dimensioned to remain outside the lens body 105 on a posterior end and extends out beyond the outer diameter of the lens body 105 at the at least two regions. The at least two regions where the wing 172 extends out beyond the outer diameter of the lens body 105 can be oriented relative to the lens body 105 such that the wing 172 provides stabilization support relative to the force translation arms 115. For example, if the lens 100 includes a pair of opposing force translation arms 115, the wing 172 can be arranged relative to the lens body 105 such that the wing 172 extends outward from the lens body 105 between the location of the opposing force translation arms 115 (see, for example, FIG. 4A). It should be appreciated that the wing 172 can have other shapes besides oval and elliptical. For example, the wing 172 can also be cylindrical and have an outer diameter configured to extend outward beyond the outer diameter of the ring-like structure 171 and the lens body 105 along 360 degrees. Alternatively, the wing 172 can have more than two locations where it extends beyond the outer diameter of the lens body 105 such as three, four, five, or more locations. The ring-like structure 171 and the wing 172 can provide 360 degree support and stabilization to the lens 100.

As mentioned above, the ring-like structure 171 can incorporate a pair of wings 172 that are positioned between or rotated 90 degrees relative to the location of the force translation arms 115. An outermost edge of the wings 172 can project anteriorly such that a channel or groove 174 is formed near an inner region of the wing 172, (see FIGS. 4A-4B). When the ring-like structure 171 is positioned within the capsular bag, this outer elevation of the wings 172 can engage with a posterior-facing internal surface of the capsular bag to help urge the lens 100 in a posterior direction relative to the bag. Additionally, the edge of the capsulorhexis can be received and held within the groove 174. In aspects, the edge can be captured between the groove 174 of the wing 172 and a posterior-facing edge of the lens body 105.

As described elsewhere herein, the force translation arms 115 are configured to extend outside the capsular bag 22 to engage with ciliary structures such that the physiological forces from ciliary muscle contraction can cause a change in optical power of the lens in a manner that is independent of the capsular mechanism or movement of the capsular bag 22. The wing 172 extending outward from a posterior end region of the lens body 105 can remain inside the capsular bag 22 while the force translation arms 115 extending generally from the equator region 108 or anterior end region of the lens body 105 extend outside the capsular bag 22 to engage with the ciliary structures. The wing 172 can be arranged to engage the posterior-facing surface of the edge of the capsular bag 22 formed by the anterior capsulorhexis to improve the fixation of the lens 100 within the eye. The edge of the capsular bag 22 formed by the capsulorhexis can be received within the groove 174 formed between the posterior surface of the lens element 105 and an anterior surface of the wing 172. The capsulorhexis can thus, aid in fixing the lens position.

The wing 172 can have interruptions providing for flexibility during handling as well as allow the surgeon to access portions of the lens 100 and capsular bag 22 posterior to the wing 172. This may be preferred in case the surgeon needs to clean the capsular bag, remove viscoelastic, adjust the position of the lens, or any other procedure in which the surgeon uses a tool to manipulate the environment posterior to the lens. In aspects, the interruptions can include one or more apertures 175 extending through a region of the wing 172 (see FIGS. 4A, 4D). The interruptions can also include one or more indentations or grooves or other feature at an outer perimeter of the wing 172. The indentations can allow for easy insertion into the eye as well as allow for withdrawal of viscoelastic from inside the capsular bag 22 using a cannula or other tool known in the art.

Figure 6A:
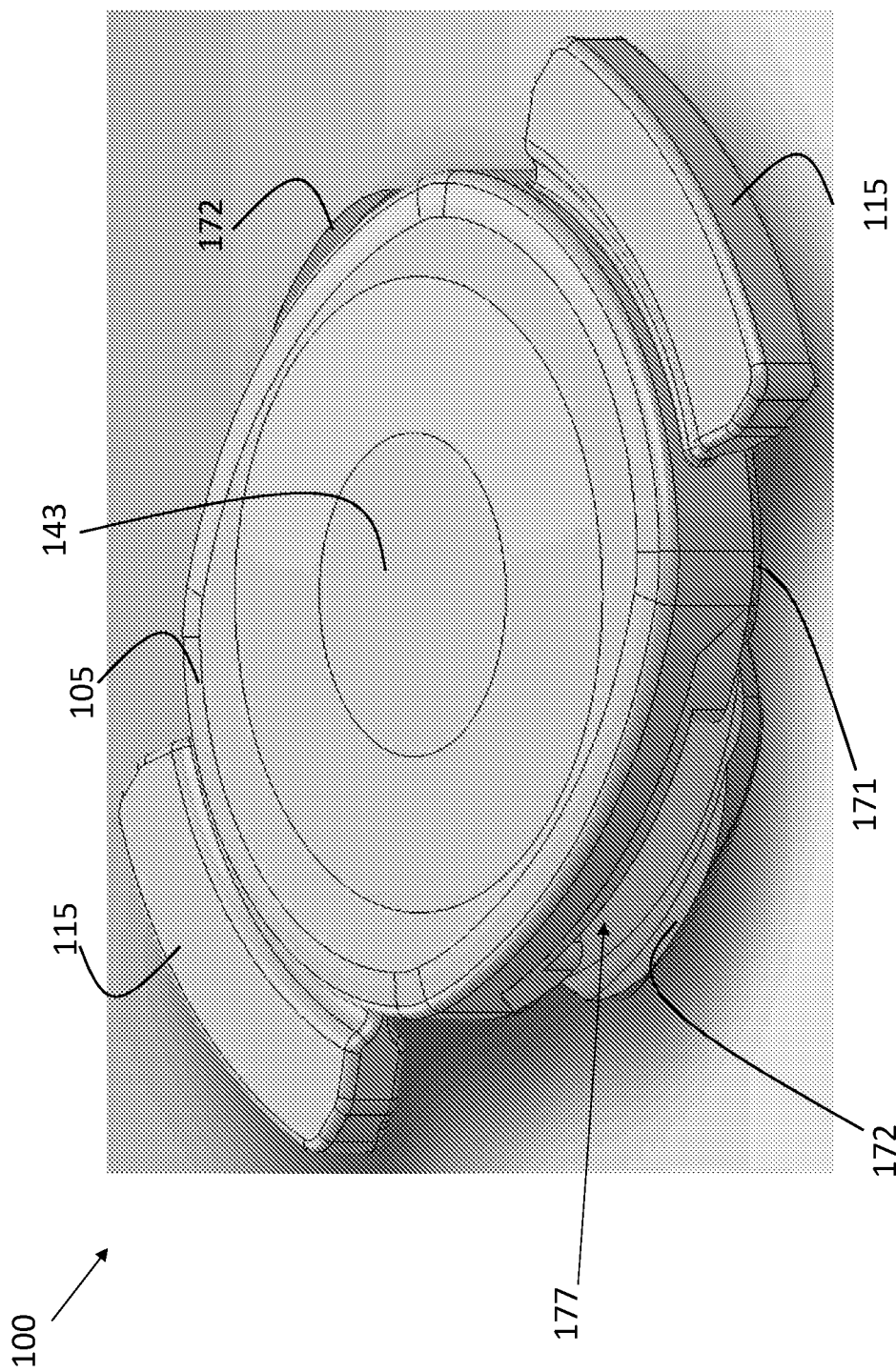
FIGS. 6A-6C are perspectives of a lens.
Figure 6B:
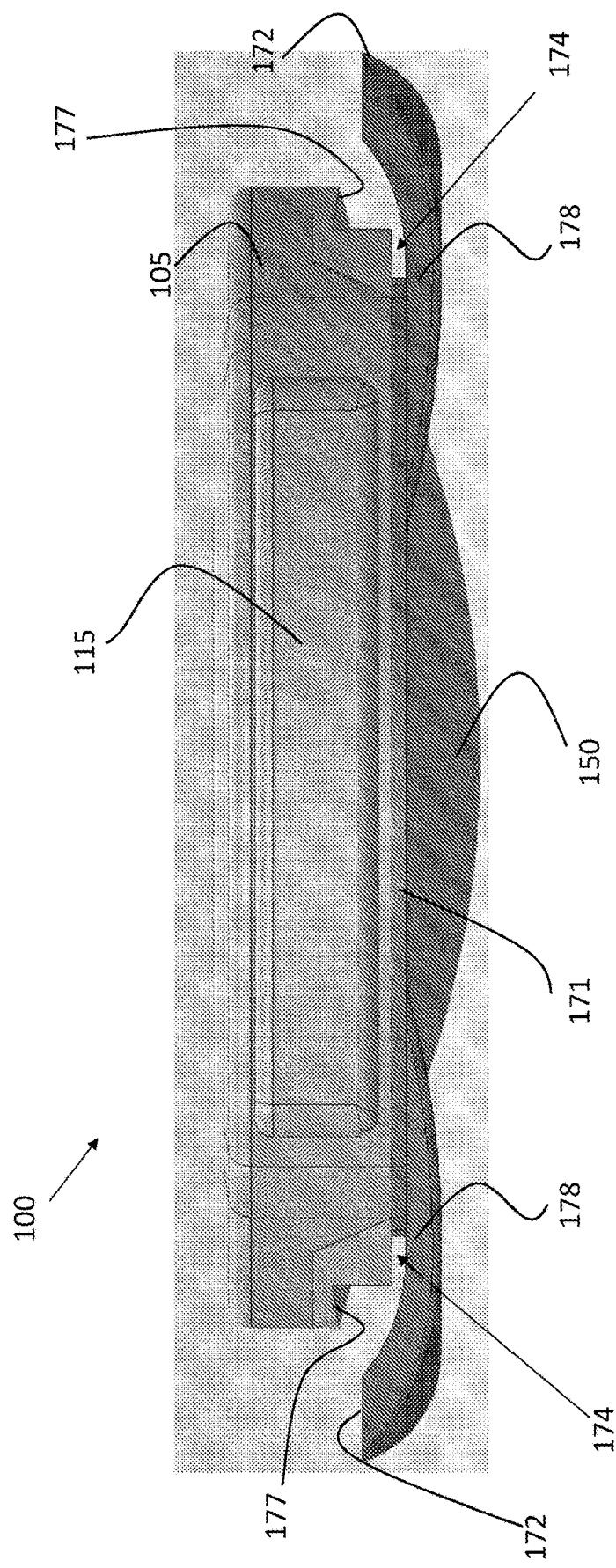
Figure 6C:
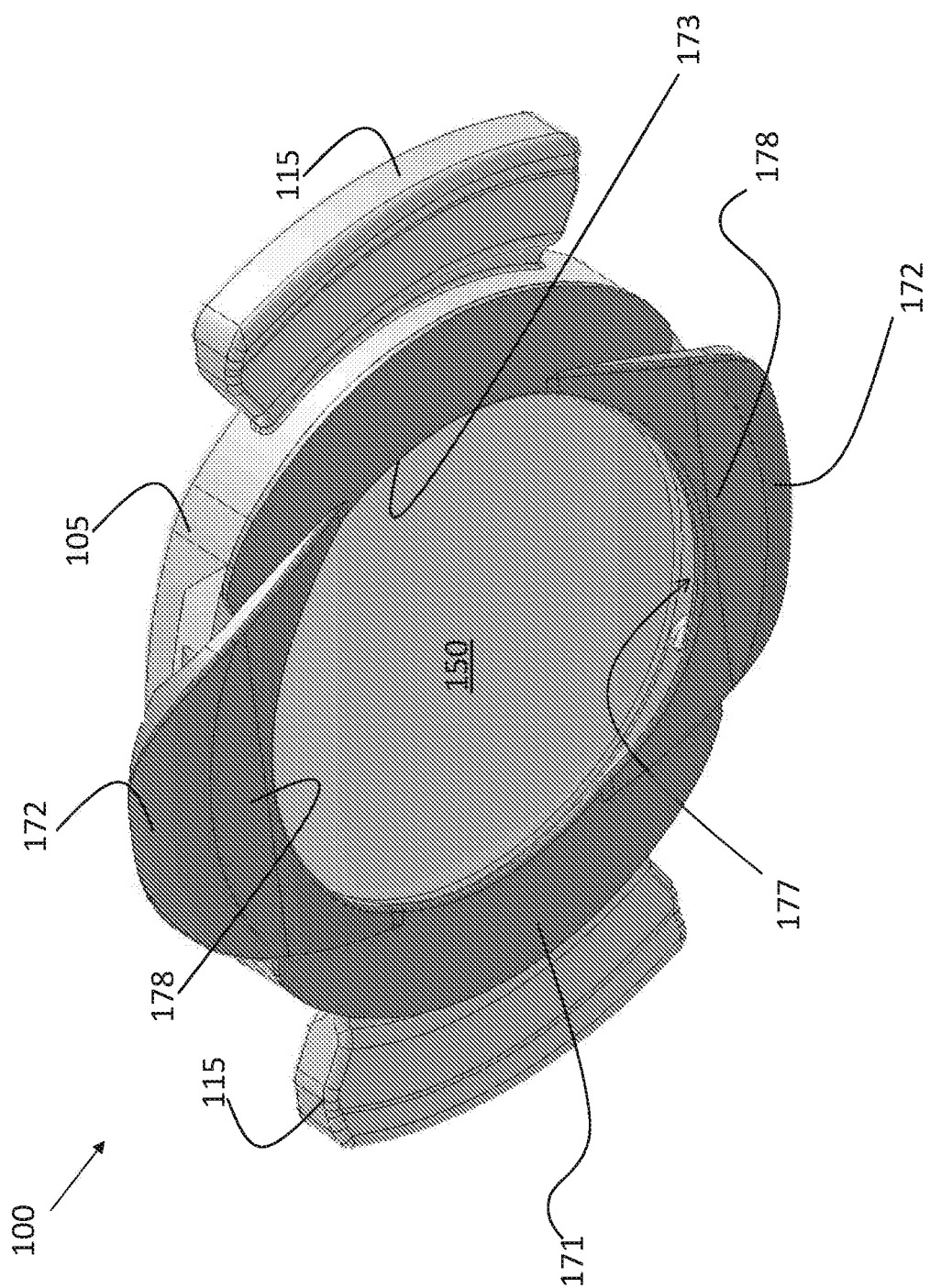

FIGS. 6A-6C illustrate an implementation of a lens 100 comprising a stabilization system configured to insert within the capsular bag of the eye while accommodating components of the lens (e.g., force translation arms 115 and dynamic membrane 143) can extend outside the capsular bag. The stabilization system can include an annular stabilization structure 171 positioned on a posterior side of the lens 100. The stabilization structure 171 can include a central opening 173 and a pair of wings 172 projecting outward from the annular stabilization structure 171. In aspects, the lens 100 can incorporate two force translation arms 115 and two wings 172. The wings 172 can be rotated 90 degrees around the circumference of the lens 100 relative to the arms 115 so that they are positioned between the two force translation arms 115. This arrangement prevents the outer elevation of the wings 172 from interfering with the motion of the force translation arms 115. FIG. 6B shows a side view of the lens 100 illustrating a plane of the outer elevation of the wings 172 extending upward toward a plane of the force translation arm 115.

The stabilization structure 171 can be sized and shaped to engage with corresponding surfaces of the lens body 105, such as posterior-facing surfaces of the posterior element 150. It should be appreciated the stabilization structure 171 can be molded as an integral part of the lens body 105 and need not be a separate component. Thus, where surfaces of components are described as being engaged with or bonded to one another it should be appreciated that this can include being molded together as a unitary piece.

The geometry of the stabilization structure 171 relative to the lens body 105 can improve fixation of the lens 100 within the capsular bag by capturing the edges of the capsulorhexis. An inner region 178 of the wings 172 can be separated a distance from the posterior-facing edge of the lens body 105 forming a groove 174 between the lens body 105 and the inner region 178 of the wings 172 (see FIG. 6B). When the wings 172 are implanted within the capsular bag so that the outer elevation of the wings 172 engage the anterior portion of the capsular bag, the edge of the capsulorhexis can be received and held within the groove 174.

The geometry of the stabilization structure 171 relative to the lens body 105 can also allow for fluid flow through the lens 100. For example, the coupling between the stabilization structure 171 and the lens body 105 can be discontinuous such that fluid trapped posterior to the lens 100 is allowed to escape the capsular bag. The lens body 105 near the groove 174 can additionally incorporate one or more apertures, slots, or cut-outs 177 extending through a sidewall of the lens body 105. In aspects, a first cut-out 177 in a sidewall of the lens body 105 can be positioned over an inner region 178 of a first wing 172 and a second cut-out 177 in the sidewall of the lens body 105 can be positioned over an inner region 178 of a second wing 172. The cut-outs 177 create a fluid channel (e.g., for viscoelastic within the capsular bag) from within the capsular bag on a posterior side of the lens 100, between the stabilization structure 171 and the posterior element 150, through the cut-outs 177, and into the anterior chamber on an anterior side of the lens 100. Thus, the lens 100 is prevented from sealing completely with the capsular bag. The size of the cut-outs 177 can vary. In aspects, the width of the cut-outs 177 approaches the width of the inner region of the wings 172. The cut-outs 177 allow for unimpeded flow of fluid through the lens 100 without impacting stability of the lens 100 during accommodative movements. The wings 172 can additionally incorporate one or more interruptions or apertures 175 as described above.

In aspects, the stabilization system 120 includes one or more stabilization haptics 160 (see, for example, FIGS. 5A-5F). The stabilization haptics 160 can be coupled to or integral with the lens body 105 away from the location of the at least one shape deformation membrane 140 or in a manner that does not interfere with movement of the shape deformation membrane 140. For example, the lens 100 can include two, opposing shape deformation membranes 140 and the stabilization system 120 can incorporate a pair of stabilization haptics 160 positioned on or coupled to the lens body 105 at a location that is between the two shape deformation membranes 140. As such, forces applied to the haptics 160 of the stabilization system 120 upon implantation are not transferred by the stabilization system 120 to the lens 100 in a manner that causes deformation of the fluid chamber 155 or shape change in the dynamic membrane 143. The internal portion 161 of the haptics 160 can be coupled to or integral with the lens body 105 such that the haptics 160 extend from the equator region 108. Alternatively, the internal portion 161 of the haptics 160 can be coupled to or integral with a region of the lens body 105 located more anteriorly or more posteriorly along the optical axis of the lens. The stabilization haptics 160 can be positioned within the capsular bag while the accommodating elements (e.g., force translation arms 115) extend outside the capsular bag. Alternatively, the haptics 160 can be connected to or integrated with the static element 150 as described above. In aspects, the haptics 160 are positioned relative to the lens body 105 such that they extend outward from the lens body 105 at a location that is generally more posteriorly oriented than the force translation arms 115. In this aspect, the one or more of the stabilization haptics 160 can be positioned and engaged within the capsular bag 22 to maintain the stability of the device 100 during motion of the force translation arms 115 to prevent and/or limit anterior, posterior, rotational movements of the device. In aspects, the haptics 160 are positioned relative to the lens body 105 such that they extend outward from the lens body 105 at a location that is generally more anteriorly oriented than the force translation arms 115 (see FIG. 5A). In this aspect, the one or more stabilization haptics 160 can be positioned and engaged within the ciliary sulcus to maintain the stability of the device 100 during motion of the force translation arms 115 to prevent and/or limit anterior and rotation movements of the device. In aspects, each of the stabilization haptics 160 is arranged relative to the force translation arms 115 such that an internal region 161 of the haptic 160 is coupled near a first side of a first force translation arm 115 and its terminal end 162 extends around a circumference of the lens 100 away from the first side of the first force translation arm 115 towards the other force translation arm 115 (see FIG. 5A). In aspects, each of the stabilization haptics 160 is arranged relative to the force translation arms 115 such that an internal region 161 is coupled near a first side of a first force translation arm 115 and its terminal end 162 extends over the force translation arm 115 from the first side towards an opposite site of the same force translation arm 115. A lens 100 having the terminal ends 162 positioned such that they extend over the force translation arms 115 reduces the width of the lens 100 providing for easier insertion and manipulation of the lens 100 into position in the eye. In aspects, the stabilization haptics 160 can be angled anteriorly relative to the plane of the force translation arms 115 such that their terminal ends 162 can engage the ciliary sulcus when the lens 100 is positioned, at least in part, within the capsular bag. The stabilization haptics 160 can then urge the lens 100 in a posterior direction further into the capsular bag. Regardless whether the terminal ends 162 of the stabilization haptics 160 extend over or within the same quadrant as the force translation arms 115 or between the force translation arms 115, the haptics 160 aid in preventing the force translation arms 115 from coming into contact with the iris by applying posterior-directing pressure on the lens 100.

Each haptic 160 can loop around along a curve such that the haptic 160 is configured to engage eye tissue along a greater portion of their overall length. The haptics 160 can be coaxial or coplanar with the force translation arms 115. The haptics 160 can also be positioned along a different axis than the force translation arms 115, for example, offset from the force translation arms 115 or angulated relative to the force translation arms 115. In aspects, the haptics 160 can be positioned at an angle in the range of 0-20 degrees or other degree angle relative to the force translation arms 115. Each haptic 160 can angle away from a plane of the lens such that a terminal end 162 of each haptic 160 sits on a different plane than the internal region 161 of the haptic 160 near where it couples to the lens body 105. For example, an implementation of an lens can have two haptics 160 and two opposing force translation arms 115. The force translation arms 115 in this implementation are coupled generally centrally relative to lens body 105 such that each of the force translation arms 115 between inner contact portion 137 and outer contact portion 135 are disposed generally along a central plane of the lens. Each of the two haptics 160 in this aspect is coupled to a region of the lens body 105 between the two force translation arms 115. The internal region 161 of each haptic 160 is positioned or coupled to the lens body 105 at a location that is slightly posterior to the central plane of the lens body 105 between anterior and posterior surfaces. Each haptic 160 curves from the internal region 161 towards the terminal end 162 such that the terminal end 162 of each haptic 160 is positioned on a plane that is posterior to a plane of the internal region 161 of the haptic 160. This results in the contact portion 135 of the force translation arms 115 arranged more anteriorly compared to the terminal end 162 of the haptics 160 such that they can be implanted in different anatomical locations within the eye. For example, the contact portions 135 of the force translation arms 115 can be positioned in the eye such that they make contact with the ciliary body apex 18 or the ciliary sulcus and the haptics 160 can extend more posteriorly than the force translation arms 115, for example, into the capsular bag 22. It should be appreciated, however, that the one or more haptics 160 can be positioned in the same plane as the force translation arms 115. Alternatively, the haptics 160 can be angled anteriorly in an effort to bias the lens in a posterior position (see FIGS. 5A-5F). In order to minimize contact with the iris, the haptics 160 can be used to hold lens body 105 and force translation arms 115 posterior relative to terminal end 162 which may be placed in the sulcus or capsular bag.

Any of the stabilization systems described herein can be arranged to be coaxial or coplanar with the force translation arms 115 or positioned along a different axis than the force translation arms 115 such that the stabilization system 120 is offset from the force translation arms 115 or angled relative to them as described above with respect to the haptics 160. Similarly, the stabilization systems 120 can be angled relative to the force translation arms 115 such that at least a portion of the stabilization system 120 angles away from a plane of the lens such that at least a portion of the stabilization system sits on a different plane than another portion of the stabilization system.

It should be appreciated that any of the stabilization systems described herein can be formed from silicone elastomer, polyurethane, PMMA, PVDF, PDMS, polyamide, polyimide, polypropylene, polycarbonate, or flexible acrylic materials that are hydrophobic or hydrophilic or any combination of those materials. The stabilization system may have a softer body that is reinforced with more rigid structures in order to provide its stabilizing function while maintaining flexibility for insertion and manipulation.

One or more portions of the stabilization system 120 described herein can incorporate biting elements to improve fixation within the eye. In aspects, the stabilization system 120 includes haptics 160 and the biting elements can be positioned near their terminal ends 162 to improve fixation of the haptic 160 within the eye. The haptics 160 can be any of a variety of haptic designs or combination of haptic designs including, but not limited to open-loop, closed-loop, plate-style, plate loop, monoblock-plate style, j-loop, c-loop, modified J-loop, multi-piece, single-piece, angulated, planar, offset, etc. Haptics 160 considered herein can include the Rayner designed haptics (Rayner Intraocular Lenses Ltd, East Sussex, UK), NuLens designed haptics (NuLens Ltd., Israel), Staar lens designs (Staar Surgical, Monrovia, CA), and others. In aspects, the stabilization system 120 whether including one or more haptics 160 or a 360 degree wing 172 can be formed of a biocompatible polymer such as silicone, polyurethane, PMMA, PVDF, PDMS, polyamide, polyimide, polypropylene, polycarbonate, PEEK, etc. or a combination of such materials. The stabilization system 120 can be formed of a material or configured to be foldable. In aspects, the stabilization system 120 is formed of a shape memory material.

The lenses described herein have improved mechanical stability, internally and/or externally, that results in a more efficient shape change. The shape change is more efficient in that it occurs only where desired (i.e. at the shape deformation membrane 140 and the dynamic membrane 143) without causing distortion or bulging elsewhere in the device that would take away from the desired shape change. The efficiency in shape change is due, in part, to the mechanical isolation of the moving parts. As will be described in more detail below, the one or more internal supports 110 provide enough rigidity to the lens 100 to mechanically isolate the moving parts to effectively and efficiently implement the shape change without inadvertent bulging or distortion in other parts of the device. The inner-facing region of the lenses 100 described herein can have reduced angles, rounded edges, and fewer dead zones improving the efficiency of the shape change achieved.

Figure 4D:
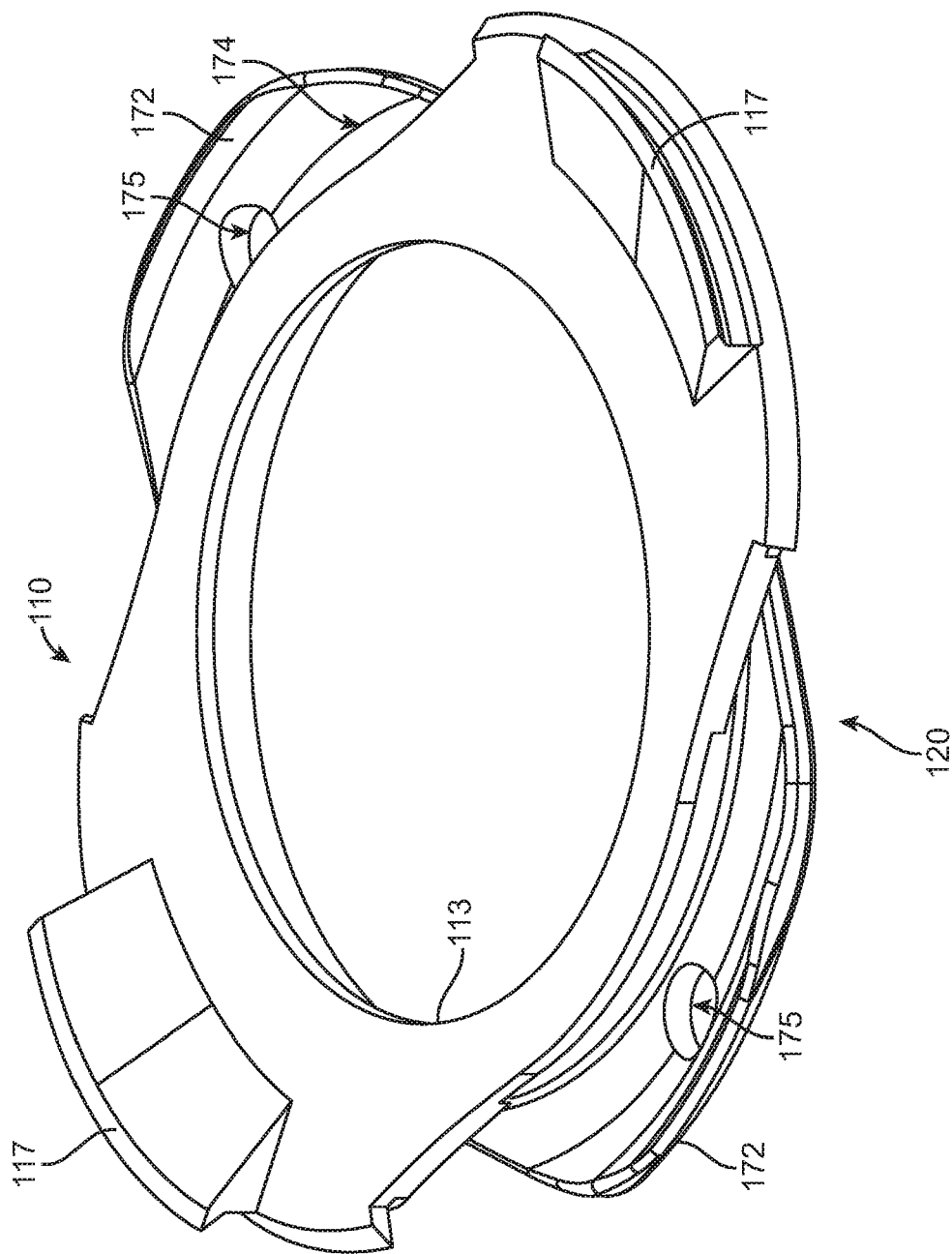
Figure 5D:
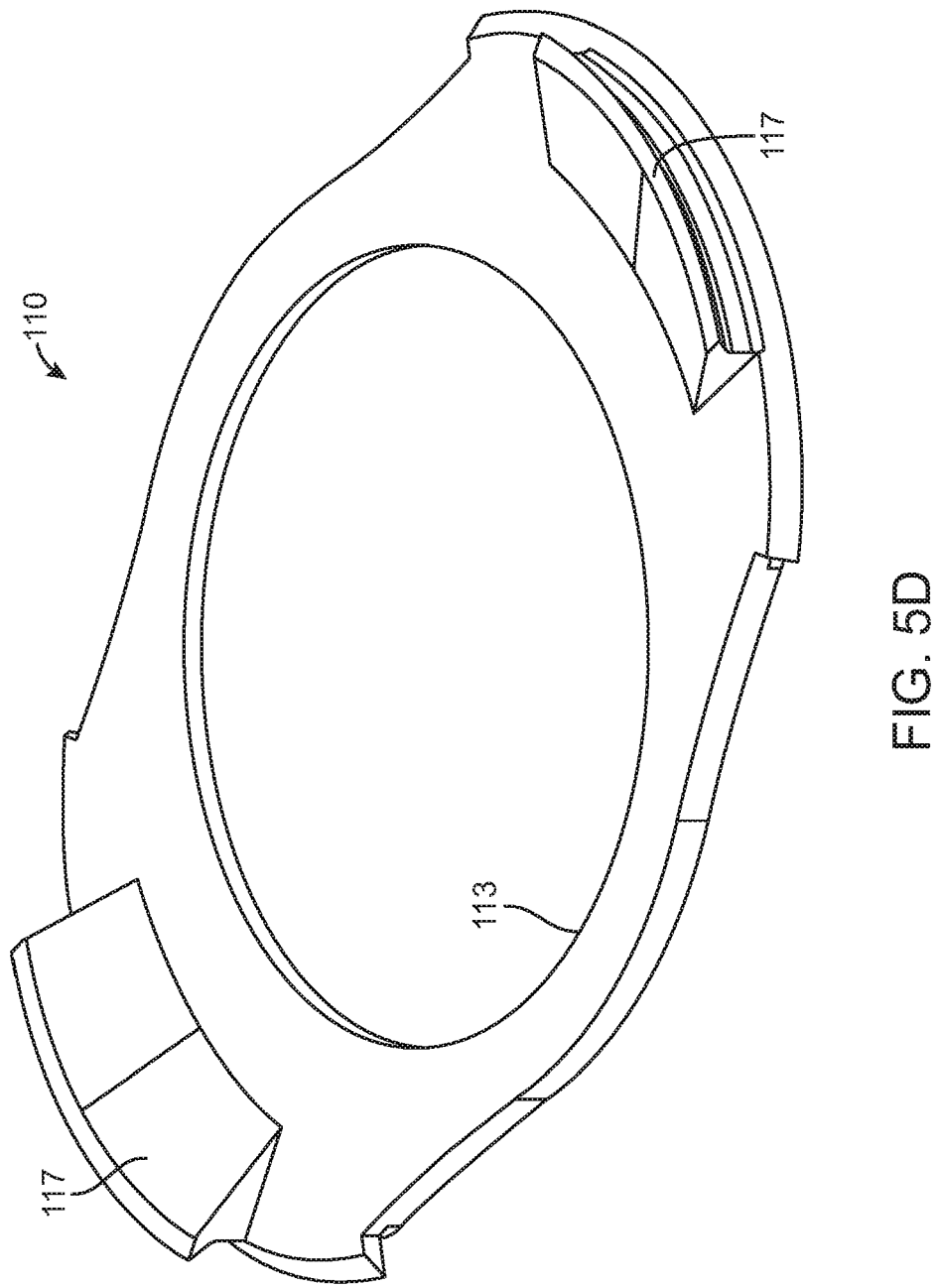
Figure 5E:
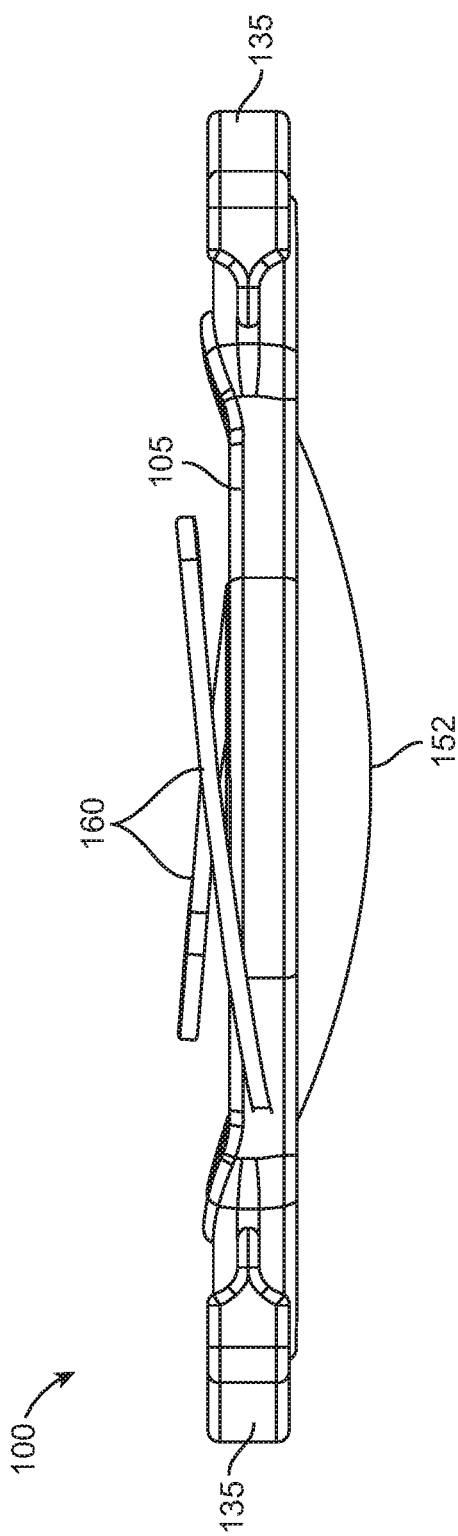
Figure 5F:
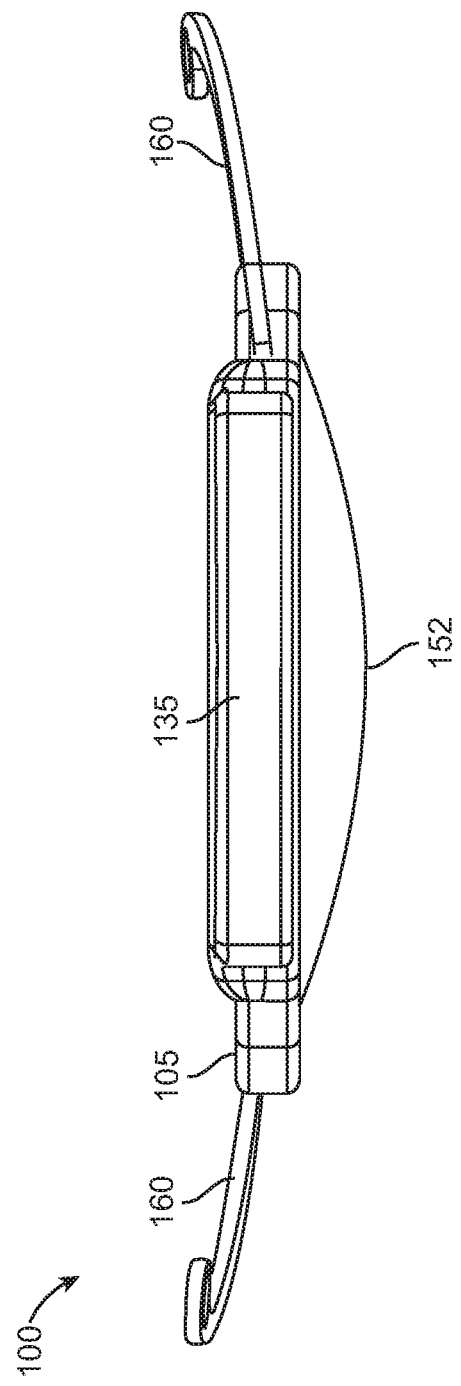

FIGS. 4A-64 and FIGS. 5A-5F illustrate an implementation of a lens having an internal support 110. The internal support 110 can function to mechanically isolate the optical elements (anterior and posterior) from stresses imparted by the stabilization system 120 to limit optical distortion. As best shown in FIG. 4D and FIG. 5D, the internal support 110 can be a ring-like element that defines a central aperture 113. The aperture 113 can have an inner diameter that is sized to receive at least a portion of the static lens element 150 therethrough. As described elsewhere herein, the static element 150 can have a flat surface 151 on a first side, a curved surface 152 on a second, opposite side, and a peripheral connecting ring having a sealing surface 154. The perimeter sealing surface 154 of the static element 150 can abut and seal against a posterior-facing, generally planar surface surrounding the aperture 113 of the internal support 110. The peripheral connecting ring of the static element 150 can be engaged by the inner diameter of the central aperture 113. Thus, the static element 150 can be held by the aperture 113 of the internal support 110 and the curved surface 152 available through the aperture toward the posterior side of the lens 100. The perimeter region 144 of the anterior optic 145 can be positioned over a planar, anterior-facing surface of the internal support 110 surrounding the aperture 113. As such the planar portion of the internal support 110 surrounding the aperture 113 is captured between the perimeter region 144 of the anterior optic and the sealing surface 154 of the static element 150. The internal support 110 can have an outer perimeter that generally matches an outer perimeter of the lens body 105. The lens body 105 is coupled to the outer perimeter of the internal support 110 (see FIGS. 4B and 5B). The outer perimeter of the internal support 110 can be spaced a distance internal to the peripheral membrane 140 such that upon movement of the force translation arms 115, the peripheral membrane 140 can be urged a distance inward to cause accommodative shape change. Thus, the lens body 105 can be coupled at a first location on an anterior surface of the internal support 110 and the lens body 105 can be coupled at a second location on a posterior surface of the internal support 110 such that the peripheral membrane 140 spans the distance between the first location and the second location (see FIGS. 4C and 5C). The distance between the first and second locations is defined by a width of wedge-shaped features 117 near the outer perimeter. The presence of these features 117 limits movement of the force translation arms 115 and reduces the risk of tearing during implantation in the eye such as by injection. The features 117 can have a generally wedge shape such that a thicker portion of the feature 117 is positioned more peripherally facing the peripheral membrane 140 and tapers toward the central aperture 113. An outer facing surface of the features 117 can be concave or otherwise angled inward to ensure the peripheral membrane 140 avoids contact with the feature 117 during movement of the force translation arms 115. It should be appreciated that the feature 117 need not be wedge shaped. For example, the internal support 110 may include features 117 that are more square or rectangular in cross-section such that they do not taper toward the central aperture 113.

Generally, the material of the internal support 110 has enough rigidity to mechanically isolate the optical elements, particularly when the lens 100 is placed under stress imparted by stabilization haptics 160. FIGS. 5A-5F illustrate an implementation of a lens 100 having an internal support 110 configured to mechanically isolate the optical portions of the device from stresses imparted by the stabilization haptics 160. The internal support 110 is configured to prevent optical distortions of the central area even during movement of the stabilization haptics 160 such that the stabilization haptics 160 impart no shape change to the optical portions of the device such as the dynamic membrane 143 or the anterior optic 143. The strength of the internal support 110 relative to other portions of the lens 100 such as the shape deformation membrane 140 and the dynamic membrane 143 provides increased durability during manipulation and handling of the lens during insertion.

Regardless the configuration, the internal support 110 can limit efficiency-sapping lens movements in regions of the lens 100 other than where accommodative movements are desired. The internal support 110 functions to focus all ciliary-induced pressure toward the central, dynamic membrane 143. The internal support 110 mechanically isolates dynamic areas of the lens 100 and structurally reinforces non-dynamic areas of the lens 100 thereby focusing the shape change only where desired for accommodation—the side deformation membrane 140 via movements of the force translation arm 115 and the dynamic membrane 143 from the increased pressure within the fluid-filled chamber 155. The geometry and rigidity of the internal support 110 serves to mechanically prevent other lens regions from deforming under the increased internal pressure of the fluid-filled capsule. The internal support 110 can be formed of any of a variety of materials or combination of materials that can be opaque or clear, but are generally more rigid than the moveable parts of the lens 100. In aspects, each solid component of the lens 100 is formed of the same material, which provides advantages from a manufacturing standpoint. The material of the various solid components may be the same (i.e. silicone), but the mechanical properties of the various solid components may be unique depending on what function the component performs for the lens (i.e. shape change or force transfer or centering and stabilization). One solid component of the lens may be more rigid than another component of the lens (e.g. the internal support 110 compared to the peripheral membrane 140), but both solid components may be the same material. The more rigid solid component may be more rigid due to that component's geometry and dimensional differences compared to the less rigid solid component. As such, the internal support 110 and the membranes 140, 143 can be formed of the same silicone material, but because the membranes 140, 143 have a significantly decreased thickness compared to the internal support 110 the membranes 140, 143 are easily deformed upon application of a compressive force whereas the internal support 110 is not easily deformed. In some implementations, the internal support 110 can be a silicone elastomer (e.g. silicone PDMS 70-90 shoreA) and the membranes 140, 143 can be a silicone elastomer (e.g. silicone PDMS 20-50 shoreA). Additionally, the internal support 110 can include a geometry that imparts a higher rigidity and stiffness relative to the membranes 140, 143.

The various components and features of the lenses described herein can be incorporated in any of a variety of combinations. As such, description of a particular feature shown with respect to a particular drawing is not intended to be limiting in that the feature can be incorporated into another implementation of a lens described herein. For example, the lenses described herein can include a stabilization system that incorporates one or more features of the stabilization systems described herein. Further, the lens having the stabilization system features can be combined with any of a variety of features described with respect to the force translation arm 115 or the shape deformation membrane 140, for example.

Suitable materials or combinations of materials for the preparation of the various solid optical components of the devices disclosed herein are provided throughout. It should be appreciated that other suitable materials are considered. U.S. Patent Publication Nos. 2009/0234449, 2009/0292355 and 2012/0253459, which are each incorporated by reference herein in their entirety, provide further examples of other materials suitable for forming certain components for the devices described herein. One or more solid optical components of the lens body 105 can be integral with one another in that they are formed of the same material. For example, the internal supports 110 can be thickened regions of the perimeter region 144 of the anterior optic 145. Similarly, the shape deformation membrane 140 can be integral with one another having certain physical properties, such as a thickness or flexibility, to provide a desired function. Alternatively, one or more of the solid optical components of the lens body 105 can be coupled together by techniques known in the art. As such, the one or more solid optical components of the lens body 105 can be formed of the same materials or different materials. One or more of the supports 110, perimeter region 144, dynamic membrane 145, and shape deformation membrane 140 can be formed of an optically clear, low modulus elastomer such as silicone, urethane, flexible acrylic, or flexible inelastic film such as polyethylene, as well as halogenated elastomers such as fluorosilicone elastomers. In aspects, the liquid optical material filling the fluid chamber 155 is a copolymer of Formula (I) and the solid optical components forming the fluid chamber 155 (e.g. inner-facing surfaces of the shape deformation membrane 140, the static element 150, the inner supports 110, the perimeter region 144 and the dynamic membrane 143 of the anterior optic 145) are formed of a silicone elastomer. In aspects, the liquid optical material filling the fluid chamber 155 is a copolymer of Formula (A) and the solid optical components forming the fluid chamber 155 (e.g. inner-facing surfaces of the shape deformation membrane 140, the static element 150, the inner supports 110, the perimeter region 144 and the dynamic membrane 143 of the anterior optic 145) are formed of a silicone elastomer. In aspects, the liquid optical material filling the fluid chamber 155 is a copolymer of Formula (B) and the solid optical components forming the fluid chamber 155 (e.g. inner-facing surfaces of the shape deformation membrane 140, the static element 150, the inner supports 110, the perimeter region 144 and the dynamic membrane 143 of the anterior optic 145) are formed of a silicone elastomer. In aspects, the liquid optical material filling the fluid chamber 155 can be a fluorosilicone oil and the solid optical components forming the fluid chamber 155 (e.g. inner-facing surfaces of the shape deformation membrane 140, the static element 150, the inner supports 110, the perimeter region 144 and the dynamic membrane 143 of the anterior optic 145) are formed of a silicone elastomer. In aspects, the liquid optical material filling the fluid chamber 155 is a silicone oil and the solid optical components forming the fluid chamber 155 are formed of a fluorosilicone elastomer. In aspects, the liquid optical material filling the fluid chamber 155 is an aromatic or phenyl-substituted oil such as phenylsilicone oil and the solid optical components forming the fluid chamber 155 are formed of a halogenated silicone elastomer such as fluorosilicone elastomer. The combinations of materials are chosen to optimize stability of the lens, prevent swelling and maintaining optimum refractive index. The liquid optical materials are described in more detail above.

In aspects, the force translation arms 115 can be a rigid polymer formed of silicone, polyurethane, PMMA, PVDF, PDMS, polyamide, polyimide, polypropylene, polycarbonate, etc., or combinations thereof. In some implementations, the force translation arms 115 can be an element reinforced with PMMA. In aspects, the lens is formed of all silicone materials including the posterior static element 150 and the force translation arms 115. The stabilization system 120 can be formed of a more rigid silicone or can be formed of or incorporate polyimide. For example, the stabilization haptics 160 and the wing 172 can be polyimide.

The lenses described herein can provide focusing power across the full accommodative range from distance to near by mechanically and functionally interacting with eye tissues typically used by a natural lens such as the ciliary body, ciliary processes, and the zonules, to effect accommodation and disaccommodation. The devices described herein can include an accommodative mechanism including one or more force translation arms configured to be positioned in the eye such that they harness movements of one or more ciliary structures and translate the movements into functional forces to drive shape change of the lens body for accommodation and disaccommodation in a manner independent of capsular bag movements. The lenses described herein can achieve an optical power change in the range of 1 diopter (1D) to 3D up to about 5D or 6D. The forces generated by these tissues are functionally translated to the devices described herein causing a power change to more effectively accommodate. The lenses described herein can further include a stabilization system separate from the accommodative mechanism that is configured to be positioned, for example, within the capsular bag. The devices described herein obviate known issues that tend to occur due to capsular fibrosis described above. It should be appreciated that the devices described herein can be configured to harness movements of one or combinations of ciliary structures including, but not limited to, the ciliary muscle, the ciliary body, ciliary processes, and zonules. For the sake of brevity, the term "ciliary structure" may be used herein to refer to any of the one or more ciliary structures for which movements can be harnessed by the force translation arms to effect accommodation of the lens body.

The devices described herein can be implanted in the eye to replace a diseased, natural lens. The devices can be implanted as a supplement of a natural lens (phakic patient) or an intraocular lens previously implanted within a patient's capsular bag (pseudophakic patient). The lenses described herein can be used in combination with intraocular lenses described in US 2009/0234449, US 2009/0292355, US 2012/0253459, WO 2015/148673, and WO 2018/081595, which are each incorporated by reference herein in their entirety. As such, the lenses described herein can be used independently or as so-called "piggyback" lenses. Piggyback lenses can be used to correct residual refractive errors in phakic or pseudophakic eyes. The primary lens used to replace the natural lens is generally thicker and usually has a power that can be in the range of ±10D to ±25D. The thicker, larger power lenses generally do not accommodate. In contrast, the supplemental lens need not provide significant optical power to the system. The supplemental lens can be relatively thin compared to the primary lens and can undergo more accommodation. Shape change and movement of the thinner lens is generally more easily accomplished relative to a thick primary lens. The lenses described herein can be used independently and need not be used in combination as piggyback lenses with the natural lens or an implanted lens. One or more components of the lenses described herein can be configured to be positioned in the sulcus 16, against the ciliary processes, within the capsular bag 22 or a combination thereof.

The devices and systems described herein can incorporate any of a variety of features. Elements or features of one implementation of a device and system described herein can be incorporated alternatively or in combination with elements or features of another implementation of a device and system described herein as well as the various implants and features described in US 2009/0234449, US 2009/0292355, US 2012/0253459, WO 2015/148673, and WO 2018/081595, which are each incorporated by reference herein in their entireties. For the sake of brevity, explicit descriptions of each of those combinations may be omitted although the various combinations are to be considered herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The lens incorporating a fluid chamber filled by the liquid optical materials described herein need not be an accommodating lens and need not be configured to be implanted in an eye. The lens also need not incorporate each and every feature of the exemplary lenses described with respect to the figures. The lens may be an eyeglass lens, monocular lens, binocular lens, telescope lens, spotting scope lens, telescopic gun sight lens, theodolite lens, microscope lens, camera lens, imaging lens, or other medical equipment lenses.

In aspects, description is made with reference to the figures. However, certain aspects may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "an aspect," "one aspect," "one implementation, "an implementation," or the like, means that a particular feature, structure, configuration, or characteristic described is included in at least one embodiment, aspect, or implementation. Thus, the appearance of the phrase "one embodiment," "an embodiment," "one aspect," "an aspect," "one implementation, "an implementation," or the like, in various placed throughout this specification are not necessarily referring to the same embodiment, aspect, or implementation. Furthermore, the particular features, structures, configurations, or characteristics may be combined in any suitable manner in one or more implementations.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "front," "side," and "back" as well as "anterior," "posterior," "caudal," "cephalad" and the like or used to establish relative frames of reference, and are not intended to limit the use or orientation of any of the devices described herein in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples, embodiments, aspects, and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

Embodiments 1 to 50.

Embodiment 1. A copolymer of Formula (B):

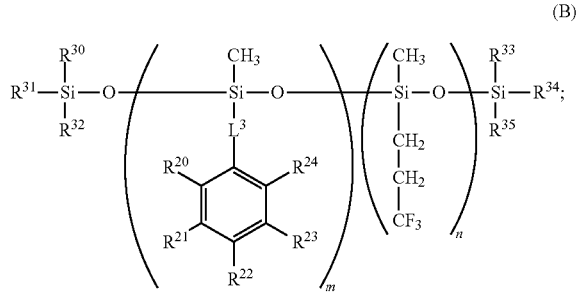

wherein: $R^{20}$, $R^{21}$, $R^{22}$, $R^{23}$, and $R^{24}$ are each independently hydrogen, fluorine, or $C_{1-4}$ alkyl substituted with at least one fluorine; $L^3$ is independently —$(CH_2)_2$— or —$CH(CH_3)$—; $R^{30}$, $R^{31}$, $R^{32}$, $R^{33}$, $R^{34}$, and $R^{35}$ are each independently —$CH_3$ or —$CF_3$; and m and n are each independently an integer from 1 to 20, where the ratio of m:n is from about 25:75 to about 75:25.

Embodiment 2. The copolymer of Embodiment 1, wherein $R^{20}$ and $R^{24}$ are each independently hydrogen; and $R^{21}$, $R^{22}$, and $R^{23}$ are each independently fluorine.

Embodiment 3. The copolymer of Embodiment 1, wherein at least one of $R^{20}$, $R^{21}$, $R^{22}$, $R^{23}$, and $R^{24}$ is fluorine or $C_1$-$C_2$ alkyl substituted with at least one fluorine.

Embodiment 4. The copolymer of Embodiment 1, wherein $R^{20}$, $R^{21}$, $R^{22}$, $R^{23}$, and $R^{24}$ are each independently hydrogen, fluorine, or methyl substituted with at least one fluorine.

Embodiment 5. The copolymer of Embodiment 1, wherein $R^{20}$, $R^{21}$, and $R^{24}$ are each independently hydrogen; and $R^{22}$ and $R^{23}$ are each independently fluorine.

Embodiment 6. The copolymer of Embodiment 1, wherein $R^{20}$, $R^{21}$, $R^{23}$, and $R^{24}$ are each independently hydrogen, and $R^{22}$ is —$CF_3$.

Embodiment 7. The copolymer of any one of Embodiments 1 to 6, wherein $R^{30}$, $R^{31}$, $R^{32}$, $R^{33}$, $R^{34}$, and $R^{35}$ are —$CH_3$.

Embodiment 8. The copolymer of any one of Embodiments 1 to 6, wherein $R^{30}$, $R^{31}$, $R^{32}$, $R^{33}$, $R^{34}$, and $R^{35}$ are —$CF_3$.

Embodiment 9. The copolymer of any one of Embodiments 1 to 8, wherein m and n are each independently an integer from 5 to 15.

Embodiment 10. The copolymer of any one of Embodiments 1 to 9, wherein the ratio of m:n is from about 40:60 to about 50:50.

Embodiment 11. The copolymer of Embodiment 10, wherein the ratio of m:n is about 45:55.

Embodiment 12. The copolymer of any one of Embodiments 1 to 11 having a number average molecular weight from about 2,000 to about 5,000.

Embodiment 13. The copolymer of Embodiment 12 having a number average molecular weight from about 3,000 to about 4,000.

Embodiment 14. The copolymer of Embodiment 13 having a number average molecular weight of about 3,500.

Embodiment 15. A copolymer of Formula (A):

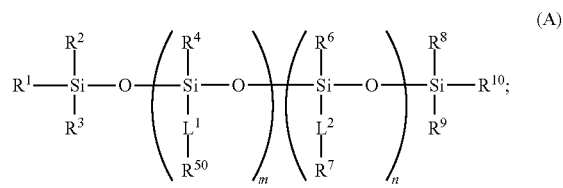

wherein: $R^1$, $R^2$, $R^3$, $R^8$, $R^9$, and $R^{10}$ are each independently hydrogen, substituted or unsubstituted alkyl, substituted or unsubstituted heteroalkyl, substituted or unsubstituted aryl, or substituted or unsubstituted heteroaryl; $R^4$ and $R^6$ are each independently hydrogen, substituted or unsubstituted alkyl, substituted or unsubstituted heteroalkyl, substituted or unsubstituted aryl, or substituted or unsubstituted heteroaryl; $L^1$ and $L^2$ are each independently a bond, substituted or unsubstituted alkylene, or substituted or unsubstituted heteroalkylene; $R^5$ is independently $R^{5A}$-substituted aryl, $R^{5A}$-substituted heteroaryl, $R^{5A}$-substituted alkyl, or $R^{5A}$-substituted heteroalkyl; wherein $R^{5A}$ is independently fluorine, $R^{5B}$-substituted alkyl, or $R^{5B}$-substituted heteroalkyl; wherein $R^{5B}$ is fluorine; $R^7$ is independently unsubstituted or $R^{7A}$-substituted alkyl, unsubstituted or $R^{7A}$-substituted heteroalkyl, unsubstituted or $R^{7A}$-substituted aryl, or unsubstituted or $R^{7A}$-substituted heteroaryl; wherein $R^{7A}$ is independently fluorine, $R^{7B}$-substituted alkyl, or $R^{7B}$-substituted heteroalkyl; wherein $R^{7B}$ is fluorine; and m and n are each independently an integer from 1 to about 100.

Embodiment 16. The copolymer of Embodiment 15, wherein $R^5$ is $R^{5A}$-substituted aryl; wherein $R^{5A}$ is independently fluorine or $C_1$-$C_4$ alkyl substituted with at least one fluorine.

Embodiment 17. The copolymer of Embodiment 15, wherein $R^5$ is $R^{5A}$-substituted alkyl; where $R^{5A}$ is independently fluorine or $C_1$-$C_4$ alkyl substituted with at least one fluorine.

Embodiment 18. The copolymer of Embodiment 15, wherein $R^{5A}$ is $R^{5B}$-substituted alkyl.

Embodiment 19. The copolymer of any one of Embodiments 15 to 18, wherein $R^7$ is independently unsubstituted or $R^{7A}$-substituted alkyl or unsubstituted or $R^{7A}$-substituted aryl; wherein $R^{7A}$ is independently fluorine or $R^{7B}$-substituted alkyl; wherein $R^{7B}$ is fluorine.

Embodiment 20. The copolymer of any one of Embodiments 15 to 18, wherein $R^7$ is independently unsubstituted or $R^{7A}$-substituted alkyl.

Embodiment 21. The copolymer of any one of Embodiments 15 to 18, wherein $R^{7A}$ is $R^{7B}$-substituted alkyl.

Embodiment 22. The copolymer of Embodiment 15, wherein $R^1$, $R^2$, $R^3$, $R^8$, $R^9$, and $R^{10}$ are each independently hydrogen, unsubstituted $C_1$-$C_6$ alkyl, $C_1$-$C_6$ alkyl substituted with at least one fluorine, $C_1$-$C_6$ alkyl substituted with a 6 membered aryl that is substituted with at least one fluorine, or 6 membered aryl substituted with at least one fluorine; $R^4$ and $R^6$ are each independently hydrogen, substituted or unsubstituted $C_1$-$C_6$ alkyl, or substituted or unsubstituted phenyl; $L^1$ and $L^2$ are each independently a bond or a substituted or unsubstituted $C_1$-$C_6$ alkyl; $R^5$ is 5 or 6 membered $R^{5A}$-substituted aryl where $R^{5A}$ is independently fluorine or $C_1$-$C_4$ alkyl substituted with at least one fluorine; $R^7$ is independently phenyl, unsubstituted $C_1$-$C_6$ alkyl, or $C_1$-$C_6$ alkyl substituted with at least one fluorine; and m and n are each independently an integer from 1 to about 50.

Embodiment 23. The copolymer of Embodiment 15, wherein: $R^1$, $R^2$, $R^3$, $R^8$, $R^9$, and $R^{10}$ are each independently hydrogen, unsubstituted methyl, or —$CF_3$; $R^4$ is independently hydrogen or unsubstituted methyl; $R^6$ is independently hydrogen, unsubstituted methyl, or unsubstituted phenyl; $L^1$ is independently unsubstituted methylene, methylene substituted with methyl, unsubstituted ethylene, ethylene substituted with methyl, unsubstituted propylene, or propylene substituted with methyl; $L^2$ is a independently bond, unsubstituted methylene, unsubstituted ethylene, or unsubstituted propylene; $R^5$ is phenyl substituted with 1 to 5 fluorine; $R^7$ is phenyl substituted with 1 to 5 fluorine or methyl substituted with 1 to 3 fluorine; and m and n are each independently an integer from 1 to about 25

Embodiment 24. The copolymer of any one of Embodiments 15 to 23, wherein the ratio of m:n is from about 10:90 to about 90:10.

Embodiment 25. The copolymer of Embodiment 24, wherein the ratio of m:n is from about 20:80 to about 80:20.

Embodiment 26. The copolymer of Embodiment 25, wherein the ratio of m:n is from about 30:70 to about 70:30.

Embodiment 27. The copolymer of Embodiment 26, wherein the ratio of m:n is from about 40:60 to about 60:40.

Embodiment 28. The copolymer of any one of Embodiments 15 to 27, wherein the copolymer has a number average molecular weight of about 500 to about 10,000.

Embodiment 29. The copolymer of Embodiment 28, wherein the copolymer has a number average molecular weight of about 1,000 to about 6,000.

Embodiment 30. The copolymer of Embodiment 29, wherein the copolymer has a number average molecular weight of about 2,000 to about 5,000.

Embodiment 31. A composition comprising a plurality of the copolymer of any one of Embodiments 1 to 30.

Embodiment 32. The composition of Embodiment 31 having a viscosity from about 500 cP to about 10,000 cP.

Embodiment 33. The composition of Embodiment 32 having a viscosity from about 1,000 cP to about 2,000 cP.

Embodiment 34. The composition of any one of Embodiments 31 to 33 having a refractive index from about 1.40 to about 1.50.

Embodiment 35. The composition of Embodiment 34 having a refractive index from about 1.43 to about 1.46.

Embodiment 36. The composition of any one of Embodiments 31 to 35 having a light transmittance of at least 95% in the visible light range of 400 nm to 700 nm.

Embodiment 37. A lens comprising: (i) an anterior portion comprising a refractive optical element; (ii) a posterior portion; and (iii) an enclosed cavity between the anterior portion and the posterior portion, wherein the enclosed cavity comprises the copolymer of any one of Embodiments 1 to 30 or the composition of any one of Embodiments 31 to 36.

Embodiment 38. The lens of Embodiment 37, wherein the anterior portion and the posterior portion comprise a silicone elastomer.

Embodiment 39. The lens of Embodiment 37 or 38, wherein the lens is an intraocular lens.

Embodiment 40. A method of treating a cataract in an eye of a patient in need thereof, the method comprising implanting the intraocular lens of Embodiment 39 into the eye of the patient.

Embodiment 41. A process for producing the copolymer of any one of Embodiments 1 to 30, the process comprising: (i) contacting an $R^{60}$-substituted alkyl or an $R^{60}$-substituted aryl with a copolymer of Formula (C) to produce a composition comprising the copolymer of Formula (A) or (B); and (ii) removing impurities from the composition; thereby producing the copolymer of Formula (A) or (B); wherein $R^{60}$ is fluorine, $R^{61}$-substituted alkyl, $R^{61}$-substituted heteroalkyl, $R^{61}$-substituted aryl, or $R^{61}$-substituted heteroaryl; wherein $R^{61}$ is fluorine; wherein the copolymer of Formula (C) is:

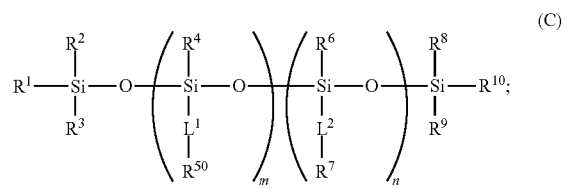

wherein $R^{50}$ is hydrogen, substituted or unsubstituted alkyl, or substituted or unsubstituted aryl.

Embodiment 42. The process of Embodiment 41, wherein $R^{50}$ is unsubstituted methyl.

Embodiment 43. The process of Embodiment 41 or 42, wherein removing impurities from the composition comprises washing the composition with an organic solvent to remove impurities from the composition.

Embodiment 44. The process of Embodiment 43, wherein the organic solvent is dimethylsulfoxide, dimethylformamide, acetonitrile, dimethylacetamide, acetone, tetrahydrofuran, dioxane, N-methyl-2-pyrrolidone, diethylether, methanol, ethanol, isopropanol, pyridine, acetic acid, triethylamine, diisopropylethylamine, carbon tetrachloride, chloroform, dichloromethane, water, $D_2O$, hexane, cyclohexane, pentane, 2-methylpentane, 3-methylpentane, 2,3-dimethylbutane, 2,2-dimethylbutane, heptane, octane, xylene, benzene, toluene, or a combination of two or more thereof.

Embodiment 45. The process of Embodiment 44, wherein the organic solvent is hexane, dichloromethane, or a mixture of hexane and dichloromethane.

Embodiment 46. The process of any one of Embodiments 43 to 45, comprising washing the composition with the liquid hydrocarbon at least 10 times to remove impurities from the composition.

Embodiment 47. The process of Embodiment 41 or 42, wherein removing impurities from the composition comprises extracting impurities from the composition with supercritical $CO_2$.

Embodiment 48. The process of any one of claims 41 to 47, wherein removing impurities comprises contacting the composition with a silicone elastomer.

Embodiment 49. The process of any one of Embodiments 41 to 48, wherein step (i) comprises contacting $R^{60}$-substituted aryl with a copolymer of Formula (C) to produce a composition comprising the copolymer of Formula (A) or (B); wherein $R^{60}$ is fluorine or $C_1$-$C_6$ alkyl substituted with at least one fluorine.

Embodiment 50. The process of Embodiment 49, wherein $R^{60}$-substituted aryl is a copolymer of Formula (D):

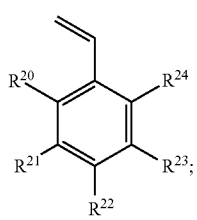

(D)

wherein $R^{20}$, $R^{21}$, $R^{22}$, $R^{23}$, and $R^{24}$ are each independently hydrogen, fluorine, or $C_1$-$C_4$ alkyl substituted with at least one fluorine; provided that $R^{20}$, $R^{21}$, $R^{22}$, $R^{23}$, and $R^{24}$ are not all hydrogen.

Embodiment 51. The process of Embodiment 50, wherein the compound of Formula (D) is a compound of Formula (D1) or (D2) or (D3):

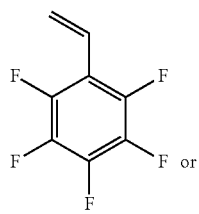

(D1)

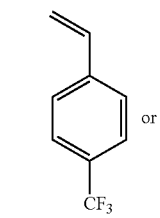

(D2)

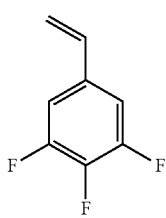

(D3)

Embodiment 52. The process of any one of Embodiments 41 to 48, wherein step (i) comprises contacting $R^{60}$-substituted alkyl with a copolymer of Formula (C) to produce a composition comprising the copolymer of Formula (A) or (B); wherein $R^{60}$ is fluorine or $C_1$-$C_6$ alkyl substituted with at least one fluorine.

Embodiment 53. The process of Embodiment 52, wherein $R^{60}$-substituted alkyl is a compound of Formula (E):

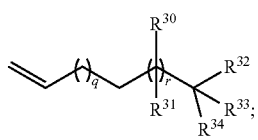

(E)

wherein q and r are each independently an integer from 0 to 6; and $R^{30}$, $R^{31}$, $R^{32}$, $R^{33}$, and $R^{34}$ are each independently hydrogen, fluorine, or $C_1$-$C_4$ alkyl substituted with at least one fluorine; provided that $R^{30}$, $R^{31}$, $R^{32}$, $R^{33}$, and $R^{34}$ are not all hydrogen.

EXAMPLES

The following examples are for purposes of illustration only, and are not intended to limit the spirit or scope of the disclosure and claims.

Example 1

Processes for preparing and modifying polymers are well known in the art. In the present disclosure, the fluorosilicone polymers and copolymers were made by the process descried herein. An RBF was loaded with a stir bar, toluene (2 mL) and a poly(silane) (e.e., HDP-111, HMS-301, HMS-501, HPM-502, all by Gelest, Inc., Morrisville, PA) (3 g, ~2.86 mmol, ~18.9 mmol Si—H). Add inhibitor free 4-fluorostyrene (3.3 g, 18.9 mmol, ~1.0 equiv/Si—H) was added thereof. The inhibitor free 4-fluorostyrene was made by passing commercial sytrene through a neutral alumina plug and used immediately. Thereafter Karstedt's catalyst was used as a solution in toluene (~2% Pt) (50 µL) and placed in a 50° C. oil bath. The reaction stayed fluid and pale yellow.

After three hours, volatile solvent was removed via rotary evaporation. $^1$H NMR was used to monitor vinyl and silane protons. The reaction did not show any residual vinyl protons from the styrenic sub-units. If residual silane protons remained, additional equivalents of styrene-based units was added to consume residual silanes, followed by additional heating for 3 hours (e.g, 3-5 hours). If residual vinyl protons and no silane protons remained, the reaction was stopped and volatiles were removed under reduced pressure. If residual vinylic and silane protons were present, an additional aliquot of Karstedt catalyst was added, and the reaction was placed back into oil bath for another 3-5 hours. The reaction was monitored until complete.

Dilute reaction with dichloromethane and add charcoal. Stir or sonicate for 15-30 minutes. Filter thru a plug of Celite and concentrate sample via rotatory evaporation.

Although this example refers to inhibitor free 4-fluorostyrene as a starting product, the skilled artisan will appreciate that other reaction products were used in the following examples, e.g., 4-(trifluoromethyl)styrene, 2,3,4,5,6-pentafluorostyrene. Other fluorosilicone copolymers can be made following the method described herein using other starting materials, such as 3-fluorostyrene, 2-fluorostyrene, 2,6-difluorostyrene, 3-(trifluoromethyl)styrene, 2-(trifluoromethyl)stryene, and the like.

Example 2

The inventors designed an asymmetric, uniform polymer with polyphenyl-(dimethylhydrosiloxy)siloxane, hydride-terminated 50-80 Cst as the base, and added various fluoroalkanes to create a molecule that balances the refractive index and solubility parameters within each repeat unit. In particular, the compound of Formula (II), i.e., HDP-111 by Gelest, Inc., was reacted with the compound of Formula (D) or (E) following the process described in Example 1 to create a fluorosilicone polymer of Formula (VIII), as described herein. If the refractive index of the resulting polymer was too low or too high, the fluoro content of the compound of Formula (D) or (E) was varied. In addition, the molecular weight of the compound of Formula (II) was varied to adjust the viscosity.

When the compound of Formula (D) was a monofluorostyrene, the solubility of the resulting polymer was not sufficient. When the compound of Formula (D) was a trifluorostyrene or a penta-fluorostyrene, the material was not liquid. When the compound of Formula (E) was used, the resulting polymer was solid. It is hypothesized that the polymer resulting from the combination of the compound of Formula (II) and the compound of Formula (D) or (E) was too bulky to provide the desired characteristics needed for the fluorosilicone oil.

Example 3

The inventors designed and synthesized a copolymer with a hydride based copolymer as the base, and added functional groups to produce the solubility and refractive properties needed to reach the final product specifications. In particular, the compound of Formula (IV), i.e., either HMS-501 or HMS-301, by Gelest, Inc., was reacted with the compound of Formula (D) or (E) following the process described in Example 1 to create a fluorosilicone copolymer of Formula (IX), as described herein.

If the refractive index of the resulting polymer was too low, the fluoro content of the compound of Formula (D) or (E) was varied. If the resulting copolymer was too soluble, the hydide concentration of the copolymer of Formula (IV) was varied. In addition, the molecular weight of the compound of Formula (II) was varied to adjust the viscosity.

When the compound of Formula (D) was a monofluorostyrene, the solubility of the resulting copolymer was not sufficient. When a the compound of Formula (D) was a trifluorostyrene, the resulting copolymer had a good refractive index and a good solubility. When the compound of Formula (D) was a pentafluoro-styrene, the resulting copolymer was partially solid. When the compound of Formula (E) was used, the resulting copolymer was solid and the refractive index was too low. A 50/50 hydride/dimethyl was needed to bring solubility to appropriate level.

Example 4

The inventors designed and synthesized a fluoro-phenyl copolymer, where the solubility and refractive properties were balanced by the amount of fluoro in one section of the copolymer and the percentage of that section of the overall copolymer. In particular, the compound of Formula (VII), i.e., HPM-502 by Gelest, Inc., was reacted with the compound of Formula (D) following the process described in Example 1 to create a fluorosilicone copolymer of Formula (X), as described herein.

If the refractive index of the resulting polymer was too low or too high, the fluoro content of the compound of Formula (D) was varied. If the resulting copolymer was too soluble, the hydide concentration of the copolymer of Formula (VII) was varied. In addition, the molecular weight of the compound of Formula (VII) was varied to adjust the viscosity.

If the compound of Formula (D) was a monofluoro-, trifluoro-, or pentafluoro-styrene, the resulting copolymer was solid.

Example 5

The inventors designed and synthesized a hydride-based copolymer as the base, while the other moiety of the copolymer was a trifluoropropyl silicone. The functional groups added in the reaction contain the solubility and refractive properties needed to reach the final product specifications.

In particular, the base copolymer having the following structure (commercially available from Gelest, Inc.):

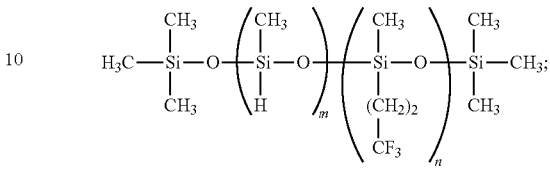

wherein the molar ratio of hydride:trifluoropropyl (e.g., m:n) was 18:82 or 38:62; was reacted with a compound of Formula (D1) following the process described in Example 1 to produce the following copolymer:

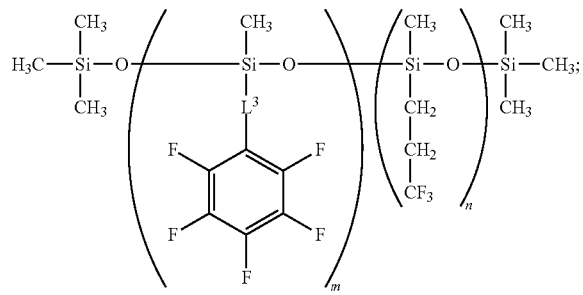

where $L^3$ is independently —$(CH_2)_2$— or —$CH(CH_3)$—.

The base copolymer having the following structure (commercially available from Gelest, Inc.):

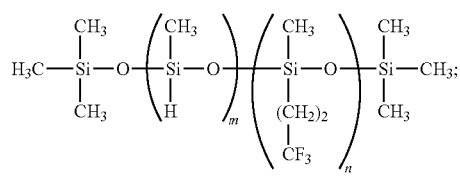

wherein the molar ratio of hydride:trifluoropropyl (e.g., m:n) was 18:82 or 38:62; was reacted with a compound of Formula (D2) following the process described in Example 1 to produce the following copolymer:

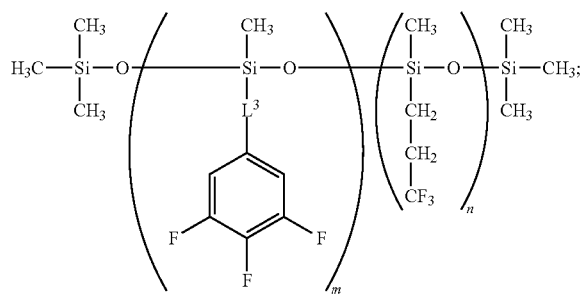

where $L^3$ is independently —$(CH_2)_2$— or —$CH(CH_3)$—

The base copolymer having the following structure (commercially available from Gelest, Inc.):

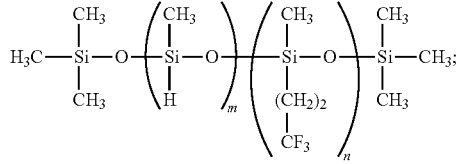

wherein the molar ratio of hydride:trifluoropropyl (e.g., m:n) was 18:82 or 38:62; was reacted with a compound of Formula (D3) following the process described in Example 1 to produce the following copolymer:

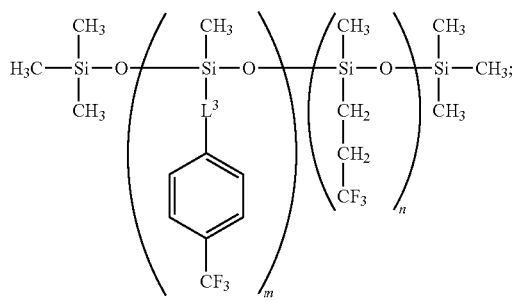

where $L^3$ is independently —$(CH_2)_2$— or —$CH(CH_3)$—.

If the refractive index of the resulting polymer was too low, the fluoro content of the compound of Formula (D) was varied. If the resulting copolymer was too soluble, the hydide concentration of the base copolymer shown above was varied. In addition, the molecular weight of the base copolymer was varied to adjust the viscosity.

When the base copolymer was reacted with D1, the resulting copolymer was partially solid. When the base copolymer was reacted with D2 or D3, the refractive index and solubility were excellent.

The resulting copolymer was purified. In particular, the material was processed through an activated charcoal extraction procedure to remove any residual catalyst (e.g., from polymerization or hydrosilylation). The material was also run through a hexane extraction procedure ten times to intentionally remove any material that would be likely to migrate into the silicone.

It is understood that the examples and aspects described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A copolymer of Formula (B):

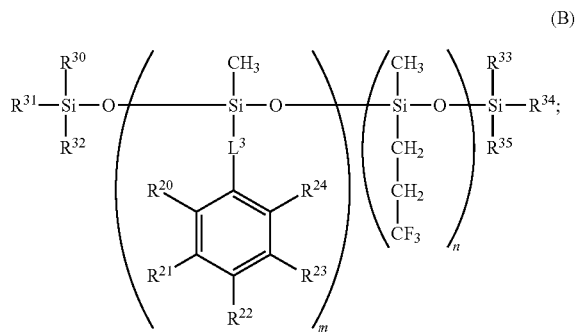

wherein:
$R^{20}$, $R^{21}$, $R^{22}$, $R^{23}$, and $R^{24}$ are each independently hydrogen, fluorine, or $C_{1-4}$ alkyl substituted with at least one fluorine; wherein at least one of $R^{20}$, $R^{21}$, $R^{22}$, $R^{23}$, and $R^{24}$ is fluorine;
$L^3$ is independently a bond, —$(CH_2)_2$—, or —$CH(CH_3)$—;
$R^{30}$, $R^{31}$, $R^{32}$, $R^{33}$, $R^{34}$, and $R^{35}$ are each independently —$CH_3$ or —$CF_3$;
m and n are each independently an integer from 1 to 50.

2. The copolymer of claim 1, wherein $R^{20}$ and $R^{24}$ are hydrogen; and $R^{21}$, $R^{22}$, and $R^{23}$ are fluorine.

3. The copolymer of claim 1, wherein $L^3$ is a bond.

4. The copolymer of claim 1, wherein the ratio of m:n is from about 10:90 to about 90:10.

5. The copolymer of claim 1 having a number average molecular weight from about 2,000 to about 5,000.

6. A composition comprising a plurality of the copolymer of claim 1.

7. The composition of claim 6 having a viscosity from about 500 cP to about 10,000 cP.

8. The composition of claim 6 having a refractive index from about 1.40 to about 1.50.

9. A lens comprising:
(i) an anterior portion comprising a refractive optical element;
(ii) a posterior portion; and
(iii) an enclosed cavity between the anterior portion and the posterior portion, wherein the enclosed cavity comprises the copolymer of claim 1.

10. A method of treating a cataract in an eye of a patient in need thereof, the method comprising implanting an intraocular lens into the eye of the patient;
wherein the intraocular lens comprises:
(i) an anterior portion comprising a refractive optical element;
(ii) a posterior portion; and
(iii) an enclosed cavity between the anterior portion and the posterior portion, wherein the enclosed cavity comprises the copolymer of claim 1.

11. A copolymer of Formula (A):

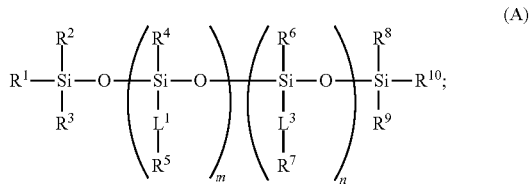

wherein:

$R^1$, $R^2$, $R^3$, $R^8$, $R^9$, and $R^{10}$ are each independently hydrogen, substituted or unsubstituted alkyl, substituted or unsubstituted heteroalkyl, substituted or unsubstituted aryl, or substituted or unsubstituted heteroaryl;

$R^4$ and $R^6$ are each independently hydrogen, substituted or unsubstituted alkyl, substituted or unsubstituted heteroalkyl, substituted or unsubstituted aryl, or substituted or unsubstituted heteroaryl;

$L^1$ and $L^2$ are each independently a bond, substituted or unsubstituted alkylene, or substituted or unsubstituted heteroalkylene;

$R^5$ is independently $R^{5A}$-substituted aryl; wherein $R^{5A}$ is independently fluorine;

$R^7$ is independently unsubstituted or $R^{7A}$-substituted alkyl, unsubstituted or $R^{7A}$-substituted heteroalkyl, unsubstituted or $R^{7A}$-substituted aryl, or unsubstituted or $R^{7A}$-substituted heteroaryl; wherein $R^{7A}$ is independently fluorine, $R^{7B}$-substituted alkyl, or $R^{7B}$-substituted heteroalkyl; wherein $R^{7B}$ is fluorine; and m and n are each independently an integer from 1 to about 100.

12. The copolymer of claim 11, wherein $R^7$ is independently unsubstituted or $R^{7A}$-substituted alkyl or unsubstituted or $R^{7A}$-substituted aryl; wherein $R^{7A}$ is independently fluorine or $R^{7B}$-substituted alkyl; wherein $R^{7B}$ is fluorine.

13. The copolymer of claim 11, wherein $R^7$ is $R^{7A}$-substituted alkyl.

14. The copolymer of claim 11, wherein:

$R^1$, $R^2$, $R^3$, $R^8$, $R^9$, and $R^{10}$ are each independently hydrogen, unsubstituted $C_1$-$C_6$ alkyl, $C_1$-$C_6$ alkyl substituted with at least one fluorine, $C_1$-$C_6$ alkyl substituted with a 6 membered aryl that is substituted with at least one fluorine, or 6 membered aryl substituted with at least one fluorine;

$R^4$ and $R^6$ are each independently hydrogen, substituted or unsubstituted $C_1$-$C_6$ alkyl, or substituted or unsubstituted phenyl;

$L^1$ and $L^2$ are each independently a bond or a substituted or unsubstituted $C_1$-$C_6$ alkylene;

$R^5$ is $R^{5A}$-substituted aryl;

$R^{5A}$ is independently fluorine or $C_1$-$C_4$ alkyl substituted with at least one fluorine;

$R^7$ is independently phenyl, unsubstituted $C_1$-$C_6$ alkyl, or $C_1$-$C_6$ alkyl substituted with at least one fluorine; and m and n are each independently an integer from 1 to about 50.

15. The copolymer of claim 11, wherein:

$R^1$, $R^2$, $R^3$, $R^8$, $R^9$, and $R^{10}$ are each independently —$CH_3$ or —$CF_3$;

$R^4$ and $R^6$ are each independently unsubstituted $C_1$-$C_4$ alkyl;

$L^1$ is a bond;

$L^2$ is unsubstituted $C_1$-$C_4$ alkylene;

$R^5$ is phenyl substituted with 1 to 5 fluorine;

$R^7$ is $R^{7A}$-substituted $C_1$-$C_4$ alkyl;

$R^{7A}$ is fluorine; and m and n are each independently an integer from 1 to about 50.

16. The copolymer of claim 11, wherein the copolymer has a number average molecular weight of about 1,000 to about 6,000.

17. A composition comprising a plurality of the copolymer of claim 11.

18. The composition of claim 17 having:
(a) a viscosity from about 500 cP to about 10,000 cP;
(b) a refractive index from about 1.40 to about 1.47;

(c) a light transmittance of at least 95% in the visible light range of 400 nm to 700 nm; or
(d) a combination of two or more of (a), (b), and (c).

19. A lens comprising:
(i) an anterior portion comprising a refractive optical element;
(ii) a posterior portion; and
(iii) an enclosed cavity between the anterior portion and the posterior portion, wherein the enclosed cavity comprises the copolymer of Formula (B):

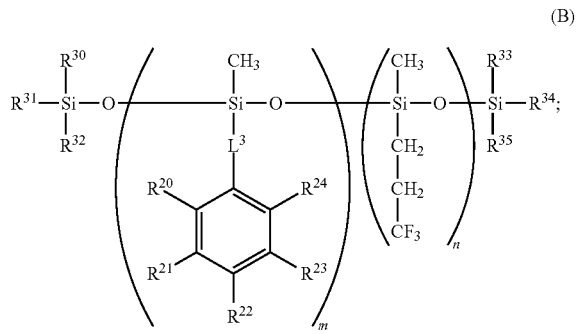

wherein:

$R^{20}$, $R^{21}$, $R^{22}$, $R^{23}$, and $R^{24}$ are each independently hydrogen, fluorine, or $C_{1-4}$ alkyl substituted with at least one fluorine;

$L^3$ is independently a bond, —$(CH_2)_2$—, or —CH($CH_3$)—;

$R^{30}$, $R^{31}$, $R^{32}$, $R^{33}$, $R^{34}$, and $R^{35}$ are each independently —$CH_3$ or —$CF_3$;

m and n are each independently an integer from 1 to 50.

20. A method of treating a cataract in an eye of a patient in need thereof, the method comprising implanting an intraocular lens into the eye of the patient;
wherein the intraocular lens comprises:
(i) an anterior portion comprising a refractive optical element;
(ii) a posterior portion; and
(iii) an enclosed cavity between the anterior portion and the posterior portion, wherein the enclosed cavity comprises the copolymer of claim 11.

21. The lens of claim 19, wherein $R^{20}$ and $R^{24}$ are hydrogen; $R^{21}$, $R^{22}$, and $R^{23}$ are fluorine; and $L^3$ is a bond.

22. The lens of claim 19, wherein $R^{20}$, $R^{21}$, $R^{22}$, $R^{23}$, and $R^{24}$ are hydrogen; and $L^3$ is a bond.

23. The lens of claim 19, wherein the ratio of m:n is from about 10:90 to about 90:10.

24. The lens of claim 19, wherein the copolymer has a number average molecular weight from about 2,000 to about 5,000.

25. The lens of claim 19, wherein the anterior portion and the posterior portion comprise a silicone elastomer.

26. The lens of claim 19, wherein the lens is an intraocular lens.

27. A method of treating a cataract in an eye of a patient in need thereof, the method comprising implanting the lens of claim 26 into the eye of the patient.

28. A method of treating a cataract in an eye of a patient in need thereof, the method comprising implanting an intraocular lens into the eye of the patient;
wherein the intraocular lens comprises:
(i) an anterior portion comprising a refractive optical element;

(ii) a posterior portion; and
(iii) an enclosed cavity between the anterior portion and the posterior portion, wherein the enclosed cavity comprises the copolymer of Formula (B):

(B)

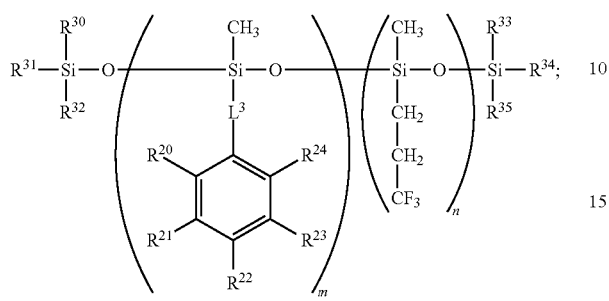

wherein:
$R^{20}$, $R^{21}$, $R^{22}$, $R^{23}$, and $R^{24}$ are each independently hydrogen, fluorine, or $C_{1-4}$ alkyl substituted with at least one fluorine;
$L^3$ is independently a bond, —$(CH_2)_2$—, or —CH$(CH_3)$—;
$R^{30}$, $R^{31}$, $R^{32}$, $R^{33}$, $R^{34}$, and $R^{35}$ are each independently —$CH_3$ or —$CF_3$;
m and n are each independently an integer from 1 to 50.

29. A lens comprising:
(i) an anterior portion comprising a refractive optical element;
(ii) a posterior portion; and
(iii) an enclosed cavity between the anterior portion and the posterior portion, wherein the enclosed cavity comprises a liquid silicone composition comprising a plurality of the copolymer of Formula (B), wherein the liquid silicone composition has a refractive index from about 1.40 to about 1.47, and wherein the copolymer of Formula (B) is:

(B)

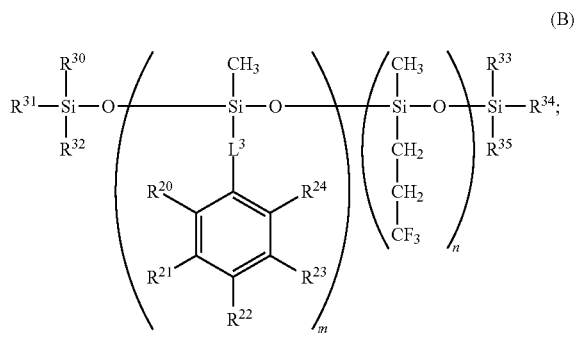

wherein:
$R^{20}$, $R^{21}$, $R^{22}$, $R^{23}$, and $R^{24}$ are each independently hydrogen, fluorine, or $C_{1-4}$ alkyl substituted with at least one fluorine;
$L^3$ is independently a bond, —$(CH_2)_2$—, or —CH$(CH_3)$—;
$R^{30}$, $R^{31}$, $R^{32}$, $R^{33}$, $R^{34}$, and $R^{35}$ are each independently —$CH_3$ or —$CF_3$; and
m and n are each independently an integer from 1 to 50.

30. The lens of claim 29, wherein $R^{20}$ and $R^{24}$ are hydrogen; and $R^{21}$, $R^{22}$, and $R^{23}$ are fluorine; and $L^3$ is a bond.

31. The lens of claim 29, wherein $R^{20}$, $R^{21}$, $R^{22}$, $R^{23}$, and $R^{24}$ are hydrogen; and $L^3$ is a bond.

32. The lens of claim 29, wherein the ratio of m:n is from about 10:90 to about 90:10.

33. The lens of claim 29, wherein the copolymer has a number average molecular weight from about 2,000 to about 5,000.

34. The lens of claim 29, wherein the liquid silicone composition has a viscosity from about 500 cP to about 10,000 cP.

35. The lens of claim 29, wherein the liquid silicone composition has a light transmittance of at least 95% in the visible light range of 400 nm to 700 nm.

36. The lens of claim 29, wherein the liquid silicone composition has a refractive index from about 1.41 to about 1.46.

37. The lens of claim 29, wherein the anterior portion and the posterior portion comprise a silicone elastomer.

38. The lens of claim 29, wherein the lens is an intraocular lens.

39. A method of treating a cataract in an eye of a patient in need thereof, the method comprising implanting the lens of claim 38 into the eye of the patient.

40. A lens comprising:
(i) an anterior portion comprising a refractive optical element;
(ii) a posterior portion; and
(iii) an enclosed cavity between the anterior portion and the posterior portion, wherein the enclosed cavity comprises the copolymer of claim 11.

* * * * *